(12) United States Patent
Arnold et al.

(10) Patent No.: US 6,525,099 B1
(45) Date of Patent: Feb. 25, 2003

(54) N-SUBSTITUTED SULFONAMIDE DERIVATIVES

(75) Inventors: Macklin Brian Arnold, Morgantown, IN (US); Winton Dennis Jones, Carmel, IN (US); Paul Leslie Ornstein, Carmel, IN (US); Hamideh Zarrinmayeh, Carmel, IN (US); Dennis Michael Zimmerman, Zionsville, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 09/744,419

(22) PCT Filed: Jul. 28, 1999

(86) PCT No.: PCT/US99/17017
§ 371 (c)(1),
(2), (4) Date: Jan. 23, 2001

(87) PCT Pub. No.: WO00/06537
PCT Pub. Date: Feb. 10, 2000

Related U.S. Application Data

(60) Provisional application No. 60/094,921, filed on Jul. 31, 1998.

(51) Int. Cl.[7] ................. A61K 31/18; A61K 31/16; A61K 31/24; A61K 31/34; A61K 31/38
(52) U.S. Cl. ................. 514/605; 514/183; 514/210.01; 514/217.12; 514/222.2; 514/237.5; 514/238.2; 514/252.12; 514/255; 514/256; 514/331; 514/336; 514/354; 514/355; 514/357; 514/364; 514/365; 514/367; 514/378; 514/381; 514/423; 514/427; 514/428; 514/438; 514/443; 514/444; 514/445; 514/447; 514/448; 514/471; 514/538; 514/600; 514/601; 514/602; 514/603; 514/604; 540/450; 540/610; 544/3; 544/160; 544/335; 544/392; 544/395; 544/398; 546/232; 546/280.4; 546/316; 546/323; 546/338; 548/110; 548/131; 548/146; 548/179; 548/201; 548/205; 548/240; 548/247

(58) Field of Search ................. 514/63, 183, 210.01, 514/217.12, 222.2, 237.5, 238.2, 252.12, 255, 256, 331, 336, 354, 355, 357, 364, 365, 367, 378, 381, 423, 427, 428, 438, 443, 444, 445, 447, 448, 471, 538, 601, 600, 602, 603, 604, 605; 540/450, 610; 544/3, 160, 335, 392, 395, 398; 546/232, 280.4, 316, 323, 338; 548/110, 131, 146, 179, 201, 205, 240, 247, 248, 252, 537, 561, 569, 950; 549/57, 58, 59, 65, 68, 72, 75, 487, 491; 560/10, 12; 564/79, 80, 86, 89, 92, 95, 97, 99

(56) References Cited

U.S. PATENT DOCUMENTS

| | | | |
|---|---|---|---|
| 4,370,328 A | 1/1983 | Campbell et al. | 424/250 |
| 5,962,462 A * | 10/1999 | Mills et al. | 514/278 |
| 6,174,922 B1 | 1/2001 | Arnold et al. | 514/604 |
| 6,355,655 B1 | 3/2002 | Escribano et al. | 514/315 |
| 6,358,982 B1 | 3/2002 | Cantrell et al. | 514/331 |

FOREIGN PATENT DOCUMENTS

| | | |
|---|---|---|
| WO | WO 98/33496 | 2/1997 |
| WO | WO00/06083 | 2/2000 |
| WO | WO00/06148 | 2/2000 |

OTHER PUBLICATIONS

Barker et al., Dehalogenation of 1–Halogenothienyl–di– and –tetra–hydroisoquinolines by Sodium Methoxide in Dimethyl Sulphoxide, J. Chem. Soc. Perkin Trans. I, No. 2, pp. 275–281, Feb. 1985.*

* cited by examiner

*Primary Examiner*—Brenda Coleman
(74) *Attorney, Agent, or Firm*—Nelsen L. Lentz

(57) ABSTRACT

The present invention provides certain N-substituted sulfonamide derivatives useful for potentiating glutamate receptor function in a mammal and therefore, useful for treating a wide variety of conditions, such as psychiatric and neurological disorders.

8 Claims, No Drawings

N-SUBSTITUTED SULFONAMIDE DERIVATIVES

This is a 371 of PCT/US99/17017 filed Jul. 28, 1999 which claims priority to U.S. Provisional Application No. 60/094,921 filed Jul. 31, 1998.

The present invention relates to the potentiation of glutamate receptor function using certain N-substituted sulfonamide derivatives. It also relates to novel N-substituted sulfonamide derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are unknown.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron.* Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulfonamides, S-oxides and homologs which are said to potentiate membrane currents induced by kainic acid and AMPA.

U.S. Pat. No. 3,143,549 discloses certain phenylalkylsulfamides, including 1-methyl-2-phenylethyl dimethylsulfamide. The compounds are said to have central nervous system activity, in particular anti-anxiety and tranquilizing properties.

U.S. Pat. No. 3,267,139 discloses certain N'-trimethylacetyl-N-phenylalkylsulfamides and -phenylcyclopropylsulfamides having central nervous system activity and anticonvulsant activity. The compounds are also said to produce Parkinson-like symptoms in experimental animals.

U.S. Pat. No. 3,860,723 discloses a method of increasing feed intake of healthy animals using certain phenylalkylsulfamides.

Foye et al., *J. Pharm. Sci.* (1971), 60(7), 1095–6 discloses certain phenylalkyl methylsulfonamides including N-1-methyl-2-phenylethyl methanesulfonamide, having hypotensive activity.

British Patent Specification Number 1,059,360 discloses certain phenylalkylsulfamides having activity as sedatives, narcotics and anti-convulsants, including 1-(1-methyl-2-phenylethylaminosulphonyl)piperidine.

U.S. Pat. No. 4,210,749 discloses N-1-methyl-2-phenyl-3-methoxy ethyl butane-sulfonamide.

Gualtieri et al., *J. Pharm. Sci.*, (1973), 62(5), 849–851 discloses N-1-methyl-2-phenylethyl butanesulfonamide and its evaluation as a mosquito repellent.

Foye et al., *J. Pharm. Sci.* (1979), 68(5), 591–5 discloses N-1-methyl-2-(4-chlorophenyl)ethyl methane-sulfonamide.

Foye and Sane, *J. Pharm. Sci.* (1977), 66(7), 923–6 discloses N-methanesulfonyl and N-trifluoromethanesulfonyl derivatives of amphetamines and certain 4-substituted analogs thereof, and their evaluation for central nervous system and anorexic effects.

European patent application publication no. EP-A1-0657442 discloses certain naphthyloxyacetic acid derivatives as PEG2 agonists and antagonists. N-(2,2-diphenylethyl)-methanesulfonamide is disclosed as an intermediate at page 53, line 38.

U.S. Pat. No. 3,629,332 discloses certain N-aryl- and N-heteroarylalkyl fluoroalkane sulfonamides as plant growth modifiers, including N-(alpha-methylphenylethyl) trifluoromethanesulfonamide, difluoromethanesulfonamide and fluoromethanesulfonamide. Some of the compounds are also said to have other biological activity, including insecticidal, acaricidal, nematicidal, analgesic and anti-inflammatory activity.

Ampakines have been shown to improve memory in a variety of animal tests. Staubli et al., *Proc. Natl. Acad. Sci.*, Vol. 91, pp 777–781, 1994, *Neurobiology*, and Arai et al., *The Journal of Pharmacology and Experimental Therapeutics*, 278: 627–638,1996.

It has now been found that cyclothiazide and certain N-substituted sulfonamide derivatives potentiate agonist-induced excitability of human GluR4B receptor expressed in HEK 293 cells. Since cyclothiazide is known to potentiate glutamate receptor function in vivo, it is believed that this finding portends that the N-substituted sulfonamide derivatives will also potentiate glutamate receptor function in vivo, and hence that the compounds will exhibit ampakine-like behavior.

The present invention provides compounds of formula I:

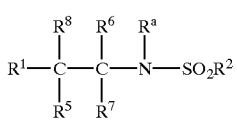

formula I wherein $R^a$ represents (1–6C)alkyl, CO(1–6C)alkyl, CO(aryl), $CO_2$(1–6C)alkyl, $CO_2$(1–6C)alkylaryl, $CO_2$(aryl), $COCH_2OH$, CH(1–6C)$O_2$C(1–6C)alkyl, CO(1–6C)alkylNH(1–6C)alkyl, CO(1–6C)alkylN(1–6C)alkyl$_2$, and CO(1–6C)alkylNR$^e$R$^f$ wherein R$^e$ and R$^f$ together with the nitrogen atom to which they are attached form an azetidinyl, pyrrolidinyl, piperidinyl, morpholino, piperazinyl, hexahydroazepinyl or octahydroazocinyl group;

$R^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo (1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, OCH2CONH or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C)alkylsulfonylamino(1–4C)alkyl, (N-(1–4C)alkoxycarbonyl)(1–4C)alkylsulfonylamino-(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group;

$R^2$ represents (1–6C)alkyl, (3–6C)cycloalkyl, (1–6C)fluoro-alkyl, (1–6C)chloroalkyl, (2–6C)alkenyl, (1–4C)alkoxy(1–4C)alkyl, (1–4C)alkyl$CO_2$(1–4C)alkyl, heteroaromatic, phenyl which is unsubstituted or substituted by halogen, (1–4C)alkyl or (1–4C)alkoxy, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group; and $R^5$, $R^6$, $R^7$ and $R^8$ are each independently selected from the group consisting of hydrogen, (1–6C)alkyl; aryl (1–6C)alkyl; (2–6C)alkenyl; aryl(2–6C)alkenyl and aryl; or two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof.

The present invention provides a method of potentiating glutamate receptor function in a mammal requiring such treatment, which comprises administering an effective amount of a compound of formula I.

According to another aspect, the present invention provides the use of a compound of formula I, or a pharmaceutically acceptable salt thereof as defined hereinabove for the manufacture of a medicament for potentiating glutamate receptor function.

According to yet another aspect, the present invention provides the use of a compound of formula I or a pharmaceutically acceptable salt thereof as defined hereinabove for potentiating glutamate receptor function.

The present invention further provides a method of potentiating glutamate receptor function in a mammal requiring such treatment, which comprises administering an effective amount of a compound of formula:

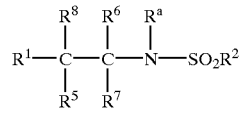

wherein $R^a$ represents (1–6C)alkyl, CO(1–6C)alkyl, CO(aryl), $CO_2$(1–6C)alkyl, $CO_2$(1–6C)alkylaryl, $CO_2$(aryl), COCH$_2$OH, CH(1–6C)O$_2$C(1–6C)alkyl, CO(1–6C)alkylNH(1–6C)alkyl, CO(1–6C)alkylN(1–6C)alkyl$_2$, and CO(1–6C)alkylNR$^e$R$^f$ wherein R$^e$ and R$^f$ together with the nitrogen atom to which they are attached form an azetidinyl, pyrrolidinyl, piperidinyl, morpholino, piperazinyl, hexahydroazepinyl or octahydroazocinyl group;

R$^1$ represents an unsubstituted or substituted aromatic or heteroaromatic group; R$^2$ represents (1–6C)alkyl, (3–6C)cycloalkyl, (1–6C)fluoro-alkyl, (1–6C)chloroalkyl, (2–6C)alkenyl, (1–4C)alkoxy(1–4C)alkyl, (1–4C)alkylCO$_2$(1–4C)alkyl, heteroaromatic, phenyl which is unsubstituted or substituted by halogen, (1–4C)alkyl or (1–4C)alkoxy, or a group of formula R$^3$R$^4$N in which R$^3$ and R$^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group; and R$^5$, R$^6$, R$^7$ and R$^8$ are each independently selected from the group consisting of hydrogen, (1–6C)alkyl; aryl (1–6C)alkyl; (2–6C)alkenyl; aryl(2–6C)alkenyl and aryl; or two of R$^5$, R$^6$, R$^7$ and R$^8$ together with the carbon atom or carbon atoms to which they are attached form a (3–8C) carbocyclic ring; and the remainder of R$^5$, R$^6$, R$^7$ and R$^8$ represent hydrogen; or a pharmaceutically acceptable salt thereof.

In this specification, the term "potentiating glutamate receptor function" refers to any increased responsiveness of glutamate receptors, for example AMPA receptors, to glutamate or an agonist, and includes but is not limited to inhibition of rapid desensitisation or deactivation of AMPA receptors to glutamate.

A wide variety of conditions may be treated or prevented by the compounds of formula I and their pharmaceutically acceptable salts through their action as potentiators of glutamate receptor function. Such conditions include those associated with glutamate hypofunction, such as psychiatric and neurological disorders, for example cognitive disorders; neuro-degenerative disorders such as Alzheimer's disease; age-related dementias; age-induced memory impairment; movement disorders such as tardive dyskinesia, Hungtington's chorea, myoclonus and Parkinson's disease; reversal of drug-induced states (such as cocaine, amphetamines, alcohol-induced states); depression; attention deficit disorder; attention deficit hyperactivity disorder; psychosis; cognitive deficits associated with psychosis; and drug-induced psychosis. The compounds of formula I may also be useful for improving memory (both short term and long term) and learning ability. The present invention provides the use of compounds of formula I for the treatment of each of these conditions.

The term "treating" (or "treat") as used herein includes its generally accepted meaning which encompasses prohibiting, preventing, restraining, and slowing, stopping, or reversing progression, severity, or a resultant symptom.

The present invention includes the pharmaceutically acceptable salts of the compounds defined by formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, g-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "aromatic group" means the same as aryl, and includes phenyl and a polycyclic aromatic carbocyclic ring such as naphthyl.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, triazolyl, tetrazolyl, pyridyl, pyridazinyl, pyrimidyl, benzofuryl, benzothienyl, benzimidazolyl, benzoxazolyl, benzothiazolyl, indolyl and quinolyl.

The term "substituted" as used in the term "substituted aromatic or heteroaromatic group" herein signifies that one or more (for example one or two) substituents may be present, said substituents being selected from atoms and groups which, when present in the compound of formula I, do not prevent the compound of formula I from functioning as a potentiator of glutamate receptor function.

Examples of substituents which may be present in a substituted aromatic or heteroaromatic group include halogen; nitro; cyano; hydroxyimino; (1–10C) alkyl; (2–10C) alkenyl; (2–10C)alkynyl; (3–8C)cycloalkyl; hydroxy(3–8C) cycloalkyl; oxo(3–8C)cycloalkyl; halo(1–10C)alkyl; $(CH_2)_y$ $X^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C) alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl dihydrothiazolyl; (1–4C)alkoxycarbonyl dimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$, or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; (1–10C) alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, $OCONR^{19}$ or $NR^{19}COO$, $R^{15}$ represents hydrogen, (1–10C) alkyl, phenyl(1–4C)alkyl, halo(1–10C)alkyl, (1–4C) alkoxycarbonyl(1–4C)alkyl, (1–4C)alkylsulfonylamino (1–4C)alkyl, N-(1–4C)alkoxycarbonyl)(1–4C) alkylsulfonylamino(1–4C)alkyl, (3–10C)alkenyl, (3–10C) alkynyl, (3–8C)cycloalkyl, camphoryl, or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C) alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group.

The term (1–10C)alkyl includes (1–8C)alkyl, (1–6C)alkyl and (1–4C)alkyl. Particular values are methyl, ethyl, propyl, isopropyl, butyl, isobutyl, t-butyl, pentyl, hexyl, heptyl, octyl, nonyl and decyl.

The term (2–10C)alkenyl includes (3–10C)alkenyl, (1–8C)alkenyl, (1–6C)alkenyl and (1–4C)alkenyl. Particular values are vinyl and prop-2-enyl.

The term (2–10C)alkynyl includes (3–10C)alkynyl, (1–8C)alkynyl, (1–6C)alkynyl and (3–4C)alkynyl. A particular value is prop-2-ynyl.

The term (3–8C)cycloalkyl, as such or in the term (3–8C) cycloalkyloxy, includes monocyclic and polycyclic groups. Particular values are cyclopropyl, cyclobutyl, cyclopentyl, cyclohexyl and bicyclo[2.2.2]octane. The term includes (3–6C)cycloalkyl: cyclopropyl, cyclobutyl, cyclopentyl and cyclohexyl.

The term hydroxy(3–8C)cycloalkyl includes hydroxycyclopentyl, such as 3-hydroxycyclopentyl.

The term oxo(3–8C)cycloalkyl includes oxocyclopentyl, such as 3-oxocyclopentyl.

The term halogen includes fluorine, chlorine, bromine and iodine.

The term halo(1–10C)alkyl includes fluoro(1–10C)alkyl, such as trifluoromethyl and 2,2,2-trifluoroethyl, and chloro (1–10C)alkyl such as chloromethyl.

The term cyano(2–10C)alkenyl includes 2-cyanoethenyl.

The term (2–4C)alkylene includes ethylene, propylene and butylene. A preferred value is ethylene.

The term thienyl includes thien-2-yl and thien-3-yl.

The term furyl includes fur-2-yl and fur-3-yl.

The term oxazolyl includes oxazol-2-yl, oxazol-4-yl and oxazol-5-yl.

The term isoxazolyl includes isoxazol-3-yl, isoxazol-4-yl and isoxazol-5-yl.

The term oxadiazolyl includes [1,2,4]oxadiazol-3-yl and [1,2,4]oxadiazol-5-yl.

The term pyrazolyl includes pyrazol-3-yl, pyrazol-4-yl and pyrazol-5-yl.

The term thiazolyl includes thiazol-2-yl, thiazol-4-yl and thiazol-5-yl.

The term thiadiazolyl includes [1,2,4]thiadiazol-3-yl, and [1,2,4]thiadiazol-5-yl.

The term isothiazolyl includes isothiazol-3-yl, isothiazol-4-yl and isothiazol-5-yl.

The term imidazolyl includes imidazol-2-yl, imidazolyl-4-yl and imidazolyl-5-yl.

The term triazolyl includes [1,2,4]triazol-3-yl and [1,2,4]triazol-5-yl.

The term tetrazolyl includes tetrazol-5-yl.

The term pyridyl includes pyrid-2-yl, pyrid-3-yl and pyrid-4-yl.

The term pyridazinyl includes pyridazin-3-yl, pyridazin-4-yl, pyridazin-5-yl and pyridazin-6-yl.

The term pyrimidyl includes pyrimidin-2-yl, pyrimidin-4-yl, pyrimidin-5-yl and pyrimidin-6-yl.

The term benzofuryl includes benzofur-2-yl and benzofur-3-yl.

The term benzothienyl includes benzothien-2-yl and benzothien-3-yl.

The term benzimidazolyl includes benzimidazol-2-yl.

The term benzoxazolyl includes benzoxazol-2-yl.

The term benzothiazolyl includes benzothiazol-2-yl.

The term indolyl includes indol-2-yl and indol-3-yl.

The term quinolyl includes quinol-2-yl.

The term dihydrothiazolyl includes 4,5-dihydrothiazol-2-yl, and the term (1–4C)alkoxycarbonyldihydrothiazolyl includes 4-methoxycarbonyl4,5-dihydrothiazol-2-yl.

Preferably $R^a$ represents methyl, ethyl, propyl, n-butyl, sec-butyl, methoxycarbonyl, t-butyoxycarbonyl, pivaloyloxymethyl, pivaloyloxyethyl, (((N,N-dimethylamino)ethyl)oxy)carbonyl, or (((morpholino)ethyl)oxy)carbonyl.

More preferably $R^a$ represents methyl, t-butyoxycarbonyl, pivaloyloxymethyl, (((N,N-dimethylamino)ethyl)oxy)carbonyl or (((morpholino)ethyl)oxy)carbonyl.

Preferably either one or two of $R^5$, $R^6$, $R^7$ and $R^8$ represents (1–6C)alkyl, aryl(1–6C)alkyl, (2–6C)alkenyl, aryl(2–6C)alkenyl or aryl, or two of $R^5$, $R^6$, $R^7$ and $R^8$ together with the carbon atom or carbon atoms to which they are attached form a (3–8C)carbocyclic ring; and the remainder of $R^5$, $R^6$, $R^7$ and $R^8$ represent hydrogen.

Examples of a (1–6C)alkyl group represented by $R^5$, $R^6$, $R^7$ and $R^8$ are methyl, ethyl and propyl. An example of an aryl(1-C)alkyl group is benzyl. An example of a (2–6C) alkenyl group is prop-2-enyl. An example of a (3–8C) carbocyclic ring is a cyclopropyl ring.

More preferably $R^6$ and $R^7$ represent hydrogen.

Preferably $R^5$ and $R^8$ each independently represents hydrogen or (1–4C)alkyl, or together with the carbon atom to which they are attached form a (3–8C) carbocyclic ring.

More preferably $R^8$ represents methyl or ethyl, or $R^5$ and $R^8$ together with the carbon atom to which they are attached form a cyclopropyl ring. When $R^8$ represents methyl or ethyl, $R^5$ preferably represents hydrogen or methyl.

Especially preferred are compounds in which $R^8$ represents methyl and $R^5$, $R^6$ and $R^7$ represent hydrogen.

Preferably $R^3$ and $R^4$ each represent methyl.

Examples of values for $R^2$ are methyl, ethyl, propyl, 2-propyl, butyl, 2-methylpropyl, cyclohexyl, trifluoromethyl, 2,2,2-trifluoroethyl, chloromethyl, ethenyl, prop-2-enyl, methoxyethyl, phenyl, 4-fluorophenyl, or dimethylamino. Preferably $R^2$ is ethyl, 2-propyl or dimethylamino.

Examples of values for $R^9$ are hydrogen, methyl, ethyl, propyl, isopropyl, t-butyl, ethenyl, cyclopropyl, cyclobutyl, cyclopentyl, cyclohexyl, 2-pyrrolidinyl, morpholino or 2-tetrahydrofuryl.

Examples of values for $R^{15}$ are hydrogen, methyl, ethyl, propyl, isopropyl, butyl, t-butyl, benzyl, 2,2,2-trifluoroethyl, 2-methoxycarbonylethyl, cyclohexyl, 10-camphoryl, phenyl, 2-fluorophenyl, 3-fluorophenyl, 2-trifluoromethylphenyl, 4-trifluoromethylphenyl, 2-methoxyphenyl, 3-methoxyphenyl, 4-methoxyphenyl, 1-(5-dimethylamino)naphthyl, and 2-thienyl.

$X^1$ preferably represents O, CO, CONH or NHCO.

z is preferably 0.

$R^9$ is preferably (1–4C)alkyl, (2–4C)alkenyl, (3–6C) cycloalkyl, pyrrolidinyl, morpholino or tetrahydrofuryl.

Particular values for the groups $(CH_2)_yX^1R^9$ and $(CH_2)_zX^3R^{15}$ include (1–10C)alkoxy, including (1–6C)alkoxy and (1–4C)alkoxy, such as methoxy, ethoxy, propoxy, isopropoxy and isobutoxy; (3–10C)alkenyloxy, including (3–6C) alkenyloxy, such as prop-2-enyloxy; (3–10C)alkynyloxy, including (3–6C)alkynyloxy, such as prop-2-ynyloxy; and (1–6C)alkanoyl, such as formyl and ethanoyl.

Examples of particular values for y are 0 and 1.

Examples of particular values for z are 0 1, 2 and 3.

$L^a$ and $L^b$ preferably each independently represents $CH_2$.

$X^2$ preferably represents a bond, O, NH, CO, CH(OH), CONH, NHCONH or $OCH_2CONH$.

Preferably the group $(CH_2)_yX^1R^9$ represents CHO; $COCH_3$, $OCH_3$; $OCH(CH_3)_2$; $NHCOR^9$ in which $R^9$ represents methyl, ethyl, isopropyl, t-butyl, ethenyl, cyclopropyl, cyclobutyl, cyclopentyl, cyclohexyl, 2-pyrolidinyl or morpholino; $CONHR^9$ in which $R^9$ represents cyclopropyl or cyclopentyl; $NHCOOCH3$; or 2-tetrahydrofurylmethoxy.

Preferably the group $(CH_2)_zX^3R^{15}$ represents $NH_2$; $CH_2NH_2$; $(CH_2)_2NH_2$; $(CH_2)_3NH_2$; $CONH_2$; $CONHCH_3$; $CON(CH_3)_2$; $N(C_2H_5)_2$; $CH_2OH$; $CH(OH)CH_3$; $CH(OH)CH_2CH_2$; CHO; $COCH_3$; COOH; $COOCH_3$; $CH_2NHCOOC(CH_3)_3$; $(CH_2)_2NHCOOC(CH_3)_3$; $NHSO_2CH(CH_3)_2$; a group of formula $(CH_2)_2NHSO_2R^{15}$ in which $R^{15}$ represents $CH_3$, $CH_2CH_3$, $CH(CH_3)_2$, $(CH_2)_2CH_3$, $(CH_3)_3CH_3$, benzyl, $CH_2CF_3$, 2-methoxycarbonylethyl, cyclohexyl, 10-camphoryl, phenyl, 2-fluorophenyl, 4-fluorophenyl, 2-trifluoromethylphenyl, 4-trifluoromethylphenyl, 4-methoxyphenyl, 1-(2-dimethylamino)naphthyl or 2-thienyl; $CH(OH)CH_2NHSO_2CH_3$; $(CH_2)_3NHSO_2CH(CH_3)_2$; $COCH_2N(OCOC(CH_3)_2SO_2CH_3$;

COCH$_2$NHSO$_2$CH$_3$; (CH$_2$)$_2$NHCOR$^{15}$ in which R$^{15}$ represents CH$_3$, CH(CH$_3$)$_2$, CH$_2$CH(CH$_3$)$_2$, phenyl, 3-fluorophenyl, 4-fluorophenyl, benzyl, 2-methoxyphenyl, 4-methoxyphenyl, 2-thienyl, CH=CH, CH=CHCN, OCH$_3$ or O(CH$_2$)$_3$CH$_3$.

Examples of particular values for (L$^a$)$_n$—X$^2$—(L$^b$)$_m$ are a bond, O, NH, S, SO, SO$_2$, CO, CH$_2$, COCH$_2$, COCONH, CH(OH)CH$_2$, CONH, NHCO, NHCONH, CH$_2$O, OCH$_2$, OCH$_2$CONH, CH$_2$NH, NHCH$_2$ and CH$_2$CH$_2$.

R$^{14}$ is preferably an unsubstituted or substituted phenyl, naphthyl, furyl, thienyl, isoxazolyl, thiazolyl, tetrazolyl, pyridyl, pyrimidyl benzothienyl or benzothiazolyl group.

Examples of particular values for R$^{14}$ are phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2,3-difluoro-phenyl, 2,4-difluorophenyl, 3,4-dichlorophenyl, 3,5-dichlorophenyl, 4-cyanophenyl, 3-nitrophenyl, 4-hydroxyiminophenyl, 2-methylphenyl, 4-methylphenyl, 4-ethylphenyl, 3-propylphenyl, 4-t-butylphenyl, 2-prop-2-enylphenyl, 4-(4-(1,1-dioxotetrahydro-1,2-thiazinyl)phenyl, 2-trifluoromethylphenyl, 3-trifluoromethylphenyl, 4-trifluoromethylphenyl, 2-bromomethylphenyl, 2-fluoro-4-trifluoromethylphenyl, 4-(2-cyanoethenyl)phenyl, 4-phenyl, 2-formylphenyl, 3-formylphenyl, 4-formylphenyl, 2-acetylphenyl, 3-acetylphenyl, 4-acetylphenyl, 2-propanoylphenyl, 2-(2-methyl-propanoyl)phenyl, 2-methoxyphenyl, 3-methoxyphenyl, 4-methoxyphenyl, 4-butoxyphenyl, 2-hydroxymethylphenyl, 4-hydroxymethylphenyl, 2-(1-hydroxyethyl)phenyl, 3-(1-hydroxyethyl)phenyl, 4-(1-hydroxyethyl)phenyl, 2-(1-hydroxypropyl)phenyl, 4-(1-hydroxypropyl)phenyl, 2-(1-hydroxy-2,2-dimethyl-propyl)phenyl, 4-trifluoromethoxyphenyl, 2-aminophenyl,4-aminophenyl, 4-N,N-diethylaminophenyl, 4-aminomethylphenyl, 4-(2-aminoethyl)phenyl, 4-(3-aminopropyl)phenyl, 4-carboxyphenyl, 4-carbamoylphenyl, 4-N-methylcarbamoylphenyl, 4-N,N-dimethylcarbamoylphenyl, 2-isopropylaminomethylphenyl, 4-t-butoxycarbonylaminomethylphenyl, 4-(2-isopropoxy-carboxamido)ethylphenyl, 4-(2-t-butoxycarboxamido)ethylphenyl, 4-isopropylsulfonylaminophenyl, 4-(2-methanesulfonylamino)ethylphenyl, 4-(2-ethylsulfonylamino)ethylphenyl, 4-(3-isopropylsulfonylamino)propylphenyl, 4-(1-(2-(2-propane)sulfonylamino)propyl)phenyl, 4-(2-propylsulfonyl-amino)ethylphenyl, 4-(2-isopropylsulfonylamino)ethylphenyl, 4-(2-butylsulfonylamino)ethylphenyl, 4-(1-isopropyl-sulfonylaminomethyl)ethylphenyl, 4-(1-hydroxy-2-methane-sulfonylamino)ethylphenyl, 4-(2-(2,2,2-trifluoroethyl)sulfonylaminoethyl)phenyl, 4-(2-cyclohexylsulfonylamino)-ethylphenyl, 4-(2-(2,2,2-trifluoroethyl)sulfonylamino)-ethylphenyl, 4-(2-N,N-dimethylaminosulfonylamino)-ethylphenyl, 4-(2-phenylsulfonylaminoethyl)phenyl, 4-(2-(2-fluorophenyl) sulfonylaminoethyl)phenyl, 4-(2-(4-fluorophenyl)sulfonylaminoethyl)phenyl, 4-(2-(2-trifluoromethylphenyl)sulfonylaminoethyl)phenyl, 4-(2-(4-trifluoromethylphenyl)sulfonylaminoethyl)phenyl, 4-(2-(4-methoxyphenyl)sulfonylaminoethyl)phenyl, 4-(2-(1-(5-dimethylamino) napthalenesulfonylamino)ethyl)phenyl, 4-(2-(2-thienyl)sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonyl-amino)ethyl)phenyl, 4-(2-phenylacetamido)ethyl)phenyl, 4-methanesulfonylaminoethanoylphenyl, 4-(N-(t-butoxycarbonyl)methanesulfonylaminoethanoyl)phenyl, 4-(2-(2-thienylcarboxamido)ethyl)phenyl, thien-2-yl, 5-hydroxymethylthien-2-yl, 5-formylthien-2-yl, thien-3-yl, 5-hydroxymethylthien-3-yl, 5-formylthien-3-yl, 2-bromothien-3-yl, fur-2-yl, 5-nitrofur-2-yl, fur-3-yl, isoxazol-5-yl, 3-bromoisoxazol-5-yl, isoxazol-3-yl, 5-trimethylsilylisoxazol-3-yl, 5-methylisoxazol-3-yl, 5-hydroxymethylisoxazol-3-yl, 5-methyl-3-phenylisoxazol4-yl, 5-(2-hydroxyethyl)isoxazol-3-yl, 5-acetylisoxazol-3-yl, 5-carboxyisoxazol-3-yl, 5-N-methylcarbamoylisoxazol-3-yl, 5-methoxycarbonylisoxazol-3-yl, 3-bromo[1,2,4]oxadiazol-5-yl, pyrazol-1-yl, thiazol-2-yl, 4-hydroxymethylthiazol-2-yl, 4-methoxycarbonylthiazol-2-yl, 4-carboxythiazol-2-yl, imidazol-1-yl, 2-sulfhydryl-imidazol-1-yl, [1,2,4]triazol-1-yl, tetrazol-5-yl, 2-methyltetrazol-5-yl, 2-ethyltetrazol-5-yl, 2-isopropyl-tetrazol-5-yl, 2-(2-propenyl)tetrazol-5-yl, 2-benzyl-tetrazol-5-yl, pyrid-2-yl, 5-ethoxycarbonylpyrid-2-yl, pyrid-3-yl, 6-chloropyrid-3-yl, pyrid-4-yl, 5-trifluoromethylpyrid-2-yl, 6-chloropyridazin-3-yl, 6-methylpyridazin-3-yl, 6-methoxypyrazin-3-yl, pyrimidin-5-yl, benzothien-2-yl, benzothiazol-2-yl, and quinol-2-yl.

Examples of an unsubstituted or substituted aromatic or heteroaromatic group represented by R$^1$ are unsubstituted or substituted phenyl, furyl, thienyl (such as 3-thienyl) and pyridyl (such as 3-pyridyl).

More preferably, R$^1$ represents 2-naphthyl or a group of formula

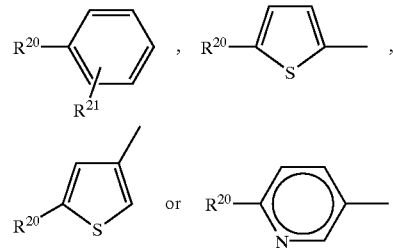

in which

R$^{20}$ represents halogen; nitro; cyano; hydroxyimino; (1–10C)alkyl; (2–10C)alkenyl; (2–10C)alkynyl; (3–8C)cyclo-alkyl; hydroxy(3–8C)cycloalkyl; oxo (3–8C)cycloalkyl; halo(1–10C)alkyl; (CH$_2$)$_y$X$^1$R$^9$ in which y is 0 or an integer of from 1 to 4, X$^1$ represents O, S, NR$^{10}$, CO, COO, OCO, CONR$^{11}$, NR$^{12}$CO, NR$^{12}$COCOO, OCONR$^{13}$, R$^9$ represents hydrogen, (1–10C) alkyl, (3–10C)alkenyl, (3–10C)alkynyl, pyrrolidinyl, tetrahydrofuryl, morpholino or (3–8C) cycloalkyl and R$^{10}$, R$^{11}$, R$^{12}$ and R$^{13}$ each independently represents hydrogen or (1–10C)alkyl, or R$^9$ and R$^{10}$, R$^{11}$, R$^{12}$ or R$^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; tetrazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyl-dihydrothiazolyl; (1–4C)alkoxycarbonyldimethyl-dihydrothiazolyl; tetrahydrothienyl; tetrahydrofuryl; tetrahydrothiopyranyl; tetrahydropyranyl; indolyl; benzofuryl; benzothienyl; benzimidazolyl; benzothiazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCONH, NHCOO, COCONH, $OCH_2CONH$ or CH=CH, NHCO, $L^a$ and $L^b$ each represent (1–4C) alkylene, one of n and m is 0 or 1 and the other is 0, and $R^{14}$ represents a phenyl or hetero-aromatic group which is unsubstituted or substituted by one or two of halogen; nitro; cyano; (1–10C)alkyl; (2–10C)alkenyl; (2–10C)alkynyl; (3–8C)cycloalkyl; 4-(1,1-dioxotetrahydro-1,2-thiazinyl); halo(1–10C)alkyl; cyano(2–10C)alkenyl; phenyl; $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, halo(1–10C)alkyl, (1–4C)alkoxycarbonyl(1–4C)alkyl, (1–4C)alkylsulfonylamino(1–4C)alkyl, (N-(1–4C)alkoxycarbonyl)(1–4C)alkylsulfonylamino(1–4C)alkyl, (3–10C)alkenyl, (3–10C)alkynyl, (3–8C)cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^{21}$ represents a hydrogen atom, a halogen atom, a (1–4C)alkyl group or a (1–4C)alkoxy group.

Examples of particular values for $R^{20}$ are fluorine, chlorine, bromine, cyano, hydroxyimino, methyl, ethyl, propyl, 2-propyl, butyl, 2-methylpropyl, 1,1-dimethylethyl, cyclopentyl, cyclohexyl, 3-hydroxycyclopentyl, 3-oxocyclopentyl, methoxy, ethoxy, propoxy, 2-propoxy, acetyl, acetylamino, ethylcarboxamido, propylcarboxamido, 1-butanoylamido, t-butylcarboxamido, acryloylamido, 2-pyrrolidinylcarboxamido, 2-tetrahydrofurylmethoxy, morpholinocarboxamido, methyloxalylamido, cyclopropylcarboxamido, cyclobutylcarboxamido, cyclopentylcarboxamido, cyclohexylcarboxamido, cyclopropylcarbamoyl, cyclopentylcarbamoyl, pyrrolidin-1-yl, morpholino, piperidin-1-yl, N-methylpiperazinyl, N-benzylpiperazinyl, 2-thienyl, 3-thienyl, 2-furyl, 3-furyl, isoxazol-3-yl, thiazol-2-yl, tetrazol-5-yl, pyrid-2-yl, pyrid-3-yl, pyrid-4-yl, pyrimidin-5-yl, 4,5-dihydrothiazol-2-yl, 4,5-dihydro-4-methoxycarbonylthiazol-2-yl, 4,5-dihydro4-methoxy-carbonyl-5,5-dimethylthiazol-2-yl, benzothien-2-yl, benzothiazol-2-yl, phenyl, 2-fluorophenyl, 3-fluorophenyl, 2,3-difluorophenyl, 4-chlorophenyl, 3,4-dichlorophenyl, 3,5-dichlorophenyl, 3-nitrophenyl, 4-cyanophenyl, 2-methylphenyl, 4-methylphenyl, 4-(4-(1,1-dioxotetrahydro-1,2-thiazinyl)phenyl, 3-trifluoromethylphenyl, 4-trifluoro-methylphenyl, 4-(2-cyanoethenyl)phenyl, 2-formylphenyl, 3-formylphenyl, 4-formylphenyl, 3-acetylphenyl, 4-acetylphenyl, 4-carboxyphenyl, 2-methoxyphenyl, 4-methoxyphenyl, 2-hydroxymethylphenyl, 4-hydroxymethylphenyl, 3-(1-hydroxyethyl)phenyl, 4-(1-hydroxyethyl)phenyl, 4-(1-hydroxypropyl)phenyl, 2-aminophenyl, 4-aminophenyl, 4-N,N-diethylaminophenyl, 4-aminomethylphenyl, 4-(2-aminoethyl)-phenyl, 4-(3-aminopropyl)phenyl, 4-(2-acetylaminoethyl)-phenyl, 4-t-butoxycarboxylaminoethyl) phenyl, 4-(2-t-butoxycarboxylaminoethyl)phenyl, benzylsulfonylamino, 4-isopropylsulfonylaminophenyl, 4-(2-methanesulfonylaminoethyl)phenyl, 4-(2-ethylsulfonylaminoethyl)phenyl, 4-(2-propylsulfonylaminoethyl)phenyl, 4-(2-butylsulfonyl-aminoethyl)phenyl, 4-(2-isopropylsulfonylaminoethyl)phenyl, 4-(1-hydroxy-2-methanesulfonylaminoethyl)phenyl, 4-(2-dimethylaminosulfonylaminoethyl)phenyl, 4-(1-(2-(2-propyl)sulfonylaminopropyl)phenyl, 4-(2-(2,2,2-trifluoroethyl)sulfonylaminoethyl)phenyl, 4-(2-cyclohexylsulfonyl-aminoethyl)phenyl, 4-(2-phenylsulfonylaminoethyl)phenyl, 4-(2-(2-fluorophenyl)sulfonylaminoethyl)phenyl, 4-(2-(4-fluorophenyl)sulfonylaminoethyl)phenyl, 4-(2-(2-trifluoromethylphenyl)sulfonylaminoethyl)phenyl, 4-(2-(4-trifluoromethylphenyl)sulfonylaminoethyl)phenyl, 4-(2-(4-methoxyphenyl)sulfonylaminoethyl)phenyl, 4-(2-(1-(5-dimethylamino)napthalenesulfonylamino)ethyl)phenyl, 4-(2-(2-thienyl)sulfonylamino)ethyl)phenyl, 4-(2-benzamidoethyl)-phenyl, 4-(2-(4-fluorobenzamido)ethyl)phenyl, 4-(2-(3-methoxybenzamido)ethyl)phenyl, 4-(2-(3-fluorobenzamido)-ethyl)phenyl, 4-(2-(4-methoxybenzamido)ethyl)phenyl, 4-(2-(2-methoxybenzamido)ethyl)phenyl, 4-(2-(2-thienyl-carboxamido)ethyl)phenyl, 4-carbamoylphenyl, 4-methyl-carbamoylphenyl, 4-dimethylcarbamoylphenyl, 4-(2-(2-methylpropaneamido)ethyl)phenyl, 4-(2-(3-methyl-butaneamido)ethyl)phenyl, benzoylmethyl, benzamido, 2-fluorobenzamido, 3-flurobenzamido, 4-fluorobenzamido, 2,4-difluorobenzamido, 3-chlorobenzamido, 4-chlorobenzamido, 4-bromobenzamido, 4-iodobenzamido, 4-cyanobenzamido, 3-methylbenzamido, 4-methylbenzamido, 4-ethylbenzamido, 4-propylbenzamido, 4-t-butylbenzamido, 4-vinylbenzamido, 2-trifluoromethylbenzamido, 3-trifluoromethylbenzamido, 4-trifluoromethylbenzamido, 2-fluoro-4-trifluoromethylbenzamido, 2-methoxybenzamido, 3-methoxybenzamido, 4-methoxybenzamido, 4-butoxybenzamido, 4-phenylphenyl-carboxamido, 4-benzylcarboxamido, 4-phenoxymethyl-carboxamido, 2-fluorobenzylamino, benzyloxy, 2-fluorobenzyloxy, 2-hydroxy-2-phenylethyl, 2-fluorophenylcarbamoyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonylamino)ethyl)phenyl, 4-(2-phenylacetamido)-ethyl)phenyl, 4-(methanesulfonylaminoethanoyl)phenyl, 4-(N-t-butoxycarbonyl)methanesulfonylaminoethanoyl)phenyl, 2-thienylcarboxamido, 2-furylcarboxamido, 3-(5-methyl-isoxazolyl)carboxamido, 5-isoxazolylcarboxamido, 2-benzothienylcarboxamido, 4-(5-methyl-3-phenylisoxazolyl)-carboxamido, 4-pyridylcarboxamido, 2-(5-nitrofuryl)-carboxamido, 2-pyridylcarboxamido, 6-chloro-2-pyridyl-carboxamido, 2-thienylsulfonamido, 2-thienylmethylamino, 3-thienylmethylamino, 2-furylmethylamino, 3-furylmethylamino, 3-acetylureido and 2-(2-thienyl)ethylureido.

Examples of particular values for $R^{21}$ are hydrogen and chlorine. $R^{21}$ is preferably ortho to $R^{20}$.

Examples of particular values for $R^1$ are 2-naphthyl, 4-bromophenyl, 4-cyanophenyl, 4-benzamidophenyl, 4-methylphenyl, 4-isopropyl-phenyl, 4-isobutylphenyl, 4-t-butylphenyl, 4-methoxyphenyl, 4-isopropoxyphenyl, 4-cyclopentylphenyl, 4-cyclohexylphenyl, 4-(2-hydroxymethylphenyl)phenyl, 4-(4-hydroxymethylphenyl)-phenyl, 4-(2-furyl)phenyl, 4-(3-furyl)phenyl, 4-(2-thienyl)- phenyl, 4-(3-thienyl)phenyl, 4-(pyrrolidin-1-yl)phenyl, 4-(piperidin-1-yl)phenyl, 3-chloro-4-piperidin-1-ylphenyl, 4-benzyloxyphenyl, 4-(2-fluorophenyl)phenyl, 4-(3-fluorophenyl)phenyl, 4-(2-formylphenyl)phenyl, 4-(3-formylphenyl)-phenyl, 4-(4-formylphenyl)phenyl, 4-(4-methylphenyl)phenyl and 4-(2-methoxyphenyl)phenyl.

The compounds of formula I can be prepared from compounds of formula II. Compounds of formula II can be prepared, for example, as described in Scheme I below. The reagents and starting materials are readily available to one of ordinary skill in the art. All the substituents, unless otherwise specified are previously defined.

Scheme I

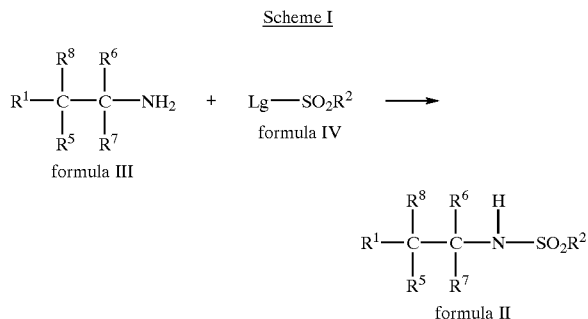

formula III formula IV formula II

In Scheme I, the compound of formula III is reacted with the compound of formula IV under standard conditions well known in the art to provide the compound of formula II. The leaving atom or group represented by Lg may be, for example, a halogen atom such as a chlorine or bromine atom. The reaction is conveniently performed in the presence of a base, for example an alkali metal hydroxide, such as sodium hydroxide, an alkali metal carbonate such as potassium carbonate, or a tertiary amine such as triethylamine or 1,8-diazabicyclo[5.4.0]undec-7-ene. Suitable solvents include halogenated hydrocarbons such as dichloromethane. The reaction is conveniently performed at a temperature in the range of from −20 to 100° C., preferably from −5 to 50° C.

In addition, the compounds of formula II in which $R^1$ represents a 4-bromophenyl group may conveniently be converted into other compounds of formula II in which R represents another 4-substituted phenyl group by reaction with an appropriate boronic acid derivative, for example, a benzeneboronic acid derivative. The reaction is conveniently performed in the presence of a tetrakis (triarylphosphine)palladium(0) catalyst, such as tetrakis (triphenylphosphine)palladium(0) and a base such as potassium carbonate. Convenient solvents for the reaction include aromatic hydrocarbons, such as toluene. The temperature at which the reaction is conducted is conveniently in the range of from 0 to 150° C., preferably 75 to 120° C. Bis aromatic intermediates useful in the preparation of compounds of formula II may be prepared by reacting a bromoaromatic or bromoheteroaromatic compound with an aromatic or heteroaromatic boronic acid in an analogous manner.

The boronic acid derivative used as a starting material may be prepared by reacting a trialkyl borate, such as triisopropyl borate with an appropriate organolithium compound at reduced temperature. For example, 2-fluorobenzeneboronic acid may be prepared by reacting 2-fluorobromobenzene with butyllithium in tetrahydrofuran at about −78° C. to afford 2-fluorophenyl lithium, and then reacting this organolithium compound with triisopropyl borate.

Alternatively, the compounds of formula II in which $R^1$ represents a 4-bromophenyl group may be converted to a 4-(trimethylstannyl)phenyl or 4-(tri-n-butylstannyl)phenyl group by treatment of the corresponding bromide with a palladium(0) catalyst, such as tetrakis(triphenylphosphine)-palladium(0) and hexaalkyldistannane, where the alkyl group is methyl or n-butyl, in an aprotic solvent such as toluene in the presence of a tertiary amine base such as triethylamine, at temperatures ranging from 80 to 140° C., preferably from 90 to 110° C.

The compounds of formula II in which $R^1$ represents a 4-(tri-n-butylstannyl)phenyl group may then be reacted with an aryl- or heteroarylbromide, such as 2-bromothiophene-5-carboxaldehyde, in the presence of a palladium(0) catalyst, such as tetrakis(triphenylphosphine)palladium(0), or a palladium(II) catalyst, such as bis(triphenylphosphine)-palladium(II) dichloride, in an aprotic solvent, such as dioxane, at temperatures ranging from 80 to 140° C., preferably from 90 to 110° C., to afford the corresponding 4-(aryl)phenyl or 4-(heteroaryl)phenyl substituted compound.

The compounds of formula II in which $R^1$ represents a 4-bromophenyl group may be converted into other compounds of formula II in which $R^1$ represents a 4-substituted alkyl- or cycloalkylphenyl group, such as 4-cyclopentylphenyl by treatment of the corresponding bromide with an appropriate alkyl- or cycloalkyl Grignard reagent, such as cyclopentyl-magnesium bromide, in the presence of a palladium(II) catalyst, such as [1,1'-bis (diphenylphosphino)ferrocene]-dichloropalladium(II) ($PdCl_2(dppf)$), in an aprotic solvent, such as diethyl ether at temperatures ranging from −78° C. to 25° C.

The compounds of formula II in which $R^1$ represents a 4-bromophenyl group may be converted into a 4-substituted carboxyaldehydephenyl(formylphenyl) group by reaction of the corresponding bromide with the carbon monoxide gas which is bubbled into the reaction under atmospheric pressure in the presence of a palladium(II) catalyst, such as bis(triphenylphosphine)palladium(II) dichloride and sodium formate in an aprotic solvent, such as dimethylformamide at temperatures ranging from 70 to 110° C., preferably at 90° C.

The compounds of formula II in which $R^1$ represents a 4-hydroxyphenyl group may be converted into other compounds of formula I in which $R^1$ represents an alkoxy group by treatment of the corresponding hydroxyphenyl group with an appropriate alkylhalide such as benzylbromide in the presence of sodium hydride in an aprotic solvent such as dimethylformamide at temperatures ranging from 25 to 100° C., preferably from 50 to 90° C.

The compounds of formula III are known or may be prepared by conventional methods, for example by reducing a corresponding amide or nitrile using borane.

Some of the nitriles or amides used as starting materials may conveniently be prepared by treatment of an acetonitrile of formula $R^1CH_2CN$, for example a substituted phenylacetonitrile such as 4-methoxyphenylacetonitrile or an acetate of formula $R^1CH_2COOR$ (where R is, for example alkyl), for example a phenylacetate such as methyl 4-tert-butylphenylacetate, with a strong lithium amide base, such as sodium or lithium bis(trimethylsilyl)amide, and an alkylhalide, such as methyl iodide, in an aprotic solvent, such as tetrahydrofuran, at a temperature ranging from −78 to 25° C. The esters are converted to amides by hydrolysis (water, alcohol and sodium or potassium hydroxide) to the acid, conversion of the acid to the acid chloride ($SOCl_2$ or $(COCl)_2$ plus DMF (1 drop)) then conversion to the amide with aqueous ammonia and a co-solvent such as tetrahydrofuran or dioxane.

Certain nitriles used to prepare compounds of formula III may also conveniently be prepared by reacting a corresponding ketone derivative, for example a compound of formula $R^1COR^8$, such as (2-acetyl-5-thien-3-yl)thiophene, with tosylmethylisocyanide and potassium t-butoxide in dimethyl ether.

Compounds of formula I can be prepared as described in Scheme II below. The reagents and starting materials are readily available to one of ordinary skill in the art. All the substituents, unless otherwise specified are previously defined.

Scheme II

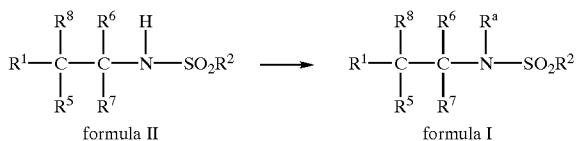

In Scheme II, the compound of formula II is converted to the compound of formula I under conditions well known in the art. For example, standard conditions recognized by one of ordinary skill in the art are described by T. W. Green, "Protective Groups in Organic Synthesis," John Wiley & Sons (1981) pages 223–264. For example, the compound of formula II is dissolved in a suitable organic solvent, such as acetonitrile and treated with a catalytic amount of dimethylaminopyridine (DMAP). The solution is treated with an equivalent of an anhydride of structure (1) or chloroformate of structure (2);

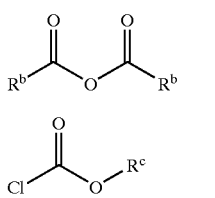

wherein $R^b$ represents (1–6C)alkyl, aryl, (1–6C)alkylaryl, (1–6C)alkylNH(1–6C)alkyl, (1–6C)alkylN(1–6C)alkyl$_2$, and (1–6C)alkylNR$^e$R$^f$ wherein R$^e$ and R$^f$ together with the nitrogen atom to which they are attached form an azetidinyl, pyrrolidinyl, piperidinyl, morpholino, piperazinyl, hexahydroazepinyl or octahydroazocinyl group, and R$^c$ represents (1–6C)alkyl, aryl, or (1–6C)alkylaryl. Examples of anhydrides (1) include but are not limited to acetic anhydride, propionic anhydride, butyric anhydride, trimethylacetic anhydride, isobutyric anhydride, valeric anhydride, hexanoic anhydride, benzoic anhydride, 4-anisic anhydride, o-toluic anhydride, m-toluic anhydride, p-chlorobenzoic anhydride, 4-bromobenzoic anhydride, 1-naphthylacetic anhydride, and the like. Examples of chloroformates (2) include but are not limited to methyl chloroformate, ethyl chloroformate, propyl chloroformate, butyl chloroformate, isobutyl chloroformate, pentyl chloroformate, hexyl chloroformate, benzyl chloroformate, phenyl chloroformate, 4-chlorophenyl chloroformate, 4-nitrophenyl chloroformate, 2-nitrophenyl chloroformate, 4-nitrobenzyl chloroformate, p-tolyl chloroformate, 4-bromophenyl chloroformate, 4-fluorophenyl chloroformate, 4-methylphenyl chloroformate, 2-naphthyl chloroformate, (((N,N-dimethyl)amino)ethyl)chloroformate, morpholino ethylchloroformate, and the like. The reaction mixture is stirred at a temperature of about –78° C. to about 100° C. for about one hour to about 48 hours and the product is then isolated and purified using standard isolation and purification techniques. For example, the reaction is concentrated under vacuum, diluted with a suitable organic solvent, such as ethyl acetate, rinsed with saturated sodium bicarbonate, water, brine, dried over anhydrous magnesium sulfate, filtered and concentrated under vacuum. The crude product can then be purified by flash chromatography on silica gel with a suitable eluent, such as ethyl acetate/hexane to provide the purified compound of formula I.

By way of further example, an equivalent of pivaloyloxymethyl iodide or pivaloyloxymethyl chloride is combined with the compound of formula II in a suitable organic solvent, such as acetonitrile in the presence of an equivalent of a suitable base, such as potassium carbonate. The reaction is stirred at a temperature of about 0° C. to room temperature for 2 to 6 hours. The product is then isolated and purified by techniques well known in the art, such as extraction techniques and chromatography.

Alternatively, in Scheme II, the compound of formula II is alkylated under standard conditions well known in the art with a compound of structure (3);

wherein Hal represents Cl, Br or I, and $R^d$ represents (1–6C)alkyl. For example, the compound of formula II is dissolved in a suitable organic solvent, such as tetrahydrofuran and treated with an equivalent of a suitable base, such as sodium bis(trimethylsilyl)amide. The reaction mixture is then treated with about 1.0 to about 1.1 equivalents of compound (3), such as iodomethane. The reaction is stirred at a temperature of about 0° C. to about 100° C. for about one hour to about 48 hours. The product is then isolated by procedures well known in the art, such as extraction techniques and chromatography. For example, the reaction is diluted with a suitable organic solvent, such as ethyl acetate, washed with water, dried over anhydrous magnesium sulfate, filtered and concentrated under vacuum. The crude product is then purified by flash chromatography on silica gel with a suitable eluent, such as ethyl acetate/hexane to provide the purified compound of formula I.

It further understood by one of ordinary skill in the art that the reaction sequence of placing the $R^a$ group on the sulfonamide nitrogen in the last step, may be modified by placing the $R^a$ group on the sulfonamide nitrogen following the reaction described in Scheme I and prior to the previously described further derivatization of formula II, such as when $R^1$ represents a 4-bromophenyl group.

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK cells stably expressing human GluR4B (obtained as described in European Patent Application Publication Number EP-A1-583917) are prepared. The tissue culture medium in the wells is then discarded, and the wells are each washed once with 200 µl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 µM Fluo3-AM dye (obtained from Molecular Probes Inc., Eugene, Oreg.) in buffer in each well. After the incubation, each well is washed once with 100 μl buffer, 200 μl of buffer is added and the plates are incubated for 30 minutes.

Solutions for use in the test are also prepared as follows. 30 μM, 10 μM, 3 μM and 1 μM dilutions of test compound are prepared using buffer from a 10 mM solution of test compound in DMSO. 100 μM cyclothiazide solution is prepared by adding 3 μl of 100 mM cyclothiazide to 3 ml of buffer. Control buffer solution is prepared by adding 1.5 μl DMSO to 498.5 μl of buffer.

Each test is then performed as follows. 200 μl of control buffer in each well is discarded and replaced with 45 μl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 μl of buffer and 45 μl of test compound in buffer in appropriate wells. A second fluorescent reading is taken after 5 minutes incubation. 15 μl of 400 μM glutamate solution is then added to each well (final glutamate concentration 100 μM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 μM cyclothiazide.

In another test, HEK293 cells stably expressing human GluR4 (obtained as described in European Patent Application Publication No. EP-A1-0583917) are used in the electro-physiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N 1-[2-ethanesulfonic acid]) 10 EGTA (ethylene-bis (oxyethylene-nitrilo)tetraacetic acid), pH=7.2 with CsOH, 295 mOsm kg-1. With these solutions, recording pipettes have a resistance of 2–3 MΩ. Using the whole-cell voltage clamp technique (Hamill et al.(1981)Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM, they produce a greater than 30% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifylng and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|  | Quantify (mg/capsule) |
| --- | --- |
| Active Ingredient | 250 |
| Starch, dried | 200 |
| Magnesium Stearate | 10 |
| Total | 460 |

The above ingredients are mixed and filled into hard gelatin capsules in 460 mg quantities.

Formulation 2

Tablets each containing 60 mg of active ingredient are made as follows:

|  | Quantity (mg/tablet) |
| --- | --- |
| Active Ingredient | 60 |
| Starch | 45 |
| Microcrystalline Cellulose | 35 |

-continued

| | Quantity (mg/tablet) |
|---|---|
| Polyvinylpyrrolidone | 4 |
| Sodium Carboxymethyl Starch | 4.5 |
| Magnesium Stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

As used herein the term "patient" refers to a mammal, such as a mouse, guinea pig, rat, dog or human. It is understood that the preferred patient is a human.

As used herein the term "effective amount" refers to the amount or dose of the compound which provides the desired effect in the patient under diagnosis or treatment.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The following examples represent typical syntheses of starting materials for the compounds of formula I, and of compounds of formula I as described generally above. These examples are illustrative only and are not intended to limit the invention in any way. The reagents and starting materials are readily available to one of ordinary skill in the art. As used herein, the following terms have the meanings indicated: "Eq" refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to methyl sulfoxide; "EtOAc" refers to ethyl acetate; and "LDA" refers to lithium diisopropylamide.

Preparation 1

2-(4-Bromophenyl)Propionitrile

A solution of 50.0 g (225.0 mmol) of 4-bromophenylacetonitrile and 1.8 g (12.8 mmol) of potassium carbonate in 387 mL of dimethyl carbonate was heated to 180° C. in a sealed vessel for 16 hours. The solution was then cooled, diluted with 200 ml of ethyl acetate and washed once with 100 ml water, once with 100 ml of 10% aqueous sodium bisulfate and once with 100 ml brine. The organic portion was dried ($MgSO_4$), filtered and concentrated in vacuo. The residue was distilled under vacuum through a short path distillation apparatus to afford 40.3 g (85%) of the title compound.

Preparation 2

2-(4-Bromophenyl)propylamine hydrochloride

To a solution of 35.2 g (167.6 mmol) of material from Preparation 1 under reflux in 35.0 mL of tetrahydrofuran was added 18.4 ml (184.3 mmol) of 10M borane-dimethylsulfide slowly via a syringe. The solution was heated under reflux for an additional 1 hour after the addition was complete. The solution was cooled to ambient temperature and a saturated solution of hydrogen chloride in methanol was added slowly until pH 2 was achieved. The resulting slurry was concentrated in vacuo. The residue was dissolved in methanol and concentrated in vacuo twice. The resulting solid was suspended in ethyl ether, filtered, rinsed with ethyl ether and dried in vacuo to afford 31.2 g (74%) of the title compound.

Preparation 3

2-Fluorobenzeneboronic Acid

A solution of 50 g (285.6 mmol) of 2-fluorobromobenzene in 400 mL of tetrahydrofuran was cooled to −78° C. and 200 mL (320.0 mmol) of 1.6M n-Butyllithium was added via a cannula. The mixture was stirred at −78° C. for 60 minutes, then 98.9 mL (428.4 mmol) of triisopropyl borate was added via a cannula and stirring was continued for 60 minutes. The cooling bath was removed and the mixture was stirred at ambient temperature for 1.5 hours, then 150 mL of 6N hydrochloric acid was added and stirring was continued for 1.5 hours. To the mixture was added 100 mL of brine, and then the organic layer was separated and the aqueous layer was extracted three times with 30 mL each of ether. The combined organic extracts were dried ($MgSO_4$), filtered and concentrated in vacuo. The residue was recrystallized from water to afford 25.2 g (63%) of the title compound.

Preparation 4

2-(4-bromophenyl)-N-(t-butoxycarbonyl) propylamine

To a solution of 11.8 g (55.0 mmol) of material from Preparation 2 in 100 mL of chloroform and 100 mL of saturated sodium bicarbonate was added 12.0 g (55.0 mmol) of di-tert-butyl dicarbonate. The solution was stirred at ambient temperature for 1 hour. The organic layer was separated and the aqueous layer was extracted three times with 30 mL each of chloroform. The combined organic extracts were dried ($MgSO_4$), filtered and concentrated in vacuo to afford 16.5 g (95%) of the title compound.

Preparation 5

2-(4-(2-fluorophenyl)phenyl)-N-(t-butoxycarbonyl) propylamine

To a degassed solution of 12.5 g (39.8 mmol) of material from Preparation 4, 6.7 g (47.7 mmol) of material from Preparation 3 and 8.2 g (59.7 mmol) of potassium carbonate in 140 mL of toluene was added 2.3 g (1.9 mmol) of tetrakis (triphenylphosphine)palladium(0). The mixture was heated at 90° C. for 18 hours. The mixture was then cooled to ambient temperature and 300 mL of water and 150 mL of ether were added. The organic layer was separated and the aqueous layer was extracted three times with 50 mL each of ethyl acetate. The combined organic extracts were dried (MgSO$_4$), filtered and concentrated in vacuo. Chromatography (500 g of silica gel, 10% ethyl acetate/hexane) of the residue afforded 9.3 g (71%) of the title compound.

Preparation 6

2-(4-(2-fluorophenyl)phenyl)propylamine

A solution of 9.3 g of material from Preparation 5 in 100 mL 20% trifluoroacetic acid/dichloromethane was stirred at ambient temperature for 2 hours. The mixture was concentrated in vacuo to afford 11.7 g of material. The material was dissolved in 100 mL of ether and washed twice with 50 mL of 1N sodium hydroxide. The organic layer was concentrated in vacuo to afford 5.48 g (85%) of the title compound.

Preparation 7

2-(4-Isopropylphenyl)propionitrile

In a 250 ml flask, 4-isopropylphenylacetonitrile 8.00 g (50.2 mmol) was dissolved in tetrahydrofuran (150 ml) under a nitrogen atmosphere. The solution was cooled to −78° C. and lithium bis(trimethylsilyl)amide (1M in tetrahydrofuran, 52.8 ml (52.8 mmol) added. The resulting mixture was stirred at −78° C. for 1 hour. To this reaction mixture was added iodomethane 3.29 ml (52.8 mmol). The resulting mixture was slowly allowed to warm to ambient temperature over 16 hours then quenched with 0.2M hydrochloric acid and extracted twice with diethyl ether. The organic fractions were combined, dried (MgSO$_4$) and concentrated under vacuo. Chromatography (SiO$_2$, 20% ethyl acetate/hexanes) gave 6.32 g (73%) of the title compound.

Field Desorption Mass Spectrum: M=173.

Analysis for $C_{12}H_{15}N$: Theory: C, 83.19; H, 8.73; N, 8.08. Found: C, 82.93; H, 8.57, N, 8.02.

Preparation 8

2-(4-Isopropylphenyl)propylamine hydrochloride

In a 100 ml flask, fitted with a condenser, 2-(4-isopropylphenyl) propionitrile 1.90 g (11.0 mmol) was dissolved in tetrahydrofuran (70 ml) under a nitrogen atmosphere. Borane-methyl sulfide complex (10.0–10.2 M in tetrahydrofuran, 1.20 ml, 12.1 mmol) was added to the solution and the mixture heated to reflux for 3 hours. The solution was cooled to ambient temperature and a saturated solution of hydrochloric acid in methanol added slowly until a white precipitate formed. The solvent was removed in vacuo and the resulting white solid triturated (×4) with diethyl ether. Drying under vacuo gave 1.76 g (73%) of the title compound.

Preparation 9

2-(4-Methoxyphenyl)propionitrile

Following the method of Preparation 7, but using 4-methoxyphenylacetonitrile 5.00 g (34.0 mmol), 6.32 g of the title compound was obtained.

Field Desorption Mass Spectrum: M=161.

Analysis for $C_{10}H_{11}NO$: Theory: C, 74.51; H, 6.88; N, 8.69. Found: C, 74.34; H, 6.67; N, 8.93.

Preparation 10

2-(4-Methoxyphenyl)propylamine hydrochloride

Following the method of Preparation 8, but using the product of Preparation 9, 2.75 g (17.1 mmol), 2.77 g (81%) of the title compound was obtained.

Analysis for $C_{10}H_{16}ClNO$: Theory: C, 59.55; H, 8.00; N, 6.94. Found: C, 59.33; H, 7.89; N, 6.71.

Preparation 11

Methyl 2-(4-t-butylphenyl)propanoate 23.3 mL of lithium bis(trimethylsilyl)amide (1.0 M, 23 mmols) was added dropwise to 4.75 g (23 mmols) of methyl 4-tert-butylphenylacetate in 100 mL of dry THF at −78° C. while stirring under nitrogen. The mixture was stirred at this temperature for 45 minutes, then 1.5 mL (24 mmol) methyl iodide was added dropwise and the solution was stirred for an additional 1 hour at −78° C. The mixture was poured into 200 mL of H$_2$O and the desired product was extracted with 500 mL diethyl ether. The organic layer was backwashed once with 500 mL H$_2$O, dried over K$_2$CO$_3$, and concentrated under reduced pressure to yield 5.12 of a dark oil. The oil was purified via silica gel chromatography eluting with a solvent gradient of hexane to hexane/ethyl acetate 19:1. The fractions containing the desired product were combined and concentrated under reduced pressure to yield the title compound 2.65 g (53%).

Mass Spectrum: M=220.

Preparation 12

Methyl 2-(4-t-butylphenyl)butanoate 4 g (19 mmol) of methyl 4-tert-butylphenylacetate, 19.5 mL (1.0 M, 19 mmol) of lithium bis(trimethylsilyl)amide and 3.12 g (20 mmol) of ethyl iodide were reacted as described in Preparation 11 to yield 5.13 g of a brown oil. Chromatography, eluting with a gradient solvent of hexane to hexane/ethyl acetate 19:1 gave the title compound 2.35 g (53%).

Mass Spectrum: M=234.

Preparation 13

Methyl 2-(4-t-butylphenyl)-2-methylpropanoate 4.75 g (23 mmol) of methyl 4-tert-butylphenylacetate, 46.6 mL (1.0 M, 46 mmol) of lithium bis(trimethylsilyl) amide, and 6.80 g (48 mmols) of methyl iodide were reacted as described in Preparation 11 to yield 4.73 g of a crude oil. Chromatography, eluting with a solvent gradient of hexane to hexane/ethyl acetate 19:1, gave the title compound 2.0 g (37%).

Mass Spectrum: M=234.

Preparation 14

Ethyl 2-(2-naphthyl)propanoate 5 g (23 mmol) of ethyl 2-naphthylacetate, 23.3 mL (1.0 M, 23 mmol) of lithium bis(trimethylsilyl)amide, and 1.5 mL (2 4 mmol) of methyl iodide were reacted as described in Preparation 11 to yield 5.71 g of a dark oil. Chromatography eluting with a solvent gradient of hexane to hexane/ethyl acetate 19:1 gave the title compound 2.85 g (54%).

Mass Spectrum: M=228.

Preparation 15

2-(4-t-butylphenyl)propanoic Acid 2.60 g (12 mmol) of the product of Preparation 11 and 1.75 g (42 mMol) of lithium hydroxide were placed into a tri-solvent solution of tetrahydrofuran (189 mL), $CH_3OH$ (63 mL), and $H_2O$ (63 mL) and stirred at ambient temperature for 16 hours. The mixture was then concentrated under reduced pressure and the resulting white solid was taken into 200 mL 1N HCl and the desired product was extracted with 250 mL ethyl acetate. The organic layer was concentrated under reduced pressure to give the title compound 1.21 g (49%).

Mass Spectrum: M=206.

Preparation 16

2-(4-t-butylphenyl)butanoic Acid

The title compound (2.14 g) was prepared by the method of Preparation 15, starting from the product of Preparation 12, and recrystallized from hexane.

Mass Spectrum: M=220.

Preparation 17

2-(4-t-butylphenyl)-2-methylpropanoic Acid

The title compound (1.75 g) was prepared by the method of Preparation 15 starting from the product of Preparation 13, and recrystallized from hexane.

Mass Spectrum: M=220.

Preparation 18

2-(2-Naphthyl)propanoic Acid

The title compound (3.81 g) was prepared by the method of Preparation 15 starting from the product of Preparation 14, and recrystallized from hexane/ethyl acetate 9:1.

Mass Spectrum: M=214.

Preparation 19

2-(4-t-butylphenyl)propionamide 900 mg (4.4 mmol) of the product of Preparation 15 was added portionwise to oxalyl chloride (10 mL) at ambient temperature under $N_2$ followed by $CH_2Cl_2$ (10 mL). Initiation of the reaction was accomplished by the addition of one drop of DMF. An evolution of gas appeared and the reaction was stirred at ambient temperature for 2 hours. The solution was concentrated under reduced pressure to yield an oil. Dioxane (10 mL) was added for solubility and while stirring at ambient temperature, 28% ammonium hydroxide (10 mL) was added and the reaction was stirred for 16 hours. The solution was then concentrated under reduced pressure to yield a white solid. This solid was taken into 50 mL ethyl acetate, backwashed once with 50 mL $H_2O$, dried over $K_2CO_3$, and concentrated under reduced pressure to yield 770 mg of a solid. Recrystallization from hexane/ethyl acetate 1:1 gave the title compound 555 mg (61%).

Mass Spectrum: M=205.

Preparation 20

2-(4-t-butylphenyl)butanamide

The title compound was prepared by the method of Preparation 19, starting from the product of Preparation 16. Purification was achieved by silica gel chromatography (Chromatotron-2000 micron rotor) eluting with a solvent of hexane/ethyl acetate 1:1 to yield 471 mg (60%).

Mass Spectrum: M=219.

Preparation 21

2-(4-t-butylphenyl)-2-methlypronpionamide

The title compound was prepared following the method of Preparation 19, starting from the product of Preparation 17. The crude product was triturated with a solution of hexane/ethyl acetate 19:1 for ½ hour and filtered to yield 1.16 g of a white solid. Subsequent recrystallization from ethyl acetate/ethanol 1:1 gave an 80% recovery as platelets.

Mass Spectrum: M=219.

Preparation 22

2-(2-Naphthyl)propionamide

The title compound was prepared following the method of Preparation 19, starting from the product of Preparation 18. Recrystallization from hexane/ethyl acetate 1:1 yielded 1.65 g (90%).

Mass Spectrum: M=199.

Preparation 23

2-(4-t-butylphenyl)propylamine 25 mL of Borane-tetrahydrofuran complex (1.0 M, 0.025 Mol) was added via a syringe to 1.10 g (5.4 mmol) of the product of Preparation 19 (60 mL) at ambient temperature under $N_2$. The mixture was then heated at 60°–65° C. for 16 hours. A saturated HCl/methanol solution (5 mL) was then added via a syringe at ambient temperature with severe foaming and the solution was then concentrated under reduced pressure. The resulting white solid was taken into 100 mL 1 N NaOH and the liberated free amine was extracted once with 200 ml diethyl ether. The organic layer was backwashed once with 200 mL $H_2O$, dried over $K_2CO_3$, and concentrated under reduced pressure to yield 1.21 g of a brown oil. Chromatography (Chromatotron-2000 micron rotor) eluting with a gradient solvent of ethyl acetate/MeOH 9:1 to MeOH gave 856 mg (83%).

Mass Spectrum: M=191.

Preparation 24

2-(4-t-butylphenyl)butylamine

The title compound 540 mg was prepared as an oil by the method of Preparation 23, starting from the product of Preparation 20.

Mass Spectrum: M=205.

Preparation 25

2-(4-t-butylphenyl)-2-methylpropylamine

The title compound 428 mg (42%) was prepared following the method of Preparation 23, starting from the product of Preparation 21, and using methanol as the chromatography solvent.

Mass Spectrum: M=205.

Preparation 26

2-(2-Naphthyl)propylamine

The title compound, 450 mg (44%) was prepared as an oil following the method of Preparation 23, starting from the product of Preparation 22, and using methanol as the chromatography solvent.

Mass Spectrum: M=185.

Preparation 27

Methyl 1-(4-t-butylphenyl)cyclopropanecarboxylate 4 g (19.4 mmol) of Methyl 4-tert-butylphenylacetate, 39 mL (1.0 m, 2 Eq.) of lithium bis(trimethylsilyl)amide, and 3 g (2 Eq.) of 1-bromo-2-chloroethane in 100 mL dry THF were reacted as described in Preparation 11, except that the reaction mixture was stirred for one hour at ambient temperature before work-up. This reaction yielded 4.21 g of a brown oil. This material was purified via silica gel chromatography eluting with a gradient solvent of hexane to hexane/EtOAc 19:1 to yield the title compound 1.57 g (35%) as a pale yellow solid m.p. 58°–60° C. Calculated for $C_{15}H_{20}O_2$: Theory: C, 77.37; H, 8.81 Found: C, 77.54; H, 8.68.

Preparation 28

1-(4-t-butylphenyl)cyclopropanecarboxylic acid 1 g (4.3 mmol) of the product of Preparation 27 and 650 mg (15.5 mmol) of lithium hydroxide were placed in a tri-solvent solution of THF (66 mL), methanol (22 mL), and $H_2O$ (22 mL) and reacted as described in Preparation 15 to yield 840 mg of a solid. This material was purified via silica gel chromatography eluting with hexane/EtOAc 1:1 as a solvent to yield the title compound, 600 mg, (64%) as a white solid. m.p. dec>150° C. Calculated for $C_{14}H_{18}O_2$: Theory: C, 77.03; H, 8.31 Found: C, 77.08; H, 8.02.

Preparation 29

1-(4-t-butylphenyl)cyclopropanecarboxamide 580 mg. (2.7 mmol) of the product of Preparation 27, oxalyl chloride (10 mL), methylene chloride (10 mL) and one drop DMF were reacted as described in Preparation 19 to yield 573 mg of the crude acid chloride. Amide conversion was accomplished with 28% ammonium hydroxide (10 mL) and dioxane (10 mL) as described in Preparation 27 to yield 590 mg of a solid. Trituration in hexane/EtOAc. 19:1 and subsequent filtration yielded 510 mg (87%) of the title compound as a white solid. m.p. 178°–180° C. Calculated for $C_{14}H_{19}NO$: Theory: C, 77.38; H, 8.81; N, 6.45 Found: C, 77.53; H, 8.77; N, 6.39.

Preparation 30

1-(4-t-butylphenyl)cyclopropylmethylamine 7 mL of Borane-tetrahydrofuran complex (1.0 M, 7 mmol) and 500 mg (2.3 mmol) of the product of Preparation 29 in THF (50 mL) were reacted as described in Preparation 23 to yield 510 mg of an oil. Purification was achieved via silica gel chromatography eluting with a gradient solvent of EtOAc/methanol 9:1 to methanol to yield 222 mg (47%) as a solid, m.p. 39°–41° C. Calculated for $C_{14}H_{21}N$: Theory C, 82.70; H, 10.41; N, 6.89 Found: C, 81.36; H, 10.13; N, 7.24.

Preparation 31

2-(4-Bromophenyl)propylamine hydrochloride

To a −15° C. solution of 50.0 g (251.2 mmol) of 4-bromo-acetophenone and 49.0 g (251.2 mmol) of tosylmethyl iso-cyanide in 800 mL of dry dimethoxyethane was added a hot solution of 50.7 g (452.2 mmol) of potassium tert-butoxide in 230 mL of tert-butyl alcohol dropwise at a rate to maintain the temperature below 0° C. The reaction was stirred at −5° C. for 45 min after addition was complete. The cooling bath was removed and the reaction stirred for 2.5 h more. The mixture was concentrated in vacuo to a volume of 200 mL and diluted with 500 mL of water. The aqueous mixture was extracted four times with diethyl ether, and the combined organic portions were dried ($MgSO_4$), filtered and concentrated in vacuo. The residue was dissolved in 55 mL of tetrahydrofuran and heated to reflux. To the refluxing solution was added slowly dropwise 27.6 mL (276.3 mmol) of 10.0 M borane-dimethylsulfide complex. Refluxing was continued for 20 min after addition was complete. The mixture was cooled to ambient temperature and methanol saturated with hydrogen chloride was added very slowly until pH 2 was achieved. The mixture was concentrated in vacuo and the residue was dissolved in methanol and concentrated in vacuo again. The solid residue was suspended in 125 mL of ethanol, filtered, rinsed with ethanol then diethyl ether. The white solid was dried in vacuo to afford 25.4 g (40%) of the title compound. The filtrate was concentrated in vacuo and suspended in diethyl ether. The solid was filtered, rinsed with diethyl ether and dried in vacuo to afford another 15.6 g (25%) of the title compound.

Preparation 32

2-(4-Methylphenyl)propionitrile

The title compound was prepared from 4-methylphenyl-acetonitrile as described in Preparation 7.

Analysis for $C_{10}H_{11}N$: Theory: C, 82.72; H, 7.64; N, 9.65. Found: C, 82.75; H, 7.42; N, 9.94.

Preparation 33

2-(4-Methylphenyl)propylamine hydrochloride

The title compound was prepared from the product of Preparation 32 as described in Preparation 8.

Field Desorption Mass Spectrum: M=150 (M-HCl)

Preparation 34

2-(4-Benzyloxyphenyl)propionitrile

4-Hydroxyphenylacetonitrile (15.3 g, 114.9 mmol) was dissolved in dimethylformamide (120 ml) and to this was added potassium carbonate (23.78 g, 172.4 mmol), benzyl bromide (20.64 g, 120.6 mmol) and potassium iodide (3.81 g, 30.0 mmol). The solution was stirred at ambient temperature for 6 hours after which water was added. 4-Benzyloxyphenyl-acetonitrile precipitated out of solution. The suspension was filtered and the precipitate washed with water (3×). Yield 24.8 g (97%) as yellow crystals. The title product was prepared from 4-benzyloxyphenyl-acetonitrile as described in Preparation 7. Yield 76%.

Field Desorption Mass Spectrum: M=237.2.

Analysis for $C_{16}H_{15}NO$: Theory: C, 80.98; H, 6.37; N, 5.90. Found: C, 80.93; H, 6.46; N, 6.11.

Preparation 35

2-(4-Benzyloxyphenyl)propylamine hydrochloride

The title compound was prepared from the product of Preparation 34 as described in Preparation 2.

Analysis for $C_{16}H_{20}ClNO$: Theory: C, 59.55; H, 8.00; N, 6.94. Found: C, 59.33; H, 7.89; N, 6.71.

Preparation 36

N-t-butoxycarbonyl-N-(2-(4-hydroxyphenyl)propyl) 2-propanesulfonamide

The product of Example 40 (7.6 g, 23.8 mmol) was dissolved in dichloromethane (100 ml) and to this mixture was added di-tert-butyl dicarbonate (5.71 g, 26.2 mmol) and 4-dimethylaminopyridine (1.45 g, 11.9 mmol). The reaction was stirred at ambient temperature for 1 hour. The reaction was washed with a saturated aqueous solution of sodium hydrogen sulfate and brine. The organic fraction was dried over magnesium sulfate and concentrated under vacuo. The protected sulfonamide (9.00 g, 21.0 mmol) was dissolved in ethyl acetate: $H_2O$ (5:1) and ammonium formate (2.0 g, 31.5 mmol) added to the mixture. Then palladium on carbon (10%) (0.9 g) was added to the reaction and this was stirred at ambient temperature for 6 hours. The suspension was filtered through celite and the resulting solution concentrated in vacuo to give 5.51 g (78%) of title product.

Field Desorption Mass Spectrum: M=329.1.

Analysis for $C_{15}H_{23}NO_5S$: Theory: C, 54.69; H, 7.04; N, 4.25. Found: C, 53.70; H, 7.72; N, 4.04.

Preparation 37

2-(4-bromophenyl)-1-nitro-1-methylethylene

A solution of 30.0 g (162 mmol) of 4-bromobenzaldehyde, 116 mL (1.6 mole) of nitroethane, and 37.5 g (486 mmol) of ammonium acetate in 200 mL of toluene was heated under a Dean and Stark trap for 18 hours. The mixture was then cooled to 80° C., 1 mL of concentrated sulfuric acid was added, and the mixture was stirred at 80° C. for 2 hours. The mixture was then cooled to ambient temperature and washed with 200 mL of brine. The organic layer was separated and the aqueous layer was extracted three times with 60 mL of diethyl ether. The combined organics were dried ($MgSO_4$), filtered and concentrated in vacuo. The residue was recrystallized from methanol to afford 18.7 g (47%) of the title compound.

Preparation 38

2-(4-bromophenyl)-1-nitro-1-methylethane

A suspension of 1.3 g (33.9 mmol) of lithium aluminum hydride in 55 mL of tetrahydrofuran (THF) was cooled to 0° C. A solution of 4.1 g (16.9 mmol) of material from Preparation 37 in 5 mL of THF was added dropwise. 1.3 mL of water, 1.3 mL of 1M sodium hydroxide and 4.0 mL of water were added in sequence. The mixture was filtered through celite and rinsed with dichloromethane. The organics were concentrated in vacuo to afford 3.0 g of the title compound (83%).

Preparation 39

N-2-(4-bromophenyl)propyl 2-proanesulfonamide

A solution of 15.0 g (59.9 mmol) of the material from Preparation 31 and 18.4 mL (131.8 mmol) of triethylamine in 150 mL of dichloromethane was stirred 20 min at room temperature, then cooled to 0° C. and treated dropwise over 5 min with 8.1 mL (71.9 mmol) of 2-propylsulfonyl chloride in 10 mL of dichloromethane. After stirring overnight at room temperature, the reaction was washed once with 200 mL of 10% aqueous sodium bisulfate, the layers separated and the aqueous layer extracted twice with 100 mL each of dichloromethane. The combined organic extracts were dried ($MgSO_4$), filtered and concentrated in vacuo. Chromatography (500 g of silica gel, 30% ethyl acetate/ hexane) of the residue afforded 11.0 g (57%) of the title compound.

Preparation 40

N-2-(4-tri-n-butylstannylphenyl)popyl 2-propanesulfonamide

To a degassed solution of 4.8 g (15.1 mmol) of material from Preparation 39, 2.1 mL (15.1 mmol) of triethylamine and 8.0 mL (15.9 mmol) of hexabutyiditin in 35 mL of toluene add 0.9 g (0.8 mmol) of tetrakis (triphenylphosphine) palladium (0). The mixture was heated to 100° C. for 16 hours, cooled to room temperature and diluted with 35 mL of ethyl acetate. The mixture was washed with 50 mL of 10% aqueous sodium bisulfate, the organic layer was separated and the aqueous layer was extracted two times with 50 mL each of ethyl acetate. The combined organics were dried ($MgSO_4$), filtered and concentrated in vacuo. Chromatography (350 g of silica gel, 20% ethyl acetate/hexane) of the residue afforded 3.5 g (44%) of the title compound as a clear, colorless oil.

Analysis calculated for $C_{24}H_{45}NO_2SSn$: %C, 54.35; %H, 8.55; %N, 2.64. Found: %C, 54.41; %H, 8.16; %N, 2.74.

Mass Spectrum: M=530.

Preparation 41

2-(4-bromophenyl)-N-(t-butoxycarbonyl)ethylamine

To a room temperature solution of 10.0 g (50.0 mmol) of 4-bromophenethylamine and 11.0 g (50.0 mmol) of di-tert-butyl dicarbonate in 100 mL of chloroform was added 100 mL of saturated aqueous sodium bicarbonate. The mixture was stirred at room temperature for 1.5 hours and diluted with 100 mL of water. The organic layer was separated and the aqueous layer was extracted two times with 100 mL each of chloroform. The combined organics were washed once with 100 mL of 10% aqueous sodium bisulfate, dried ($NaSO_4$), filtered and concentrated in vacuo to afford 14.6 g (97%).

Mass Spectrum: M+1=301.

Preparation 42

4-cyanophenylboronic acid

A solution of 10.0 g (54.9 mmol) of 4-bromobenzonitrile in 100 mL of tetrahydrofuran was cooled to −85° C. whereupon 36.0 mL (57.6 mmol) of 1.6 M solution of n-butyllithium in hexane was added. The mixture was stirred for five minutes and 19.0 mL (82.4 mmol) of triisopropylborate was added. The mixture was stirred at −85° C. for 30 minutes then warmed to ambient temperature over one hour. To the mixture was added 35 mL of 5 N hydrochloric acid and stirring was continued for 2.5 hours. The mixture was diluted with 100 mL of saturated aqueous sodium chloride and extracted three times with 100 mL each of ethyl ether. The combined organics were dried ($MgSO_4$), filtered and concentrated in vacuo. The residue was recrystallized from water and filtered to afford 2.0 g (25%) of the title compound.

Preparation 43

N-2-(4-formylphenyl)propyl 2-propanesulfonamide

A solution of 4.6 g (14.5 mmol) of material from Preparation 39 in 50 mL of tetrahydrofuran was cooled to −85° C.

and 19 mL (30.5 mmol) of 1.6M n-Butyllithium was added via syringe. The mixture was stirred at −85° C. for 30 min then 2.2 mL (29.0 mmol)of N,N-dimethylformamide was added via syringe and stirring was continued for 30 min. The mixture was stirred at 0° C. for 30 min and then 100 mL of brine and 50 mL of ether was added. The organic layer was separated and the aqueous layer was extracted three times with 20 mL each of ether. The combined organic extracts were dried (MgSO$_4$), filtered and concentrated in vacuo. Chromatography (200 g of silica gel, 40% ethyl acetate/hexane) of the residue afforded 2.2 g (56%) of the title compound.

Preparation 44

N-2-(4-(4-(1-hydroxy-2-(N-(t-butoxycarbonyl)-methylsulfonamido) ethyl)phenyl)phenyl)propyl 2-propanesulfonamide A. N-(t-butoxycarbonyl)methanesulfonamide: To a solution of 15.0 g (157.7 mmol) of methanesulfonamide, 17.6 g (173.5 mmol) of triethylamine and 1.9 g (15.8 mmol) of 4-dimethylaminopyridine in 200 mL of dichloromethane was added of 37.9 g (173.5 mmol) of di-t-butyldicarbonate in 200 mL of dichloromethane over ten minutes. The mixture was stirred at ambient temperature for 2.25 hours and concentrated in vacuo. The residue was dissolved in 250 mL of ethyl acetate and washed once with 200 mL of 1 N hydrochloric acid, once with 100 mL of water and once with 100 mL of saturated aqueous sodium chloride. The organic layer was dried (MgSO$_4$), filtered and concentrated in vacuo. The residue was suspended in 100 mL of hexane, filtered and dried in vacuo to afford 26.1 g (85%) of the title compound.

Analysis calculated for C$_7$H$_{13}$NO$_4$S: %C, 36.91; %H, 6.71; %N, 7.17. Found: %C, 36.97; %H, 6.79; %N, 7.04.

Mass Spectrum: M+1=196.

B. N-(4-bromophenyl)carbonylmethyl-N-t-butoxycarbonyl methane-sulfonamide: A solution of 1.0 g (5.1 mmol) of material from Step A, 1.4 g (5.1 mmol) of 2,4'-dibromoacetophenone and 0.8 g (5.6 mmol) of potassium carbonate in 25 mL of acetonitrile was stirred at ambient temperature for two hours. The mixture was diluted with 25 mL of ethyl acetate and washed once with 15 mL of water. The organic layer was separated and the aqueous layer was extracted three times with 10 mL each of ethyl acetate. The combined organics were dried (MgSO$_4$), filtered and concentrated in vacuo. Chromatography (50 g of silica gel, 20% ethyl acetate/hexane) of the residue afforded 1.5 g (76%) of the title compound.

Analysis calculated for C$_{14}$H$_{17}$NBrO$_5$S: %C, 42.87; %H, 4.63; %N, 3.57. Found: %C, 43.11; %H, 4.66; %N, 3.37.

Mass Spectrum: M−1=391.

C. N-[2-(4-Bromophenyl)2-hydroxyethyl]-N-(t-butoxycarbonyl) methane-sulfonamide: To a solution of 2.6 g (6.7 mmol) of material from Step B in 25 mL of ethanol was added 0.3 g (6.7 mmol) of sodium borohydride and the mixture was stirred for 16 hours. The mixture was concentrated in vacuo and the residue was partitioned between 25 mL of ethyl acetate and 25 mL of water. The organic layer was separated and the aqueous layer was extracted three times with 10 mL each of ethyl acetate. The combined organics were dried (MgSO$_4$), filtered and concentrated in vacuo to afford 2.6 g (98%) of the title compound.

Analysis calculated for C$_{14}$H$_{19}$NBrO$_5$S: %C, 42.65; %H, 5.11; %N, 3.55. Found: %C, 42.60; %H, 5.08; %N, 3.46.

Mass Spectrum: M=394.

D. To a degassed solution of 0.6 g (1.5 mmol) of material from Step C and 0.8 g (1.5 mmol) of material from Preparation 40 in 5 mL of toluene was added 0.08 g (0.07 mmol) of tetrakis(triphenylphosphine)palladium (0). The mixture was heated to reflux for 16 hours, cooled to ambient temperature and diluted with 10 mL of ethyl acetate. The mixture was washed once with 8 mL of saturated aqueous potassium fluoride, the organic layer was separated and the aqueous layer was extracted four times with 5 mL each of ethyl acetate. The combined organics were dried (MgSO$_4$), filtered and concentrated in vacuo. Chromatography (50 g of silica gel, 50% ethyl acetate/hexane) of the residue afforded 0.3 g (32%) of the title compound.

Analysis calculated for C$_{26}$H$_{38}$N$_2$O$_7$S$_2$. 0.05 CHCl$_3$: %C, 55.80; %H, 6.84; %N, 5.00. Found: %C, 55.47; %H, 6.93; %N, 4.72.

Mass Spectrum: M=554.

Preparation 45

Dibromoformaldoxime

A solution of 150 g (1.6 mole) of glyoxylic acid and 142 g (2.0 mole)of hydroxylamine hydrochloride in 1200 mL of water was stirred for 2 days. To the mixture was added slowly 342 g (4.1 mole) of sodium bicarbonate and 1000 mL of dichloromethane. The mixture was cooled to 0° C. and a solution of 147 mL (2.8 mole) bromine in 700 mL of dichloromethane was added dropwise. The mixture was stirred at ambient temperature for 18 h. The organic layer was separated and the aqueous layer was extracted three times with 300 mL each of dichloromethane. The combined organic extracts were dried (MgSO$_4$), filtered and concentrated in vacuo to afforded 93.1 g (28%) of the title compound.

Preparation 46

2-trimethylstannylthiazole

A. To a −78° C. solution of 5.0 g (58.7 mmol) of thiazole in 120 mL of tetrahydrofuran was added of 36.7 mL (58.7 mmol) of a 1.6 M solution of n-butyllithium in hexane. The mixture was stirred for 20 minutes whereupon 11.7 g (58.7 mmol) in 15 mL of tetrahydrofuran was added dropwise over 15 minutes. The cooling bath was removed and the mixture was stirred for two hours. The mixture was diluted with 100 mL of water and extracted three times with 100 mL ethyl ether. The combined organics were dried (MgSO$_4$), filtered and concentrated in vacuo. The residue was dissolved in 50 mL of ethyl ether, filtered through silica gel and concentrated in vacuo to afford 3.6 g (24%) of the title compound.

Preparation 47

N-2-(4-bromophenyl)ethyl 2-propanesulfonamide

To a solution of 10.0 g (50 mmol) of 4-bromophenethylamine and 7.6 mL (55 mmol) of triethylamine in 150 mL of dichloromethane was added a solution of 6.2 mL (55 mmol) of isopropylsulfonyl chloride in 40 mL of dichloromethane dropwise. The mixture was stirred at room temperature for 18 h. The mixture was washed with 100 mL of 1N aqueous hydrochloric acid, the organic layer was separated and the aqueous layer extracted one time with 100 mL each of dichloromethane. The combined organics were dried (Na$_2$SO$_4$), filtered and concentrated in vacuo to afford 6.7 g (44%) of the title compound.

Preparation 48

N-2-(4-(tri-n-butylstannyl)phenyl)ethyl 2-propanesulfonamide

To a solution of 5.0 g (16.3 mmol) of material from Preparation 47, 9.9 g (17.1 mmol) of bis-tri-n-butylstannyl and 2.3 mL (16.3 mmol) of triethylamine in 55 mL of toluene was added 0.9 g (0.8 mmol) of tetrakis(triphenylphosphine) palladium(0). The mixture was heated at 100° C. for 18 h. The mixture was cooled to room temperature and 55 mL of was 10% aqueous sodium bisulfate added. The organic layer was separated and the aqueous layer was extracted two times with 20 mL each of ether. The combined organic extracts were dried ($MgSO_4$), filtered and concentrated in vacuo. Chromatography (400 g of silica gel, 25% ethyl acetate/hexane) of the residue afforded 3.5 g (42%) of the title compound.

Preparation 49

4-(4-Bromophenyl)-1,1-dioxotetrahydro-1,2-thiazine

A. Ethyl 4-bromophenylacetate: A solution of 25.0 g (116.3 mmol) of 4-bromophenylacetic acid, 24.1 g (174.4 mmol) of potassium carbonate and 10.2 mL (127.9 mmol) of iodoethane in 250 mL of acetonitrile was heated at 70° C. for 16 hours. The mixture was cooled to ambient temperature, diluted with 200 mL of ethyl acetate and washed once with 200 mL of saturated aqueous sodium bicarbonate. The organic layer was separated and the aqueous layer was extracted three times with 75 mL each of ethyl acetate. The combined organics were dried ($MgSO_4$), filtered and concentrated in vacuo to afford 16.2 g (57%) of the title compound.

B. Phenyl 3-carbethoxy-3-(4-bromophenyl)propylsulfonate: A solution of 16.2 g (66.6 mmol) of material from Step A, 4.6 g (33.3 mmol) of potassium carbonate and 4.4 g (16.7 mmol) of 18-crown-6 in 130 mL of toluene was heated to 90° C. and 6.1 g (33.3 mmol) of phenyl vinylsulfonate in 35 mL of toluene was added dropwise over one hour. The mixture was heated for 16 hours, cooled to ambient temperature and diluted with 100 mL of ethyl acetate. The mixture was washed once with 100 mL of half saturated brine. The organic layer was separated and the aqueous layer was extracted once with 50 mL of ethyl acetate. The combined organics were dried ($MgSO_4$), filtered and concentrated in vacuo. Chromatography (Waters 2000, 15% ethyl acetate/hexane) of the residue affords 4.8 g (17%) of the title compound.

Analysis calculated for $C_{18}H_{19}O_5SBr$: %C, 50.59; %H, 4.48. Found: %C, 50.61; %H, 4.47.

Mass Spectrum: M+1=428.

C. Phenyl 3-carboxy-3-(4-bromophenyl)propylsulfonate: To a solution of 4.8 g (11.3 mmol) of material from Step B in 40 mL of methanol was added 6.8 mL of 2 N aqueous sodium hydroxide. The mixture was stirred at ambient temperature for 5 hours and concentrated in vacuo. The residue was dissolved in 50 mL of water and extracted three times with 20 mL each of ethyl ether. The aqueous layer is acidified to pH 2 with 10% aqueous sodium bisulfate and extracted four times with 20 mL each of ethyl acetate. The combined ethyl acetate layers were dried ($MgSO_4$), filtered and concentrated in vacuo to afford 4.1 g (91%) of the title compound.

Analysis calculated for $C_{16}H_{15}O_5SBr$: %C, 48.13; %H, 3.79. Found: %C, 48.17; %H, 3.53.

Mass Spectrum: M=399.

D. Phenyl 3-carboxamido-3-(4-bromophenyl)propylsulfonate: To a 0° C. solution of 4.1 g (10.2 mmol) of material from Step C and 2.0 mL (14.3 mmol) of triethylamine in 23 mL of tetrahydrofuran was added 1.9 mL (14.3 mmol) of isobutyl chloroformate. The mixture was stirred at 0° C. for 25 minutes whereupon 11.2 mL (22.4 mmol) of a 2 N solution of ammonia in methanol was added. The cooling bath was removed and the mixture stirred for 16 hours. The mixture was diluted with 50 mL of ethyl acetate and washed once with 50 mL of water. The organic layer was separated and the aqueous layer was extracted three times with 25 mL each of ethyl acetate. The combined organics were dried ($MgSO_4$), filtered and concentrated in vacuo. Chromatography (250 g silica gel, 35% acetone/hexane) of the residue affords 1.7 g (44%) of the title compound.

Mass Spectrum: M=398.

E. 4-(4-Bromophenyl)-1,1,3-trioxotetrahydro-1,2-thiazine: To a 0° C. solution of 9.0 mL (9.0 mmol) of a 1.0 M tetrahydrofuran solution of potassium tert-butoxide in 15 mL of tetrahydrofuran was added a solution of 1.7 g (4.5 mmol) of material from Step D in 14 mL of tetrahydrofuran dropwise over 30 minutes. After stirring at 0° C. for two hours, the cooling bath was removed and stirring continued for 30 minutes. The mixture was diluted with 25 mL of water and extracted two times with 10 mL each of ethyl ether. The aqueous portion was acidified to pH 2 with 10% aqueous sodium bisulfate and extracted four times with 20 mL each of ethyl acetate. The combined ethyl acetate layers were dried ($MgSO_4$), filtered and concentrated in vacuo. Chromatography (75 g silica gel, 0.25% acetic acid/40% acetone/hexane) of the residue affords 0.2 g (17%) of the title compound.

Analysis calculated for $C_{10}H_{10}NO_3SBr$: %C, 39.49; %H, 3.31; %N, 4.61. Found: %C, 39.74; %H, 3.23; %N, 4.42.

Mass Spectrum: M=304.

F. To a suspension of 0.13 g (0.4 mmol) of material from Step E and 0.2 g (4.9 mmol) of sodium borohydride in 3 mL of dioxane was added 0.4 mL (4.9 mmol) of trifluoroacetic acid slowly via syringe. After stirring at ambient temperature for 30 minutes the mixture was heated to reflux for 5 hours. The mixture was cooled to ambient temperature, diluted with 3 mL of methanol and stirred for 16 hours. The mixture was removed and stirring continued for 30 minutes. The mixture was concentrated in vacuo, dissolved in 10 mL of ethyl acetate and washed two times with 5 mL each of 1 N hydrochloric acid and once with 5 mL of 20% saturated aqueous sodium bicarbonate/brine. The organics were dried ($MgSO_4$), filtered and concentrated in vacuo to afford 0.1 g (89%) of the title compound.

Analysis calculated for $C_{10}H_{12}NO_3SBr$: %C, 41.39; %H, 4.17; %N, 4.83. Found: %C, 41.10; %H, 4.34; %N, 4.76.

Mass Spectrum: M−1=289.

Preparation 50

D,L-penicillamine methyl ester hydrochloride

Through a suspension of 10.0 g (67.0 mmol) of D,L-penicillamine in 200 mL of methanol was bubbled hydrogen chloride for 5 minutes. The mixture was refluxed for 16 hours, cooled to ambient temperature and concentrated in vacuo The residue was suspended in ethyl ether, filtered and dried to afford 12.6 g (94%) of the title compound.

Mass Spectrum: M=163.

Preparation 51

N-(t-butoxycarbonyl)-4-tributylstannylaniline

A. N-(t-Butoxycarbonyl)-4-bromoaniline: To a solution of 6.0 g (39.4 mmol) of 4-bromoaniline in 30 mL of tetrahydrofuran was added 69.8 mL (69.8 mmol) of a 1.0 M solution of sodium bis(trimethylsilyl)amide in tetrahydrofuran. To the mixture was added 7.6 g (34.9 mmol) of di-t-butyldicarbonate in 10 mL of tetrahydrofuran. The mixture was stirred at ambient temperature for one hour and concentrated in vacuo. The residue was dissolved in 50 mL of ethyl acetate and washed once with 50 mL of 10% aqueous sodium bisulfate. The organic layer was separated and the aqueous layer was extracted two times with 25 mL each of ethyl acetate. The combined organics were dried ($MgSO_4$), filtered and concentrated in vacuo. Chromatography (250 g of silica gel, 10% ethyl acetate/hexane) of the residue afforded 5.0 g (53%) of the title compound.

Analysis calculated for $C_{11}H_{14}NO_2Br$: %C, 48.55; %H, 5.19; %N, 5.15. Found: %C, 48.81; %H, 5.29; %N, 4.95. Mass Spectrum: M−1=271.

B. A degassed solution of 4.9 g (18.0 mmol) of material from Step A, 2.6 mL (18.9 mmol) of triethylamine, 9.6 mL (18.9 mmol) of bis(tributyltin) and 1.0 g (0.9 mmol) of tetrakis(triphenylphosphine)palladium(0) in 45 mL of toluene was heated to 100° C. for 5 hours. The mixture was cooled to ambient temperature and diluted with 40 mL of ethyl acetate. The mixture was washed once with 50 mL of 10% aqueous sodium bisulfate, the organics separated and the aqueous layer extracted three times with 20 mL each of ethyl acetate. The combined organics were dried ($MgSO_4$), filtered and concentrated in vacuo. Chromatography (400 g of silica gel, 5% ethyl acetate/hexane) of the residue afforded 1.4 g (16%) of the title compound. Mass Spectrum: M+1=483.

Preparation 52

N-2-(4-tri-n-butylstannylphenyl)propyl methanesulfonamide

The title compound (3.6 g) was prepared by the method of Preparation 40 starting from the product of Example 1.

Preparation 53

N-2-(4-(3-thienyl)phenyl)propyl amine

A. 2-(3-thienyl)phenyl-N-(t-butoxycarbonyl)propyl amine: To a solution of 0.7 g (2.2 mmol) of material from Preparation 4, 0.3 g (2.4 mmol) thiophene-3-boronic acid and 0.46 g (3.3 mmol) of potassium carbonate in 5 mL of dioxane and 1 mL of water was added 0.025 g (0.11 mmol) of palladium(II)acetate and 0.058 g (0.22 mmol) triphenylphosphine. The mixture was heated at 100° C. for 18 h. The mixture was cooled to room temperature and 5 mL of brine was added. The organic layer was separated and dried ($MgSO_4$), filtered and concentrated in vacuc. Chromatography (25 g of silica gel, 25% ethyl acetate/hexane) of the residue afforded 0.44 g (60%) of the title compound.

B. A solution of 0.4 g (1.3 mmol) of material from Preparation 53A in 4 mL of dichloromethane and 1 mL of trifluoroacetic acid was stirred at ambient temperature for 3 h. The mixture was concentrated in vacuo and the residue was dissolved in 5 mL ethyl acetate and 5 mL saturated sodium bicarbonate. The organic layer was separated and the aqueous layer extracted three times with 5 mL of ethyl acetate. The combined organics were dried ($MgSO_4$), filtered and concentrated in vacuo to afford 0.21 g (74%) of the title compound.

Preparation 54A 4-(N,N-dibenzylamino)phenylacetonitrile

A solution of 4-aminophenylacetonitrile (20 g, 151.3 mmol) in dry DMF (150 ml) was treated with potassium carbonate (50.1 g, 363.1 mmol), benzyl bromide (54.4 g, 318 mmol), and potassium iodide (5 g, 0.2 30.3 mmol). The reaction mixture was stirred at room temperature for 12 h. Water (100 ml) was added to the mixture and the organic was extracted with ether (3×200 ml). The combined organic fraction was washed with brine (200 ml), dried over sodium sulfate and concentrated. The crude product was further purified by flash chromatography ($SiO_2$, 20% EtOAc: Hexanes) to give 36.2 g (76%) of the pure product. NMR was consistent with the proposed title structure. Field Desorption Mass Spectrum: $M^+$=312.

Preparation 54B 1-chloroprop-2-yl sulfonyl chloride

To a 0° C. saturated solution of chlorine in 100 mL of water was added dropwise 15.7 mL (200 mmol) of propylene sulfide while chlorine was bubbled through the mixture. The mixture was stirred at 0° C. for one hour after addition. The resulting oil was separated and the aqueous portion was extracted two times with 20 mL each of dichloromethane. The combined organics were dried ($CaCl_2$), filtered and concentrated in vacuo. Vacuum distillation afforded 10.8 g (30%) of the title compound.

Field Desorption Mass Spectrum: M−1=176.

Preparation 55

2-(4-(N,N-dibenzylamino)phenyl)propionitrile

A −78° C. solution of the material from Preparation 54A (22.8 g, 73 mmol) in dry THF (70 ml) was treated with lithium bis(trimethylsilyl)amide (1M in THF, 76.6 ml, 76.6 mmol). The resulting mixture was stirred at −78° C. for 1 h. Methyl iodide (4.8 ml, 76.6 mmol) was added to the mixture. The reaction mixture was stirred at −78 ° C. for 1 h and gradually was allowed to warm to room temperature over 12 h. Hydrochloric acid (0.2 M, 100 ml) was added to the mixture and the organic was extracted with ether (3×200 ml). The combined organic fraction was washed with water (3×200 ml), brine (200 ml), dried over sodium sulfate and concentrated. The crude product was further purified by flash chromatography ($SiO_2$, 20% EtOAc: Hexane) to give 22.6 g (95%) of the pure product. NMR was consistent with the proposed title structure. Field Desorption Mass Spectrum: $M^+$=326.

Preparation 56

2-(4-(N,N-dibenzylamino)phenyl)propylamine hydrochloride

A 0° C. solution of the material from Preparation 55 (23.6 g, 72.3 mmol) in dry THF (100 ml) was treated with borane methylsulfide (10 M in THF, 8 ml, 80 mmol). The reaction mixture was stirred while refluxing for 3 h. The solution was cooled down to room temperature and was treated with a saturated solution of hydrochloric acid in methanol until a white precipitate formed. The solvent was removed in vacuo and the resulting white solid was triturated with ether (4×100 ml). The desired hydrochloric salt was dried under vacuo to give 28.2 g (97%) of the pure product which was used in next step without any further purification. NMR was consistent with the proposed title structure.

Preparation 57

N-2-(4-(N',N'-dibenzylamino)phenyl)propyl 2-propanesulfonamide

A 0° C. suspension of the material from Preparation 56 (15.2 g, 37.7 mmol) in dichloromethane (125 ml) was treated with triethylamine (11.4 g, 113 mmol) followed by 2-propylsulfonyl chloride (9.2 g, 56.5 mmol). The reaction mixture was stirred at 0° C. for 1 h and at room temperature for 6 h. The reaction was stopped by the addition of water (100 ml). Organic was extracted with dichloromethane (3×200 ml). The combined organic fraction was washed with hydrochloric acid (0.2 M 100 ml), water (3×200 ml), brine (100 ml), dried over sodium sulfate, and concentrated in vacuo to give the crude material which was further purified by flash chromatography (SiO$_2$, 30% EtOAc: Hexane) to give 10.32 g (63%) of the title compound. NMR was consistent with the proposed title structure. Field Desorption Mass Spectrum: M$^+$=436.

Preparation 58

N-2-(4-aminophenyl)propyl 2-proranesulfonamide

A solution of the product from Preparation 57 (2.5 g, 5.72 mmol) in EtOH (30 ml) was treated with ammonium formate (0.4 g, 6.3 mmol) and palladium on carbon (0.25 g, 10 mole %). The reaction mixture was stirred at room temperature for 6 h. The mixture was filtered through a celite cake and the filtrate was concentrated in vacuo to give 1.36 g of the pure product (93%). NMR was consistent with the proposed title structure. Field Desorption Mass Spectrum: M$^+$=257.

Preparation 59

N-t-butyloxycarbonyl-N-2-(4-(N',N'-dibenzylamino) phenyl)propyl 2-propanesulfonamide A solution of the material from Preparation 57 (2.5 g, 5.72 mmol) in dry dichloromethane (25 ml) was treated with di-t-butyl dicarbonate (1.47 g, 6.3 mmol) and 4-dimethylaminopyridine (0.37 g, 2.8 mmol). The reaction mixture was stirred at room temperature for 1 h. The reaction was stopped by the addition of water (20 ml). Organic was extracted with ether (3×30 ml). The combined organic fraction was washed with a 20% solution of sodium hydrogensulfate (2×30 ml), water (3×100 ml), brine (30 ml), dried over sodium sulfate, and concentrated in vacuo to give the crude material which was further purified by flash chromatography (SiO$_2$, 30% EtOAc: Hexane) to give 3.07 g (100%) of the title compound. NMR was consistent with the proposed title structure. Field Desorption Mass Spectrum: M$^+$=XXX.

Preparation 60

N-t-butyloxycarbonyl-N-2-(4-aminophenyl)propyl 2-propanesulfonamide

A solution of the product from Preparation 59 (3.07 g, 5.72 mmol) in EtOH (30 ml) was treated with ammonium formate (0.54 g, 8.6 mmol) and palladium on carbon (0.3 g, 10 mole %). The reaction mixture was stirred at room temperature for 6 h. The mixture was filtered through a celite cake and the filtrate was concentrated in vacuo to give 1.9 g (93%) of the title compound. NMR was consistent with the proposed title structure. Field Desorption Mass Spectrum: M$^+$=257.

Preparation 61

2-(4-nitrophenyl)propionitrite

A −15° C. solution of 4-nitroacetophenone (16.5 g, 100 mmol) and tosylmethyl isocyanide (29.3 g, 150 mmol) in methoxyethyl ether (400 ml) was slowly treated with a room temperature solution of the potassium t-butoxide (28 g, 250 mmol) in t-butanol (200 ml). The reaction mixture was stirred at −15° C. for 1 h and then allowed to warm to room temperature over night. Water (100 ml) was added to the mixture and organic was extracted with ether (3×200 ml). The combined organic fraction was washed with water (3×200 ml), brine (100 ml), dried over sodium sulfate, and concentrated in vacuo to give the crude material which was further purified by flash chromatography (SiO$_2$, 30% EtOAc: Hexane) to give 13.6 g (77%) of the title compound. NMR was consistent with the proposed title structure. Field Desorption Mass Spectrum: M$^+$=225.

Preparation 62

2-(4-nitrophenyl)propylamine

A 0° C. solution of the material from Preparation 61 (11.8 g, 67 mmol) in dry THF (200 ml) was treated with borane tetrahydrofuran (1 M in THF, 72 ml, 72 mmol). The reaction mixture was stirred at room temperature for 16 h. A solution of THF:MeOH (1:1, 10 ml) and sodium hydroxide (5 N, 40 ml) were added to the reaction mixture stepwise and the mixture was refluxed for 5 h. The reaction mixture was allowed to cool to room temperature. Organic was extracted with dichloromethane (3×100 ml). The combined organic fraction was washed with water (3×200 ml), brine (100 ml), dried over potassium carbonate, and concentrated in vacuo to give the crude material which was further purified by flash chromatography (SiO$_2$, 5% MeOH: CH$_2$Cl$_2$) to give 8.5 g (71%) of the pure product. NMR was consistent with the proposed title structure. Field Desorption Mass Spectrum: M$^+$=181.

Preparation 63

N-2-(4-nitrophenyl)propyl 2-propanesulfonamide

A 0° C. suspension of the material from Preparation 62 (8.2 g, 45.3 mmol) in dichloromethane (200 ml) was treated with 1,8-diazabicyclo[5.4.0]undec-ene (7.6 g, 49.8 mmol) followed by 2-propylsulfonyl chloride (12 g, 49.8 mmol). The reaction mixture was stirred at 0° C. for 1 h and at room temperature for extra 12 h. The reaction was stopped by the addition of water (100 ml). Organic was extracted with dichloromethane (3×200 ml). The combined organic fraction was washed with water (3×200 ml), brine (100 ml), dried over potassium carbonate, and concentrated in vacuo to give the crude material which was further purified by flash chromatography (SiO$_2$, 30% EtOAc: Hexane) to give 8.9 g (68%) of the pure product. NMR was consistent with the proposed title structure. Field Desorption Mass Spectrum: M$^+$=287.

Preparation 64

N-2-(4-aminophenyl)propyl 2-propanesulfonamide

A degassed solution of the material from Preparation 63 (8.75 g, 31 mmol) in ethyl acetate (200 ml) was treated with palladium on carbon (4 g, 50 mol %). The mixture was shaken under 60 psi of hydrogen gas for 2 h. The reaction mixture was filtered through a celite cake and the filtrate was concentrated in vacuo to yield 7.44 g (94%) of the pure product. NMR was consistent with the proposed title structure. Field Desorption Mass Spectrum: M$^+$=257.

Preparation 65

N-2-(4-(benzylamino)phenyl)propyl 2-propanesulfonamide

In a pressure tube a degassed solution of bromide from Preparation 39 (3 g, 9.7 mmol) in anhydrous toluene (40 ml)

was treated with benzylamine (1.27 ml, 11.6 mmol),tris (dibenzylideneacetone)dipalladium(0) (170 mg, 0.19 mmol), S(−)-BINAP (360 mg, 0.58 mmol), and sodium t-butoxide (1.95 mg, 20.3 mmol). The reaction mixture was stirred at 80° C. for 16 h. The mixture was cooled to room temperature. Water (5 ml). was added to the mixture and organic was extracted with ether (3×% ml). The combined organic fraction was washed with water (2×5 ml), brine (5 ml), dried over sodium sulfate, and concentrated in vacuo to give the crude product which was further purified by flash chromatography (SiO2, 20% EtOAc: hexanes) to give 1.9 g (58%) of a yellow oil as the title compound. NMR was consistent with the proposed title structure.

Preparation 66

2-(4-aminophenyl)propyl 2-propanesulfonamide

A solution of the product from Preparation 65 (1.5 g, 4.33 mmol) in EtOAc (30 ml) was treated with ammonium formate (0.41 g, 6.5 mmol) and palladium on carbon (0.15 g, 10 mole %). The reaction mixture was stirred at room temperature for 3 h. The mixture was filtered through a celite cake and the filtrate was concentrated in vacuo to give 1.1 g of the title compound (98%). NMR was consistent with the proposed title structure. Field Desorption Mass Spectrum: $M^+=257$.

Preparation 67

N-2-(4-(carboxy)phenyl)propyl 2-propanesulfonamide

A −85° C. solution of the product from Preparation 39 (220 mg, 0.65 mmol) in dry THF (2 ml) was treated with n-butyl lithium solution (0.87 ml, 1.37 mmol, 1.6 M solution). The reaction mixture was stirred for 10 minutes at −85° C. and then carbon dioxide gas was bubbled into the mixture for 1 minutes. The reaction mixture was allowed to warm to room temperature. Water (5 ml) and concentrated hydrochloric acid (3 ml) were added to the mixture and organic was extracted with ether (3×10 ml). The combined organic fractions was washed with water (2×10 ml), brine (5 ml), dried over sodium sulfate, and concentrated in vacuo to yield 210 mg (98%) of the pure product which was used in the next step without further purification.

Preparation 68

N-t-butyloxycarbonyl-4-piperazinoacetophenone

A solution of the 4-piperazinoacetophenone (10 g, 49 mmol) in tetrahydrofuran:water (200 ml, 1:1 mixture) was treated with potassium carbonate (8.43 g, 58 mmol) and di-t-butyl dicarbonate (13.1 g, 53.9 mmol). The reaction mixture was stirred at room temperature for 3 h. Water (300 ml) was added to the mixture and organic was extracted with ethyl acetate (3×100 ml). The combined organic fraction was washed with water (2×200 ml), brine (100 ml), dried over sodium sulfate, and concentrated in vacuo to 17.41 g of the yellowish solid. The crude product was further purified by Prep LC 2000 eluting with 30% EtOAc: Haxanes to give 10.9 g (73%) of the title compound as a white solid. Field Desorption Mass Spectrum: $M^+=305$.

Preparation 69

2-(N-t-butyloxycarbonyl-4-piperazinophenyl) propionitrile

The title compound 1.8 g (16%) was prepared as a solid following the method of Preparation 61, starting from the product of Preparation 68 and using tosylmethyl isocyanide. NMR was consistent with the proposed title structure. Field Desorption Mass Spectrum: $M^+=316$.

Preparation 70

2-(N-t-butyloxycarbonyl-4-piperazinophenyl) propylamine

The title compound 1.78 g (100%) was prepared as a solid following the method of Preparation 62, starting from the product of Preparation 69 and using borane methylsulfide. NMR was consistent with the proposed title structure. Field Desorption Mass Spectrum: $M^+=319$.

Preparation 71

N-2-(N-t-butyloxycarbonyl-4-piperazinophenyl) propyl 2-propanesulfonamide

The title compound 676 mg (61%) was prepared as a solid following the method of Preparation 63, starting from the product of Preparation 70 and using borane methylsulfide. NMR was consistent with the proposed title structure. Field Desorption Mass Spectrum: $M^+=319$.

Preparation 72

N-2-(4-piperazinophenyl)propyl 2-propanesulfonamide

A solution of the material from Preparation of 71 (800 mg, 1.88 mmol) in dichloromethane (10 ml) was treated with trifluoroacetic acid (5 ml). The reaction mixture was stirred at room temperature for 3 h. A 1N solution of the sodium hydroxide (10 ml) was added to the mixture and the organic was extracted with dichloro-methane (3×20 ml). The combined organic fraction was washed with water (2×20 ml), brine (20 ml), dried over potassium carbonate, and concentrated in vacuo to give 560 mg (91%) of the pure product. NMR was consistent with the proposed title structure. Field Desorption Mass Spectrum: $M^+=319$.

Preparation 73

N-2-(N-benzoyl-4-piperazinophenyl)propyl 2-propanesulfonamide

A 0° C. solution of material from Preparation 72 (80 mg, 0.25 mmol) in dichloromethane (10 ml) was treated with triethylamine (28 mg, 0.27 mmol) and benzoic anhydride (61 mg, 0.27 mmol). The reaction mixture was stirred at 0° C. for 30 minutes. Water (5 ml) was added to the mixture and the organic was extracted with dichloromethane (3×5 ml). The combined organic fraction was washed with water (2×5 ml), brine (5 ml), dried over potassium carbonate, and concentrated in vacuo to give 94 mg (87%) of the title compound. NMR was consistent with the proposed title structure. Field Desorption Mass Spectrum: $M^+=430.2$.

Preparation 74

3-Tributyltin-2-cyclopenten-1-one

A −20° C. solution of hexabutylditin (4.6 g, 7.9 mmol) in dry THF (15 ml) was treated with nBuLi (4.9 ml, 7.9 mmol, 1.6 M solution in hexanes). The reaction mixture was stirred at −20° C. for 30 min and then cooled to −78° C. The mixture was treated with 3-ethoxy-2-cyclopenten-1-one (1.0 g, 7.9 mmol) and the reaction mixture stirred at −78° C. for 30 min. A saturated, aqueous solution of ammonium chloride (2 ml) followed by water (30 ml) and the organic extracted with hexanes (2×30 ml). The combined organic layers were washed with brine (20 ml), dried over magnesium sulfate and concentrated in vacuo. This gave 2.7 g (93%) of the crude product which was used without further purification. NMR was consistent with the title structure.

Preparation 75

N-2-(4-(1-(3-oxo)cyclopentenyl)phenyl)prolyl 2-propanesulfonamide

A solution of the product of Preparation 39 (1.0 g, 3.22 mmol) in dry, degassed THF (15 ml) was treated with the product of Preparation 74 (1.8 g, 4.83 mmol), and dichlorobis(triphenylphosphine)palladium(II) (45 mg, 0.06 mmol). The reaction mixture was heated to reflux for 48 h. The mixture was cooled and partitioned between acetonitrile and hexanes. The acetonitrile layer was washed with hexanes (3×20 ml), then concentrated in vacuo. The crude product was further purified by flash chromatography ($SiO_2$, 70% EtOAc: hexanes) to give 0.71 g (68%) of title compound as a pure product. NMR was consistent with proposed title structure. Field Desorption Mass Spectrum: $M^+$=321.1.

Preparation 76

1-(4-bromophenyl)-2,5-dimethylpyrrole

4-Bromoaniline (56.0 g., 0.33 Mol.), 2,5-hexanedione (37.6 g., 0.33 Mol), and acetic acid (5 ml) were placed into Toluene (500 ml) and heated under reflux for 8 hours employing a dean stark trap to remove the water from the reaction. The reaction was cooled to room temperature and concentrated under reduced vacuum. The resulting oil was taken into ethyl acetate, washed one time each with 2N hydrochloric acid, 2N NaOH, and $H_2O$, dried over $Na_2SO_4$, and concentrated under reduced vacuum to yield a brown solid. Material was purified by silica gel flash chromatography eluting with hexane. Concentration of the appropriate fractions yielded 55.0 gm. of a light yellow solid. (68%) NMR was consistent with the proposed title structure. Field Desorption Mass Spectrum: $M^+$ 249 m.p. 71°–73° C.

Preparation 77

1-(4-acetylphenyl)-2,5-dimethylpyrrole

A −30° C. solution of the material from Preparation 76 (25.0 g, 0.1 mol) in dry ether (500 ml) was treated with n-butyllithium (70 ml of 1.6 M, 0.12 mol) and stirred for one hour at −30° C. N,N Dimethyl acetamide (9.7 g, 0.12 mol) was added and the reaction continued at this temperature for 4 hours. The reaction was then allowed to warm to room temperature and stirred over night at this temperature. In the morning, the mixture was diluted with ethyl acetate and the combined organic layers were washed one time each with 2.0 N hydrochloric acid and $H_2O$, dried over $Na_2SO_4$, and concentrated under reduced vacuum to yield a white solid. The material was triturated in hexane and filtered to yield 12.8 gm. of a white solid. m.p. 106°–108° C. (60%) NMR was consistent with the proposed title structure. Field Desorption Mass Spectrum: $M^+$ 214

Preparation 78

1-(4-(1-cyano)ethylphenyl)-2,5-dimethylpyrrole

The starting ketone from Preparation 77 (44.3 g, 0.21 mol), tosylmethyl isocyanide (40.6 g, 0.21 mol), potassium-t-butoxide (39.2 g, 0.35 mol), and t-butyl alcohol (250 ml) were reacted in ethylene glycol dimethyl ether (500 ml) as described in Preparation 61 to yield a yellow solid. Purification was achieved by silica gel flash chromatography eluting with hexane/ethyl acetate 4:1 to yield 32.3 gm. of yellow crystals. m.p. 79°–80° C. (68%) Field desorption Mass Spectrum: $M^+$ 225

Preparation 79

1-(4-(2-(2-cyano)propyl)phenyl)-2,5-dimethylpyrrole

A −78° C. solution of material from Preparation 78 (7.0 g, 32 mmol) in dry tetrahydrofuran (100 ml) was treated with lithium (bis)trimethylsilylamide (40 ml of 1.0M, 1.3 eq.). After stirring 30 minutes at this temperature, methyl iodide (2.6 ml, 1.3 eq.) was added dropwise and the reaction was allowed to warm to room temperature. The mixture was diluted with ether and the combined organic layers were washed once with $H_2O$, dried over $K_2CO_3$, and concentrated under reduced vacuum to yield 7.61 gm. of a yellow solid. Material was purified via silica gel chromatography eluting with a solvent of hexane/ethyl acetate 9:1 to yield 6.30 gm. of a yellow solid. m.p. 135°–137° C. (83%). Field desorption Mass Spectrum: $M^+$+1 239

Preparation 80

1-(4-(2-(3-amino-2-methyl)propyl)phenyl-2,5-dimethylpyrrole

The nitrile from Preparation 79 (6.23 g, 26.2 mmol) in tetrahydrofuran (250 ml) was treated with borane-THF complex (17.1 ml, 1.0 M) as described in Preparation 62 to yield 6.37 gm. of a foam. This material was purified via silica gel chromatography eluting with a gradient solvent of dichloromethane to dichloromethane/methanol 9:1 to yield 4.08 gm. of a white solid. m.p. 95°–97° C. (65%). NMR was consistent with the proposed title structure. Field Desorption Mass Spectrum: $M^+$ 243

Preparation 81

N-2-(4-(2,5-dimethylpyrrole)phenyl)-2-methylpropyl 2-propanesulfonamide

The amine from Preparation 80 (4.0 g, 16.6 mmol) was treated with 1,8-diazabicyclo[5.4.0]undec-ene (3.28 g, 1.3 eq) and 2-propylsulfonyl chloride (3.2 ml, 1.3 eq) in dichloromethane (80 ml) as described in Preparation 63 to yield 6.1 gm. of a yellow oil. This material was purified via silica gel chromatography eluting with an isocratic solvent of hexane/ethyl acetate 4:1 to yield 4.3 gm. of a white solid. m.p. 110°–112° C. (62%). NMR was consistent with the proposed title structure. Field Desorption Mass Spectrum: $M^+$ 349

Preparation 82

N-2-(4-aminophenyl)-2-methylpropyl 2-propanesulfonamide

The sulfonamide from Preparation 81 (2.17 g, 6.3 mmol) was treated with hydroxylamine hydrochloride (2.0 g, 13.8 mmol) and potassium hydroxide (0.96 g, 20.0 mmol) in absolute ethanol (16 ml) and water (6 ml). This mixture was refluxed for 24 hours. The solution was cooled to room temperature and poured into $H_2O$ and the desired product was extracted with ether. The organic layer was backwashed once with H₂O, dried over K₂CO₃ and concentrated under reduced pressure to yield 1.57 gm. as an oil. This material was purified via silica gel chromatography eluting with an isocratic solvent of hexane/ethyl acetate 1:1 to yield 1.41 gm. of a white solid. m.p. 87°–88° C. (84%). NMR was consistent with the proposed title structure. Field Desorption Mass Spectra: M⁺ 271

Preparation 83

N-2-(4-nitrophenyl)propyl N,N-dimethylsulfamide

The nitro-amine from Preparation 62 (1.8 g, 0.01 Mol) was treated with 1,8-diazobicyclo[5.4.0]undec-ene (1.70 g, 1.1 eq) and N,N-dimethylsulfamoyl chloride (2.1 ml, 1.1 eq) in dichloromethane (40 ml) as stated in Preparation 63 to yield 3.60 gm. of a dark oil. This material was purified via silica gel chromatography eluting with a gradient solvent of hexane/ethyl acetate 9:1 to hexane/ethyl acetate 7:3 to yield 1.0 gm. of a white solid. m.p. 79°–81° (50%). Field desorption Mass Spectrum: M⁺ 288

Preparation 84

N-2-(4-aminophenyl)propyl N,N-dimethylsulfamide

The nitro-sulfamide from Preparation 83 (1.0 g, 3.5 mmol) was treated with 5% Pd/C (2.0 g, excess) and hydrogen in ethyl acetate (100 ml) as described in Preparation 64 to yield 820 mg. of a white solid. m.p. 101.5°–103° C. (91%). Field desorption Mass Spectrum: M⁺ 258

Preparation 85

4-Bromophenylacetyl chloride

A solution of 50.0 g (232 mmol) of 4-bromophenylacetic acid in 150 mL of thionyl chloride was stirred at room temperature for 18 h. The mixture was concentrated in vacuo to afford 54 g (100%) of the title compound.

Preparation 86

(R)-(−)-4-Benzyl-3-(4-bromophenylacetyl)-2-oxazolidinone

A solution of 20.0 g (117 mmol) of (R)-(+)-4-benzyl-2-oxazolidinone in 300 mL of tetrahydrofuran was cooled to −78° C. and 73.0 mL (117 mmol) of 1.6M n-Butyllithium was added dropwise. The mixture was stirred 30 min then was slowly added via cannula to a solution of 25 g (107 mmol) of material from Preparation 85 in 150 mL of tetrahydrofuran at −78° C. The mixture was stirred for 1 hr and then 300 mL of 10% aqueous sodium bisulfate was added. The organic layer was separated and the aqueous layer was extracted three times with 100 mL each of ether. The combined organic extracts were dried (MgSO₄), filtered and concentrated in vacuo. Chromatography (750 g of silica gel, 25% ethyl acetate/hexane) of the residue afforded 27.4 g (68%) of the title compound.

Analysis calculated for C₁₈H₁₆BrNO₃: %C, 57.77; %H, 4.31; %N, 3.74. Found: %C, 57.62; %H, 4.21; %N, 3.74.

Field Desorption Mass Spectrum: M=374.

$[\alpha]_D^{20}$=−59.83 (c=1.04, CHCl₃).

Preparation 87

(−)-4R-Benzyl-3-(2R-(4-bromophenyl)propionyl)-2-oxazolidinone

A solution of 48 g (128 mmol) of material from Preparation 86 in 200 mL of tetrahydrofuran was cooled to −78 ° C. and 141 mL (141 mmol) of 1M sodium bis(trimethylsilyl)amide was added dropwise. The mixture was stirred 60 min then a solution of 20 g (141 mmol) of iodomethane in 20 mL of tetrahydrofuran was slowly added. The mixture was stirred for 60 min at −78° C. and then allowed to warm to room temperature for 60 min. To the reaction was added 10% aqueous sodium bisulfate and the organic layer was separated and the aqueous layer was extracted three times with 100 mL each of ether. The combined organic extracts were dried (MgSO₄), filtered and concentrated in vacuo. Chromatography (500 g of silica gel, 25% ethyl acetate/hexane) of the residue afforded 28.7 g (58%) of the title compound.

Analysis calculated for C₁₉H₁₈BrNO₃: %C, 58.78; %H, 4.67; %N, 3.61. Found: %C, 58.81; %H, 4.63; %N, 3.54.

Field Desorption Mass Spectrum: M=388.

$[\alpha]_D^{20}$=−110.4 (c=0.96, CHCl₃).

Preparation 88

(R)-(+)-2-(4-bromophenyl)propanol

A solution of 28.7 g (74 mmol) of material from Preparation 87 in 250 mL of ether was cooled to 0° C. and 74 mL (148 mmol) of 2M lithiumborohydride in tetrahydrofuran was added dropwise. The mixture was stirred for 2 hr then 1N sodium hydroxide was added and the mixture was stirred until both organic and aqueous layers became clear. The organic layer was separated and the aqueous layer was extracted three times with 10 mL each of ethyl acetate. The combined organic extracts were dried (MgSO₄), filtered and concentrated in vacuo. Chromatography (800 g of silica gel, 25% ethyl acetate/hexane) of the residue afforded 12.3 g (79%) of the title compound.

Analysis calculated for C₉H₁₁BrO: %C, 50.26; %H, 5.15. Found: %C, 48.96; %H, 4.91.

Field Desorption Mass Spectrum: M+1=216.

$[\alpha]_D^{20}$=+13.79 (c=1.06, CHCl₃).

Preparation 89

(R)-2-(4-bromophenyl)propyl methanesulfonate

A solution of 12.2 g (56.7 mmol) of material from Preparation 88 and 8.7 mL (62.4 mmol) of triethylamine in 180 mL of dichloromethane was cooled to 0° C. A solution of 4.8 mL (62.4 mmol) of methanesulfonyl chloride in 10 mL of dichloromethane was added dropwise. The ice-bath was removed and the mixture was stirred at room temperature for 2 h. The mixture was washed with 200 mL of 10% aqueous sodium bisulfate, the organic layer was separated and the aqueous layer extracted three times with 60 mL of ether. The combined organics were dried (MgSO₄), filtered and concentrated in vacuo afford 15.9 g (96%) of the title compound.

Preparation 90

(R)-2-(4-bromophenyl)propyl azide

A solution of 15.8 g (54 mmol) of material from Preparation 89 in 180 mL of N,N-dimethylformamide and 7.0 g (108 mmol) sodium azide was heated at 80° C. for 5 h. The mixture was cooled and concentrated in vacuo. The residue was partitioned between 100 mL of water and 100 mL of ether. The organic layer was separated and the aqueous layer was washed three times with 30 mL each of ether. The combined organic extracts were dried (MgSO4), filtered and concentrated in vacuo to afforded 12.13 g (94%) of the title compound.

Preparation 91

(R)-(+)-2-(4-bromophenyl)propyl amine hydrochloride

A solution of 12.2 g (50.4 mmol) of material from Preparation 90 and 14.5 g (55.4 mmol) of triphenylphosphine in 168 mL of tetrahydrofuran and 3.6 mL of water was stirred at room temperature for 18 h. The mixture was diluted with 100 mL of ether and 50 mL of brine. The organic layer was removed and dried (MgSO4), filtered and concentrated in vacuo. The residue was dissolved in 100 mL of ether and to this was added 200 mL of hydrochloric acid saturated ether. Filtration of the resulting solid afforded 11.9 g (94%) of the title compound.

Analysis calculated for $C_9H_{13}BrClN$; %C, 43.14; %H, 5.23; %N, 5.59. Found: %C, 43.44; %H, 5.23; %N, 5.56.

Mass Spectrum: [M-HCl]=214.

$[\alpha]_D^{20}$=+24.06 (c=1.00, $H_2O$).

Preparation 92

(R)-2-(4-bromophenyl)-N-(t-butoxycarbonyl)propyl amine

To a solution of 5.0 g (20.0 mmol) of material from Preparation 91 in 30 mL of chloroform and 30 mL of saturated sodium bicarbonate was added 4.3 g (20.0 mmol) of di-tert-butyl dicarbonate. The solution was stirred at room temperature for 18 h. The organic layer was separated and the aqueous layer was extracted three times with 10 mL each of chloroform. The combined organic extracts were dried ($MgSO_4$), filtered and concentrated in vacuo to afford 6.2 g (100%) of the title compound.

Preparation 93

(S)-(+)-4-Benzyl-3-(4-bromophenylacetyl)-2-oxazolidinone

Following the procedure of Preparation 86 and using (S)-(−)-4-benzyl-2-oxazolidinone instead of (R)-(+)-4-benzyl-2-oxazolidinone afforded 25.3 g (63%) of the title compound.

Analysis calculated for $C_{18}H_{16}BrNO_3$: %C, 57.77; %H, 4.31; %N, 3.74. Found: %C, 57.69; %H, 4.18; %N, 3.82.

Field Desorption Mass Spectrum: M=374.

$[\alpha]_D^{20}$=+59.35 (c=1.04, $CHCl_3$).

Preparation 94

(+)-4-S-Benzyl-3-(2S-(4-bromophenyl)propionyl)-2-oxazolidinone

Following the procedure of Preparation 87 and using material from Preparation 93 instead of material from Preparation 86 afforded 28.9 g (51%) of the title compound.

Analysis calculated for $C_{19}H_{18}BrNO_3$: %C, 58.78; %H, 4.67; %N, 3.61. Found: %C, 59.40; %H, 4.61; %N, 3.64.

Field Desorption Mass Spectrum: M=388.

$[\alpha]_D^{20}$=+114.8 (c=1.01, $CHCl_3$).

Preparation 95

(S)-(−)-2-(4-bromophenyl)propanol

Following the procedure of Preparation 88 and using material from Preparation 94 instead of material from Preparation 87 afforded 12.3 g (79%) of the title compound.

Analysis calculated for $C_9H_{11}BrO$: %C, 50.26; %H, 5.15. Found: %C, 50.38; %H, 5.08.

Field Desorption Mass Spectrum: M+1=216.

$[\alpha]_D^{20}$=−13.25 (c=1.06, $CHCl_3$).

Preparation 96

(S)-2-(4-bromophenyl)propyl methanesulfonate

Following the procedure of Preparation 89 and using material from Preparation 95 instead of material from Preparation 88 afforded 16.9 g (100%) of the title compound.

Preparation 97

(S)-2-(4-bromophenyl)propyl azide

Following the procedure of Preparation 90 and using material from Preparation 96 instead of material from Preparation 89 afforded 13.0 g (94%) of the title compound.

Preparation 98

(S)-(−)-2-(4-bromophenyl)propyl amine hydrochloride

Following the procedure of Preparation 91 and using material from Preparation 97 instead of material from Preparation 90 afforded 11.6 g (86%) of the title compound.

Analysis calculated for $C_9H_{13}BrClN$: %C, 43.14; %H, 5.23; %N, 5.59. Found: %C, 43.36; %H, 5.39; %N, 5.64.

Mass Spectrum: [M-HCl]=214.

$[\alpha]_D^{20}$=−25.3 (c=1.02, $H_2O$).

Preparation 99

(S)-2-(4-bromophenyl)-N-(t-butoxycarbonyl)propyl amine

Following the procedure of Preparation 92 and using material from Preparation 98 instead of material from Preparation 91 afforded 5.9 g (94%) of the title compound.

Preparation 100

(R)-2-(4-(3-thienyl)phenyl)-N-(t-butoxycarbonyl) propyl amine

To a solution of 2.0 g (6.4 mmol) of material from Preparation 92, 0.9 g (7.0 mmol) of thiophene-3-boronic acid and 1.3 g (9.6 mmol) of potassium carbonate in 20 mL of dioxane and 5 mL of water was added 0.4 g (0.32 mmol) of tetrakis (triphenylphosphine)palladium(0). The mixture was heated at 100° C. for 18 h. The mixture was cooled to room temperature and 20 mL of water and 20 mL of ether was added. The organic layer was separated and the aqueous layer was extracted three times with 10 mL each of ether. The combined organic extracts were dried ($MgSO_4$), filtered and concentrated in vacuo. Chromatography (150 g of silica gel, 15% ethyl acetate/hexane) of the residue afforded 1.4 g (70%) of the title compound.

Preparation 101

(S)-2-(4-(3-thienyl)phenyl)-N-(t-butoxycarbonyl) propyl amine

Following the procedure of Preparation 100 and using material from Preparation 99 instead of material form Preparation 92 afforded 5.9 g (94%) of the title compound.

Preparation 102

2R-(4-(3-thienyl)phenyl)propyl amine

A solution of 1.4 g of material from Preparation 100 in 15 mL 25% trifluoroacetic acid/dichloromethane was stirred at room temperature for 3 h. The mixture was concentrated in vacuo and the residue was dissolved in 20 mL of 1N sodium hydroxide and 20 mL of ethyl acetate. The organic layer was separated and the aqueous layer was extracted four times with 10 mL each of ethyl acetate. The combined organic extracts were dried (MgSO$_4$), filtered and concentrated in vacuo to afford 0.85 g (89%) of the title compound.

Preparation 103

2S-(4-(3-thienyl)phenyl)propyl amine

Following the procedure of Preparation 102 and using material from Preparation 101 instead of material from Preparation 100 afforded 0.9 g (94%) of the title compound.

EXAMPLE 1

N-2-(4-Bromophenyl)propyl methanesulfonamide

To a solution of 2.8 g (11.3 mmol) of material from Preparation 2 at ambient temperature in 30 mL of dichloromethane and 30 mL of 10% aqueous sodium hydroxide was added 1.1 mL (13.6 mmol) of methanesulfonyl chloride. After 1 hour an additional 1.1 mL (13.6 mmol) of methanesulfonyl chloride was added and stirring continued for 1.5 hours. The organic portion was separated and the aqueous portion was extracted twice with 25 mL each of dichloromethane. The combined organics were washed once with 25 mL of 10% aqueous sodium bisulfate, dried (Na$_2$SO$_4$), filtered and concentrated in vacuo to afford 2.7 g (81%) of the title compound.

Analysis calculated for $C_{10}H_{14}NBrO_2S$: %C, 41.11; %H, 4.83; %N, 4.79. Found: %C, 40.92; %H, 4.78; %N, 4.85.

Field Desorption Mass Spectrum: M−1=291

EXAMPLE 2

N-2-(4-(3-fluorophenyl)phenyl)propyl methanesulfonamide

To a degassed solution of 1.5 g (5.1 mmol) of material from Example 1, 1.1 g (7.7 mmol) of 3-fluorobenzeneboronic acid and 1.1 g (7.7 mmol) of potassium carbonate in 30 mL of toluene was added 0.2 g (0.3 mmol) of bis(triphenylphosphine)palladium(II) dichloride. The mixture was heated to 100° C. for 16 hours, cooled to ambient temperature and diluted with 20 mL of ethyl acetate. The mixture was washed once with 25 mL water and the organic portion was separated. The aqueous portion was extracted three times with ethyl acetate and the combined organics were dried (MgSO$_4$), filtered and concentrated in vacuo. Chromatography on 75 g silica gel (20% ethyl acetate/toluene) followed by recrystallization from ethyl ether, filtration and drying in vacuo at 60° C. afforded 0.15 g (9%) of the title compound.

Analysis calculated for $C_{16}H_{18}NFO_2S \cdot 0.25H_2O$: %C, 61.62; %H, 5.98; %N, 4.49. Found: %C, 61.67; %H, 5.83; %N, 4.64.

Field Desorption Mass Spectrum: M=307

EXAMPLE 3

N-2-(4-(3-formylphenyl)phenyl)propyl methanesulfonamide

To a degassed solution of 1.5 g (5.1 mmol) of material from Example 1, 1.2 g (8.1 mmol) of 3-formylbenzeneboronic acid and 1.1 g (8.1 mmol) of potassium carbonate in 30 mL of toluene was added 0.3 g (0.3 mmol) of tetrakis-(triphenyl-phosphine)palladium(0). The mixture was heated to 100° C. for 16 hours whereupon 5 mL of water was added and heating continued for 1 hour. The mixture was then cooled to ambient temperature and 10 mL of water was added. The organic portion was separated and the aqueous portion was extracted twice with ethyl acetate. The combined organics were dried (MgSO$_4$), filtered and concentrated in vacuo. Chromatography on 50 g silica gel (40% ethyl acetate/hexane) afforded 0.7 g (41%) of the title compound.

Analysis calculated for $C_{17}H_{19}NO_3S$: %C, 64.33; %H, 6.03; %N, 4.41. Found: %C, 64.33; %H, 6.06; %N, 4.01.

Field Desorption Mass Spectrum: M=317

EXAMPLE 4

N-2-(4-(4-formylphenyl)phenyl)propyl methanesulfonamide

To a degassed solution of 1.5 g (5.1 mmol) of material from Example 1, 1.2 g (8.1 mmol) of 4-formylbenzeneboronic acid and 1.1 g (8.1 mmol) of potassium carbonate in 30 mL of toluene was added 0.3 g (0.3 mmol) of tetrakis(triphenyl-phosphine)palladium(0). The mixture was heated to 100° C. for 4 hours whereupon 0.3 g (2.0 mmol) of 4-formylbenzeneboronic acid and 0.1 g (0.09 mmol) of tetrakis(triphenylphosphine)-palladium(0) was added and heating continued for 16 hours. To this solution was added 5 mL of water and heating continued for 1 hour. The mixture was then cooled to ambient temperature and 10 mL of water was added. The organic portion was separated and the aqueous portion was extracted twice with ethyl acetate. The combined organics were dried (MgSO$_4$), filtered and concentrated in vacuo. Chromatography on 50 g silica gel (50% ethyl acetate/hexane) afforded a solid which was recrystallized from bromobutane/ethyl acetate, filtered and dried in vacuo at 60° C. to afford 0.5 g (32%) of the title compound.

Analysis calculated for $C_{17}H_{19}NO_3S$: %C, 64.33; %H, 6.03; %N, 4.41. Found: %C, 64.62; %H, 5.97; %N, 4.36.

Field Desorption Mass Spectrum: M=317

EXAMPLE 5

N-2-(4-(3-thienyl)phenyl)propyl methanesulfonamide

To a degassed solution of 1.5 g (5.1 mmol) of material from Example 1, 1.0 g (7.7 mmol) of thiophene-3-boronic acid and 1.1 g (7.7 mmol) of potassium carbonate in 30 mL of toluene was added 0.3 g (0.3 mmol) of tetrakis(triphenylphosphine)palladium(0). The mixture was heated to 100° C. for 4 hours, cooled to ambient temperature and diluted with 20 mL of ethyl acetate. The mixture was then washed once with water, and the organic portion was separated. The aqueous portion was extracted twice with ethyl acetate and the combined organics were dried (MgSO$_4$), filtered and concentrated in vacuo. Chromatography on 50 g silica gel (35% ethyl acetate/hexane) afforded a solid which was recrystallized from bromobutane, filtered and dried in vacuo at 60° C. to afford 0.4 g (27%) of the title compound.

Analysis calculated for $C_{14}H_{17}NO_2S_2$: %C, 56.92; %H, 5.80; %N, 4.74. Found: %C, 57.00; %H, 5.92; %N, 4.78.

Field Desorption Mass Spectrum: M=295

EXAMPLE 6

N-2-(4-(2-methoxyphenyl)phenyl)propyl methanesulfonamide

To a degassed solution of 1.0 g (3.4 mmol) of material from Example 1, 0.8 g (5.1 mmol) of 2-methoxybenzeneboronic acid and 0.7 g (5.1 mmol) of potassium carbonate in 15 mL of dioxane and 5 mL of water was added 0.2 g (0.2 mmol) of tetrakis(triphenylphosphine) palladium(0). The mixture was heated to 100° C. for 16 hours. The reaction mixture was cooled to ambient temperature, diluted with 10 mL of water and extracted three times with ethyl acetate. The combined organics were dried (MgSO$_4$), filtered and concentrated in vacuo. Chromatography on 50 g silica gel (35% ethyl acetate/hexane) afforded 1.0 g (90%) Of the title compound as a viscous oil.

Analysis calculated for $C_{17}H_{21}NO_3S$: %C, 63.92; %H, 6.62; %N, 4.39. Found: %C,63.68; %H, 6.78; %N, 4.23.

Field Desorption Mass Spectrum: M=319

EXAMPLE 7

N-2-(4-(2-fluorophenyl)phenyl)ethyl)2-proranesulfonamide

A. (2-(4-bromophenyl)-N-(t-butoxycarbonyl)ethylamine: To a solution of 10.0 g (50.0 mmol) of 4-bromophenethylamine in 100 mL of chloroform and 100 mL of saturated sodium bicarbonate was added 11.0 g (50.0 mmol) of di-tert-butyl dicarbonate. The solution was stirred at ambient temperature for 1 hour. The organic layer was separated and the aqueous layer was extracted three times with 30 mL each of chloroform. The combined organic extracts were dried (MgSO$_4$), filtered and concentrated in vacuo to afford 15 g (100%) of the title compound.

B. 2-(4-(2-fluorophenyl)phenyl)-N-(t-butoxycarbonyl)-phenyl ethylamine: To a degassed solution of 7.9 g (26.2 mmol) of material from Step A, 5.5 g (39.3 mmol) of material from Preparation 3 and 5.4 g (39.3 mmol) of potassium carbonate in 90 mL of toluene was added 1.5 g (1.3 mmol) of tetrakis-(triphenylphosphine)palladium (0). The mixture was heated at 90° C. for 3 hours. The mixture was cooled to ambient temperature and 90 mL of water was added. The organic layer was separated and the aqueous layer was extracted three times with 30 mL each of ethyl acetate. The combined organic extracts were dried (MgSO$_4$), filtered and concentrated in vacuo. Chromatography (400 g of silica gel, 15% ethyl acetate/hexane) of the residue afforded 7.1 g of material that was triturated in hexane to afford 3.5 g (42%) of the title compound.

C. 2-(4'-(2-fluorobiphenyl))ethylamine: A solution of 3.5 g of material from Step B in 40 mL 20% trifluoroacetic acid/dichloromethane was stirred at ambient temperature for 1 hour. The mixture was concentrated in vacuo to afford 3.9 g (100%) of the title compound.

D. A solution of 1.0 g (3.0 mmol) of material from Step C and 1 mL (7.6 mmol) of triethylamine in 10 mL of dichloro-methane was cooled to 0° C. A solution of 0.33 mL (3.0 mmol) of isopropylsulfonyl chloride in 5 mL of dichloromethane was added dropwise. The ice-bath was removed and the mixture was stirred at ambient temperature for 1 hour. The mixture was diluted with 10 mL of ether and washed with 20 mL of 10% aqueous sodium bisulfate, the organic layer was separated and the aqueous layer extracted three times with 10 mL each of ether. The combined organics were dried (MgSO$_4$), filtered and concentrated in vacuo to afford 0.5 g (52%) of the title compound.

Analysis calculated for $C_{17}H_{20}FNO_2S$ .0.25 $H_2O$: %C, 62.65; %H, 6.34; %N, 4.30. Found: %C, 62.62; %H, 6.15; %N, 4.49.

Field Desorption Mass Spectrum: M=321.

EXAMPLE 8

N-2-(4-(2-fluorophenyl)phenyl)propyl ethenesulfonamide

A solution of 1.0 g (4.4 mmol) of material from Preparation 6 and 0.67 mL (4.8 mmol) of triethylamine in 15 mL of dichloromethane was cooled to 0° C. A solution of 0.46 mL (4.4 mmol) of 2-chloro-1-ethanesulfonyl chloride in 2 mL of dichloromethane was added dropwise. The ice-bath was removed and the mixture was stirred at ambient temperature for 1 hour. The mixture was diluted with 15 mL of ether and washed with 15 mL of 10% aqueous sodium bisulfate, the organic layer was separated and the aqueous layer extracted three times with 5 mL each of ether. The combined organics were dried (MgSO$_4$), filtered and concentrated in vacuo. Chromatography (25 g of silica gel, 30% ethyl acetate/-hexane) of the residue afforded 0.6 g (43%) of the title compound.

Analysis calculated for $C_{17}H_{18}FNO_2S$: %C, 63.93; %H, 5.68; %N, 4.39. Found: %C, 63.98; %H, 5.58; %N, 4.42.

Field Desorption Mass Spectrum: M=319.

EXAMPLE 9

N-2-(4-(2-fluorophenyl)phenyl)propyl ethanesulfonamide

A solution of 0.2 g (0.80 mmol) of material from Preparation 6 and 0.13 mL (0.95 mmol) of triethylamine in 5 mL of dichloromethane was cooled to 0° C. A solution of 0.076 mL (0.80 mmol) of ethanesulfonyl chloride in 1 mL of dichloromethane was added dropwise. The ice-bath was removed and the mixture was stirred at ambient temperature for 16 hours. The mixture was washed with 5 mL of 10% aqueous sodium bisulfate, the organic layer was separated and the aqueous layer extracted one time with 5 mL of dichloro-methane. The combined organics were dried (MgSO$_4$), filtered and concentrated in vacuo. Chromatography (25 g of silica gel, 35% ethyl acetate/hexane) of the residue afforded 0.20 g (78%) of the title compound.

Analysis calculated for $C_{17}H_{20}FNO_2S$: %C, 63.53; %H, 6.27; %N, 4.36. Found: %C, 63.24; %H, 6.27; %N, 4.39.

Field Desorption Mass Spectrum: M=321.

EXAMPLE 10

N-2-(4-(2-fluorophenyl)phenyl)propyl 2-propanesulfonamide

A solution of 0.2 g (0.80 mmol) of material from Preparation 6 and 0.13 mL (0.95 mmol) of triethylamine in 5 mL of dichloromethane was cooled to 0° C. A solution of 0.090 mL (0.80 mmol) of isopropylsulfonyl chloride in 1 mL of dichloromethane was added dropwise. The ice-bath was removed and the mixture was stirred at ambient temperature for 16 hours. The mixture was washed with 5 mL of 10% aqueous sodium bisulfate, the organic layer was separated and the aqueous layer extracted one time with 5 mL of dichloro-methane. The combined organics were dried (MgSO$_4$), filtered and concentrated in vacuo. Chromatography (25 g of silica gel, 35% ethyl acetate/hexane) of the residue afforded 0.040 g (15%) of the title compound.

Analysis calculated for $C_{18}H_{22}FNO_2S$: %C, 64.45; %H, 6.61; %N, 4.81. Found: %C, 64.2; %H, 6.51; %N, 4.02.

Field Desorption Mass Spectrum: M=335.

EXAMPLE 11

N-2-(4-(2-fluorophenyl)phenyl)propyl N',N'-dimethylsulfamide

A solution of 0.2 g (0.80 mmol) of material from Preparation 6 and 0.13 mL (0.95 mmol) of triethylamine in 5 mL of dichloromethane was cooled to 0° C. A solution of 0.086 mL (0.80 mmol) of dimethylsulfamoyl chloride in 1 mL of dichloromethane was added dropwise. The ice-bath was removed and the mixture was stirred at ambient temperature for 16 hours. The mixture was washed with 5 mL of 10% aqueous sodium bisulfate, the organic layer was separated and the aqueous layer extracted one time with 5 mL of dichloro-methane. The combined organics were dried ($MgSO_4$), filtered and concentrated in vacuo. Chromatography (25 g of silica gel, 35% ethyl acetate/hexane) of the residue afforded 0.20 g (74%) of the title compound.

Analysis calculated for $C_{17}H_{21}FN_2O_2S$: %C, 60.69; %H, 6.29; %N, 8.33. Found: %C, 60.42; %H, 6.23; %N, 8.06.

Field Desorption Mass Spectrum: M=336

EXAMPLE 12

N-2-(4-Isopropyl)phenyl)propyl trifluoromethanesulfonamide

A suspension of the product of Preparation 8, 0.30 g (1.40 mmol) in dichloromethane (20 ml) was cooled to 0° C. Triethylamine 0.59 ml (4.21 mmol) was added to the suspension, followed by trifluoromethanesulfonyl chloride 0.16 ml (1.54 mmol). The solution was stirred at 0° C. for thirty minutes then warmed to ambient temperature. The progress of the reaction was monitored by thin layer chromatography. After consumption of the starting material, the reaction mixture was partitioned between water and dichloromethane. The organic fraction was washed with 0.2M hydrochloric acid, brine, dried ($MgSO_4$) and concentrated in vacuo. Chromatography ($SiO_2$, 30% ethyl acetate/hexanes) gave 0.35 g (81%) of the title compound.

Field Desorption Mass Spectrum: M=309.

Analysis for $C_{13}H_{18}F_3NO_3S$: Theory: C, 50.48; H, 5.86; N, 4.53. Found: C, 50.40; H, 5.78; N, 4.74.

EXAMPLE 13

N-2-(4-Isopropylphenyl)propyl 2-propanesulfonamide

A suspension of the product of Preparation 8, 0.30 g, (1.40 mmol) in dichloromethane (20 ml) was cooled to 0° C. Triethylamine 0.59 ml (4.21 mmol) was added to the suspension, followed by isopropylsulfonylchloride (0.16 ml, 1.54 mmol). The solution was stirred at 0° C. for thirty minutes then warmed to ambient temperature. The progress of the reaction was monitored by thin layer chromatography. After consumption of the starting material, the reaction mixture was partitioned between water and dichloromethane. The organic fraction was washed with 0.2M hydrochloric acid, brine, dried over ($MgSO_4$) and concentrated in vacuo. Chromatography ($SiO_2$, 30% ethyl acetate/hexanes) gave the title compound 0.35 g (81%).

Field Desorption Mass Spectrum: M=283.

Analysis for $C_{13}H_{18}F_3NO_3S$: Theory: C, 63.57; H, 8.89; N, 4.94. Found: C, 63.63; H, 8.90; N, 5.18.

EXAMPLE 14

N-2-(4-Methoxyphenyl)propyl trifluoromethanesulfonamide

A suspension of the product of Preparation 10, 1.00 g (4.96 mmol) in dichloromethane (50 ml) was cooled to 0° C. Triethylamine 2.09 ml (14.9 mmol) was added to the suspension, followed by trifluoromethanesulfonyl-chloride 0.58 ml (5.45 mmol). The solution was stirred at 0° C. for thirty minutes then warmed to ambient temperature. The progress of the reaction was monitored by thin layer chromatography. After consumption of the starting material, the reaction mixture was partitioned between water and dichloromethane. The organic fraction was washed with 0.2M hydrochloric acid, brine, dried over magnesium sulfate and concentrated in vacuo. Chromatography ($SiO_2$, 30% ethyl acetate/hexanes) gave the title compound 1.07 g (73%).

Field Desorption Mass Spectrum: M=297.

Analysis for $C_{11}H_{14}F_3NO_3S$: Theory: C, 44.44; H, 4.75; N, 4.77. Found: C, 44.54; H, 4.55; N, 4.80.

EXAMPLE 15

N-2-(4-Cyclopentylphenyl)propyl methanesulfonamide

Condition 1: The product of Example 1, 0.50 g (1.71 mmol) was dissolved in anhydrous tetrahydrofuran (5 ml) under an atmosphere of nitrogen. To this was added tetrakis-(triphenylphosphine)palladium(0) (0.099 g, 0.086 mmol) followed by cyclopentyl magnesium bromide (2 M in diethyl ether, 2.14 ml, 4.28 mmol). The solution was heated to reflux for 16 hours. Upon cooling the reaction was partitioned between water and diethyl ether. The aqueous layer was back extracted with diethyl ether twice and the organic fractions combined. The organic layers were washed with brine, dried ($MgSO_4$) and concentrated in vacua. Chromatography ($SiO_2$, 30% ethyl acetate/hexanes) gave the title compound 0.06 g (13%).

Field Desorption Mass Spectrum: M=281.

Analysis for $C_{15}H_{23}NO_2S$: Theory: C, 64.02; H, 8.24; N, 4.98. Found: C, 64.30; H, 8.35; N, 4.84.

Condition 2: Subsequently it has been discovered that the optimal conditions for the above reaction are as follows: The bromide was dissolved in diethyl ether and cooled to −78° C. [1,1'-bis(diphenylphosphino)ferrocene]dichloropalladium (II) ($PdCl_2$(dppf)) was added followed by the appropriate alkyl magnesium reagent. The solution was stirred for an hour then allowed to warm to ambient temperature over 2 hours. The work up is the same as in Condition 1 described above.

EXAMPLE 16

N-2-(4-t-butylphenyl)propyl methanesulfonamide 65 mg (0.57 mmol) of methanesulfonyl chloride in dichloromethane (5 mL) was added dropwise to a solution of 100 mg (0.52 mmol) of the product of Preparation 23 and 60 mg (0.59 mmol) of triethylamine in dichloromethane (15 mL) at ambient temperature under $N_2$. The reaction mixture was stirred for 16 hours at ambient temperature. The mixture was then concentrated under reduced pressure and the resulting semi-solid was taken into 25 mL ethyl acetate, washed once with 25 mL $H_2O$, dried over $K_2CO_3$, and concentrated under reduced pressure. Recrystallization from hexane/ethyl acetate 9:1 produced the title compound 65 mg (46%) as white crystals.

Analysis calculated for $C_{14}H_{23}NO_2S$: % C, 62.42; % H, 8.61; % N,5.20. Found % C 62.64; % H, 8.41; % N, 5.19.

Mass Spectrum: M=269.

EXAMPLE 17

N-2-(4-t-butylphenyl)propyl trifluoromethanesulfonamide

The title compound 70 mg (29%) was prepared as an oil following the method of Example 16, starting from the product of Preparation 23 and using trifluoromethanesulfonyl chloride.

Analysis calculated for $C_{14}H_{20}NO_2SF_3$: % C, 52.00; % H, 6.23; % N, 4.33. Found % C, 51.79; % H, 6.20; % N, 4.27. Mass Spectrum: M=323.

EXAMPLE 18

N-2-(4-t-butylphenyl)butyl methanesulfonamide

The title compound, 140 mg (67%) was prepared as an oil following the method of Example 16, starting from the product of Preparation 24. Purification was achieved by silica gel chromatography (Chromatotron-1000 micron rotor) eluting with a solvent of hexane/ethyl acetate 3:1.

Analysis calculated for $C_{15}H_{25}NO_2S$: % C, 63.57; % H, 8.89; % N, 4.94. Found % C, 63.63, % H, 8.49; % N, 4.93.

Mass Spectrum: M=283.

EXAMPLE 19

N-2-(4-t-butylphenyl)-2-methylpropyl trifluoromethane-sulfonamide

The title compound, 131 mg (40%) was prepared as a crystalline solid from hexane/ethyl acetate 19:1 following the method of Example 16, starting from the product of Preparation 25 and using trifluoromethanesulfonyl chloride.

Analysis calculated for $C_{15}H_{22}NO_2SF_3$: % C, 53.40; % H, 6.57; % N, 4.15. Found % C, 53.75; % H, 6.40; % N, 4.02. Mass Spectrum: M=337.

EXAMPLE 20

N-2-(2-naphthyl)propyl trifluoromethanesulfonamide

The title compound was prepared following the method of Example 16, starting from the product of Preparation 26. Purification was achieved by silica gel chromatography (Chromatotron-1000 micron rotor) and eluting with a solvent of hexane/ethyl acetate 19:1 to yield the title compound 140 mg (44%) as a solid.

Analysis calculated for $C_{14}H_{14}NO_2SF_3$: % C, 52.99; % H, 4.45; % N, 4.41. Found: % C, 52.90; % H, 4.42; % N, 4.32.

Mass Spectrum: M=317.

EXAMPLE 21

N-2-(4-t-butylphenyl)butyl trifluoromethanesulfonamide

The title compound was prepared following the method of Example 16, starting from the product of Preparation 24 and using trifluoromethanesulfonyl chloride. Purification was achieved by silica gel chromatography (Chromatotron-2000 micron rotor) eluting with a solvent of hexane/ethyl acetate 19:1 to yield the title compound, 187 mg (57%) as an oil.

Analysis calculated for $C_{15}H_{22}NO_2SF_3$: % C, 53.56; % H, 6.31; % N, 4.12. Found: % C, 53.40; % H, 6.57; % N, 4.15.

Mass Spectrum: M=337.

EXAMPLE 22

N-2-(4-t-butylphenyl)butyl 2-propanesulfonamide

The title compound was prepared following the method of Example 16, starting from the product of Preparation 24 and isopropylsulfonyl chloride. Purification was achieved by silica gel chromatography (Chromatotron-2000 micron rotor) eluting with a gradient solvent of hexane to hexane/ethyl acetate 4:1 producing the title compound 73 mg (32%) as an oil.

Analysis calculated for $C_{17}H_{29}NO_2S$: % C, 65.55; % H, 9.38; % N, 4.50. Found: % C, 64.65; % H, 8.96; % N, 4.60.

Mass Spectrum: M=311.

EXAMPLE 23

N-2-(4-t-butylphenyl)propyl 2-propanesulfonamide

The title compound was prepared following the method of Example 16, starting from the product of Preparation 23 and isopropylsulfonyl chloride. Purification was achieved via silica gel chromatography (Chromatotron-2000 micron rotor) eluting with a solvent of hexane/ethyl acetate 4:1 to produce the title compound 111 mg (29%).

Analysis calculated for $C_{16}H_{27}NO_2S$: % C, 64.61; % H, 9.15; % N, 4.71. Found: % C, 64.53, % H, 8.99; % N, 4.92.

Mass spectrum: M=297.

EXAMPLE 24

N-1-(4-t-butylphenyl)cyclopropylmethyl trifluoromethanesulfonamide 165 mg (0.98 mmol) of trifluoromethylsulfonyl chloride, 100 mg (0.49 mmol) of the product of Preparation 30, and 100 mg (0.98 mmol) of triethylamine were combined in dichloro-methane (15 mL) and reacted as described in Example 16 to yield 164 mg of an oil. This material was purified via silica gel chromatography eluting with a gradient solvent of hexane to hexane/EtOAc 9:1 to yield 100 mg (61%) of the title compound as a slowly crystallizing oil. m.p. 82°–84° C. Calculated for $C_{15}H_{20}NO_2SF_3$: Theory: C, 53.72; H, 6.01; N, 4.18 Found: C, 53.97; H, 6.12; N, 4.10.

Mass spectrum: M=335.

EXAMPLE 25

N-1-(4-t-butylphenyl)cyclopropylmethyl 2-propanesulfonamide 140 mg (0.98 mmol) of isopropylsulfonyl chloride, 100 mg (0.49 mmol) of the product of Preparation 30, and 100 mg (0.98 mmol) of triethylamine were combined in dichloromethane (15 mL) and reacted as described in Example 16 to yield 147 mg of an oil. This material was purified via silica gel chromatography eluting with a gradient solvent of hexane/EtOAc 19:1 to hexane/EtOAc 1:1 to yield the title compound 33 mg (22%) as a slowly crystallizing oil. m.p. 87°–89.5° C. Calculated for $C_{17}H_{27}NO_2S$: Theory C, 65.98; H, 8.79; N, 4.53 Found: C, 65.78; H, 9.01; N, 4.35.

EXAMPLE 26

N-2-(4-(4-Methylphenyl)phenyl)propyl methanesulfonamide

To a degassed solution of 1.4 g (4.7 mmol) of the product of Example 1, 1.0 g (7.1 mmol) of 4-methylbenzene-boronic acid, 1.0 g (7.1 mmol) of potassium carbonate in 30 mL of toluene, and 10 mL of water was added 0.3 g (0.2 mmol) of tetrakis(triphenylphosphine)palladium(0). The mixture was heated to 100° C. for 2 hr, cooled to ambient temperature and the organic portion was separated. The aqueous portion was extracted three times with ethyl acetate and the combined organic portions were dried ($MgSO_4$), filtered and concentrated in vacuo. The residue was chromatographed on silica gel (30% ethyl acetate/hexane) to afford an off-white solid. The solid was suspended in diethyl ether, filtered and dried in vacuo to afford 0.6 g (43%) of the title compound.

Analysis calculated for $C_{17}H_{21}NO_2S$: %C, 67.29; %H, 6.98; %N, 4.62. Found: %C, 66.98; %H, 6.96; %N, 4.36.

Field Desorption Mass Spectrum: M=307

EXAMPLE 27

N-2-(4-Bromophenyl)propyl 2-propylsulfonamide

To a suspension of 0.5 g (2.0 mmol) of the product of Preparation 31 in 5 mL of dichloromethane was added 0.6 mL (4.0 mmol) of triethylamine. The mixture was cooled to 0° C. and 0.2 mL (2.0 mmol) of isopropylsulfonyl chloride was added. After stirring at 0° C. for 20 min, the mixture was washed once with 10% aqueous sodium bisulfate and the organic layer was separated. The aqueous layer was extracted three times with dichloromethane. The combined organic portions were dried ($Na_2SO_4$), filtered and concentrated in vacuo. Chromatography on 50 g silica gel (35% ethyl acetate/hexane) afforded 0.2 g (25%) of the title compound.

Analysis calculated for $C_{12}H_{18}NO_2SBr$: %C, 45.01; %H, 5.67; %N, 4.37. Found: %C, 45.30; %H, 5.92; %N, 4.43.

Field Desorption Mass Spectrum: M+1=321

EXAMPLE 28

N-2-(4-(3-thienyl)phenylpropyl 2-propanesulfonamide

A. N-2-(4-(3-thienyl)phenyl)-N-t-butoxycarbonylpropyl amine: To a degassed solution of 8.2 g (26.0 mmol) of material from Preparation 4, 4.0 g (31.2 mmol) of thiophene-3-boronic acid and 5.3 g (39.0 mmol) of potassium carbonate in 75 mL of dioxane and 25 mL of water was added 1.5 g (1.3 mmol) of tetrakis(triphenylphosphine)palladium(0). The mixture was heated at 90° C. for 18 h. The mixture was cooled to ambient temperature and 200 mL of water and 100 mL of ether was added. The organic layer was separated and the aqueous layer was extracted three times with 60 mL each of ether. The combined organic extracts were dried ($MgSO_4$), filtered and concentrated in vacuo. Chromatography (500 g of silica gel, 10% ethyl acetate/hexane) of the residue afforded 7.8 g (94%) of the title compound.

B. 2-(4-(3-thienyl)phenyl)propylamine trifluoroacetic acid salt: A solution of 7.8 g (24.6 mmol) of material from Step A in 80 mL 20% trifluoroacetic acid/dichloromethane was stirred at ambient temperature for 5 h. The mixture was concentrated in vacuo to afford 8.1 g (100%) of the title compound.

C. A solution of 0.5 g (1.5 mmol) of material from Step B and 0.52 mL (3.7 mmol) of triethylamine in 10 mL of dichloro-methane was cooled to 0° C. A solution of 0.17 mL (1.5 mmol) of isopropylsulfonyl chloride in 1 mL of dichloromethane was added dropwise. The ice-bath was removed and the mixture was stirred at room temperature for 5 h. The mixture was washed with 10 mL of 10% aqueous sodium bisulfate, the organic layer was separated and the aqueous layer extracted three times with 5 mL of dichloromethane. The combined organics were dried ($MgSO_4$), filtered and concentrated in vacuo. Chromatography (25 g of silica gel, 35% ethyl acetate/-hexane) of the residue afforded 0.100 g (21%) of the title compound.

Analysis calculated for $C_{16}H_{21}NO_2S_2$: %C, 59.41; %H, 6.54; %N, 4.33. Found: %C, 59.34; %H, 6.34; %N, 4.29.

Field Desorption Mass Spectrum: M=323.

EXAMPLE 29

N-2-(4-(3-thienyl)phenylpropyl dimethylsulfamide

A. A solution of 0.5 g (1.5 mmol) of material from Example 28, Step B and 0.52 mL (3.70 mmol) of triethylamine in 10 mL of dichloromethane was cooled to 0° C. A solution of 0.16 mL (1.5 mmol) of dimethylsulfamoyl chloride in 1 mL of dichloro-methane was added dropwise. The ice-bath was removed and the mixture was stirred at ambient temperature for 5 h. The mixture was washed with 10 mL of 10% aqueous sodium bisulfate, the organic layer was separated and the aqueous layer extracted three times with 5 mL of dichloromethane. The combined organics were dried ($MgSO_4$), filtered and concentrated in vacuo. The residue was suspended in 50% ether/hexane and filtered to afford 0.22 g (46%) of the title compound.

Analysis calculated for $C_{15}H_{20}N_2O_2S_2$: %C, 55.53; %H, 6.21; %N, 8.63. Found: %C, 55.51; %H, 6.21; %N, 8.39.

Field Desorption Mass Spectrum: M=324.

EXAMPLE 30

N-2-(4-Methoxyphenyl)propyl 2-propanesulfonamide

The title product was prepared from the product of Preparation 10 as described in Example 13.

Field Desorption Mass Spectrum: M=271.4

Analysis for $C_{13}H_{21}NO_3S$: Theory: C, 56.71; H, 8.16; N, 4.86. Found: C, 57.54; H, 7.80; N, 5.16.

EXAMPLE 31

N-2-(4-Methylphenyl)propyl) 2-propanesulfonamide

The title compound was prepared from the product of Preparation 33 as described in Example 13.

Field Desorption Mass Spectrum: M=255.2.

Analysis for $C_{13}H_{21}NO_2S$: Theory: C, 61.14; H, 8.29; N, 5.48. Found: C, 61.23; H, 8.35; N, 5.30.

EXAMPLE 32

N-2-(4-Isopropylphenyl)propyl ethanesulfonamide

The title product was prepared from the product of Preparation 8 as described in Example 13 with the exception that ethanesulfonyl chloride was used instead of isopropylsulfonyl chloride.

Field Desorption Mass Spectrum: M=269.1.

Analysis for $C_{14}H_{23}NO_2S$: Theory: C, 62.42; H, 8.61; N, 5.20. Found: C, 62.68; H, 8.34; N, 5.11.

EXAMPLE 33

N-2-(4-Isopropylphenyl)propyl dimethylsulfamide

The title product was prepared from the product of Preparation 8 as described in Example 13 with the exception that dimethylsulfamoyl chloride was used instead of isopropylsulfonyl chloride.

Field Desorption Mass Spectrum: M=349.1.

Analysis for $C_{14}H_{23}NO_2S$: Theory: C, 55.00; H, 6.35; N, 4.01. Found: C, 54.70; H, 6.12; N, 3.82.

EXAMPLE 34

N-2-(4-Isobutylphenyl)propyl 2-propanesulfonamide

The title product was prepared from 2-(4-isobutylphenyl) propyl amine hydrochloride as described in Example 13.

Field Desorption Mass Spectrum: M=297.2

Analysis for $C_{16}H_{27}NO_2S$: Theory: C, 64.61; H, 9.15; N, 4.71. Found: C, 64.84; H, 9.10; N, 4.74.

EXAMPLE 35

N-2-(4-Cyclopentylphenyl)propyl 2-propanesulfonamide

The title product was prepared from ((4-bromo)-2-methylphenethyl) 2-propanesulfonamide as described in Example 15, Condition 2.

Field Desorption Mass Spectrum: M=309.3.

Analysis for $C_{17}H_{27}NO_2S$: Theory: C, 65.98; H, 8.79; N, 4.53. Found: C, 66.21; H, 9.04; N, 4.54.

EXAMPLE 36

N-2-(4-Cyclohexylphenyl)propyl 2-propanesulfonamide

The title product was prepared from the product of Example 27 as described in Example 15, Condition 2, with the exception that cyclohexylmagnesium chloride was used instead of cyclopentylmagnesium bromide.

Field Desorption Mass Spectrum: M=323.3.

Analysis for $C_{18}H_{29}NO_2S$: Theory: C, 66.83; H, 9.04; N, 4.33. Found: C, 67.00; H, 9.18; N, 4.09.

EXAMPLE 37

N-2-(3-Chloro4-piperidinylphenyl)propyl 2-propanesulfonamide

The title product was prepared from 2-(3-chloro4-piperidinylphenyl)propylamine hydrochloride as described in Example 13.

Field Desorption Mass Spectrum: M=358.2

Analysis for $C_{17}H_{27}ClN_2O_2S$: Theory: C, 56.89; H, 7.58; N, 7.80. Found: C, 57.19; H, 7.68; N, 8.02.

EXAMPLE 38

N-2-(−)-(4-Piperidinylphenyl)propyl) 2-propanesulfonamide

The title product was prepared from (−)-2-(4-piperidinylphenyl)propylamine hydrochloride (Synthesis, 6, 447, 1991) as described in Example 13.

Field Desorption Mass Spectrum: M=324.2.

Analysis for $C_{17}H_{28}N_2O_2S$: Theory: C, 62.93; H,8.70; N, 8.63. Found: C, 63.22; H, 8.51; N, 8.49.

EXAMPLE 39

N-2-(+)-((4-Piperidinylphenyl)propyl) 2-propanesulfonamide

The title product was prepared from (+)-2-(4-piperidinyl phenyl)propylamine hydrochloride (Synthesis 6, 447, 1991) as described in Example 13.

Field Desorption Mass Spectrum: M=324.2.

Analysis for $C_{17}H_{28}N_2O_2S$: Theory: C, 62.93; H, 8.70; N, 8.63. Found: C, 62.68; H, 8.45; N, 8.72.

EXAMPLE 40

N-2-(4-Benzyloxyphenyl)propyl) 2-propanesulfonamide

The title compound was prepared from the product of Preparation 35 as described in Example 13.

Field Desorption Mass Spectrum: M=347.2.

Analysis for $C_{19}H_{25}NO_3S$: Theory: C, 65.68; H, 7.25; N, 4.03. Found: C, 65.63; H, 7.31; N, 4.07.

EXAMPLE 41

N-2-(4-Isopropoxyphenyl)propyl 2-propanesulfonamide

The product from Preparation 36 (0.14 g, 0.40 mmol) was dissolved in dimethylformamide and sodium hydride (0.018 g, 0.44 mmol) added. After 10 minutes, 2-bromopropane (0.054g, 0.44 mmol) was added and the reaction stirred at ambient temperature for 2 hours. The reaction mixture was partitioned between diethyl ether and water. The organic fraction was washed with brine, dried over magnesium sulfate and concentrated in vacuo. Chromatography ($SiO_2$, 20% ethyl acetate/hexanes) gave 0.11 g (70%) of the alkylated material. This material was dissolved in dichloromethane and treated with trifluoroacetic acid at ambient temperature. The reaction was washed with water, brine, dried over magnesium sulfate and concentrated in vacuo to yield 0.083 g of the title product.

Field Desorption Mass Spectrum: M=299.0.

Analysis for $C_{15}H_{25}NO_3S$: Theory: C, 60.17; H, 8.42; N, 4.68. Found: C, 58.57; H, 8.40; N, 4.31.

EXAMPLE 42

N-2-(4-(2-fluorophenyl)phenyl)propyl 2-methanesulfonamide

A solution of 1.6 g (6.5 mmol) of material from Preparation 6 and 1.2 mL (7.1 mmol) of N,N-diisopropyl-ethylamine in 20 mL of dichloromethane was cooled to 0° C. A solution of 0.51 mL (6.5 mmol) of methanesulfonyl chloride in 1 mL of dichloromethane was added dropwise. The ice-bath was removed and the mixture was stirred at ambient temperature for 1 hour. The mixture was washed with 20 mL of 10% aqueous sodium bisulfate, the organic layer was separated and the aqueous layer was extracted three times with 5 mL of 1:1 dichloromethane/ether. The combined organics were dried ($MgSO_4$), filtered and concentrated in vacuo to afford 1.9 g (100%) of the title compound.

Field Desorption Mass Spectrum: M=307

Analysis for $C_{16}H_{18}FNO_2S$: Theory: C, 62.52; H, 5.90; N, 4.56. Found: C, 64.41; H, 5.99; N, 4.67.

EXAMPLE 43

N-1-methyl-2-(4-bromophenyl)ethyl 2-methanesulfonamide

A solution of 3.0 g (14.0 mmol) of the product of Preparation 38 and 2.1 mL (15.4 mmol) of triethylamine in 50 mL of dichloromethane was cooled to 0° C. A solution of 1.1 mL (14.0 mmol) of methanesulfonyl chloride in 2 mL of dichloromethane was added dropwise. The mixture was then stirred at 0° C. for 1 hour. The mixture was then washed with 50 mL of 10% aqueous sodium bisulfate, the organic layer was separated and the aqueous layer was extracted three times with 20 mL of diethyl ether. The combined organics were dried ($MgSO_4$), filtered and concentrated in vacuo. Chromatography (100 g of silica gel, 35% ethyl acetate/hexane) of the residue afforded 1.5 g (37%) of the title compound.

EXAMPLE 44

N-1-methyl-2-(4-(2-fluorophenyl)phenyl)ethyl 2-methanesulfonamide

To a degassed solution of 1.5 g (5.1 mmol) of the product of Example 43, 1.1 g (7.7 mmol) of the product of Preparation 3 and 1.1 g (7.7 mmol) of potassium carbonate in 20 mL of toluene was added 0.3 g (0.2 mmol) of tetrakis(triphenylphosphine)palladium(0). The mixture was heated at 90° C. for 18 hours. It was then cooled to ambient temperature and 20 mL of water were added. The organic layer was separated and the aqueous layer was extracted three times with 10 mL each of ethyl acetate. The combined organic extracts were dried (MgSO$_4$), filtered and concentrated in vacuo. The residue was suspended in diethyl ether and filtered to afford 0.673 g (43%) of the title compound.

Field Desorption Mass Spectrum: M=307

Analysis for $C_{16}H_{18}FNO_2S$: Theory: C, 62.52; H, 5.90; N, 4.56. Found: C, 62.26; H, 5.92; N, 4.49.

EXAMPLE 45

N-2-(4-(4-formylphenyl)phenyl)propyl 2-propanesulfonamide

A degassed solution of 2.4 g (7.5 mmol) of the material from Preparation 39, 1.7 g (11.2 mmol) of 4-formylphenylboronic acid, 1.6 g (11.2 mmol) of potassium carbonate and 0.4 g (0.4 mmol) of tetrakis(triphenylphosphine)palladium(0) in 33 mL of dioxane and 11 mL of water was heated to 100° C. overnight. The mixture was cooled to room temperature, diluted with 20 mL of water, and extracted three times with 50 mL each of ethyl acetate. The combined organics were dried (MgSO$_4$), filtered and concentrated in vacuo. Chromatography (175 g of silica gel, 35% ethyl acetate/hexane) of the residue afforded 1.8 g (71%) of the title compound.

Analysis calculated for $C_{19}H_{23}NO_3S$: %C, 66.06; %H, 6.71; %N, 4.05. Found: %C, 66.23; %H, 6.69; %N, 4.11.

Field Desorption Mass Spectrum: M=345

EXAMPLE 46

N-2-(4-(4-(hydroxymethyl)phenyl)phenyl)propyl 2-propanesulfonamide

A solution of 0.5 g (1.45 mmol) of the material from Example 45 and 0.055 g (1.45 mmol) of sodium borohydride in 5 mL of ethanol was stirred overnight at room temperature, then concentrated in vacuo. The residue was partitioned between 25 mL of water and 25 mL of ethyl acetate, the organic layer separated and the aqueous layer extracted three more times with 25 mL each of ethyl acetate. The combined organics were dried (MgSO$_4$), filtered and concentrated in vacuo. Chromatography (25 g of silica gel, 60% ethyl acetate/hexane) of the residue afforded 1.8 g (71%) of the title compound.

Analysis calculated for $C_{19}H_{25}NO_3S$: %C, 65.68; %H, 7.25; %N, 4.03. Found: %C, 65.40; %H, 7.40; %N, 4.02.

Field Desorption Mass Spectrum: M=347

EXAMPLE 47

N-2-(4-(2-formylphenyl)phenyl)propyl 2-propanesulfonamide

Prepared as in Example 45, using 8.1 g (25.1 mmol) of the material from Preparation 39, 4.7 g (31.4 mmol) of 2-formylphenylboronic acid, 5.2 g (37.3 mmol) of potassium carbonate and 1.5 g (1.3 mmol) of tetrakis(triphenylphosphine)palladium(0) in 93 mL of dioxane and 24 mL of water. Afforded 7.5 g (86%) of the title compound.

Analysis calculated for $C_{19}H_{23}NO_3S$: %C, 66.06; %H, 6.71; %N, 4.05. Found: %C, 66.06; %H, 6.70; %N, 4.10.

Field Desorption Mass Spectrum: M=345

EXAMPLE 48

N-2-(4-(2-(hydroxymethyl)phenyl)phenyl)propyl 2-propanesulfonamide

Prepared as in Example 46, using 2.0 g (5.8 mmol) of the material from Example 47 and 0.22 g (5.8 mmol) of sodium borohydride in 5 mL of ethanol. Afforded 1.7 g (84%) of the title compound.

Analysis calculated for $C_{19}H_{25}NO_3S$: %C, 65.68; %H, 7.25; %N, 4.03. Found: %C, 65.14; %H, 6.73; %N, 3.76.

Field Desorption Mass Spectrum: M=347

EXAMPLE 49

N-2-(4-(4-(2-t-butoxycarbonylamino)ethyl)phenyl)phenylpropyl 2-propanesulfonamide To a solution of 2.0 g (3.8 mmol) of material from Preparation 40 and 1.4 g (4.5 mmol) of material from Preparation 41 in 15 mL of toluene was added 0.2 g (0.2 mmol) of tetrakis(triphenylphosphine) palladium (0). The mixture was heated to 100° C. for 6.5 hours, cooled to room temperature and diluted with 15 mL of ethyl ether. The mixture was washed once with 15 mL of saturated aqueous potassium fluoride, the organic layer was separated and the aqueous layer was extracted three times with 10 mL each of ethyl ether. The combined organics were dried (MgSO$_4$), filtered and concentrated in vacuo. Chromatography (100 g silica gel, 30% ethyl acetate/hexane) of the residue affords 0.6 g (35%) of the title compound.

Analysis calculated for $C_{25}H_{36}N_2O_4S$: %C, 65.19; %H, 7.88; %N, 6.08. Found: %C, 65.29; %H, 7.84; %N, 5.84.

Mass Spectrum: M=460.

EXAMPLE 50

N-2-(4-(4-(2-aminoethyl)phenyl)phenyl)propyl 2-propanesulfonamide

A solution of 0.6 g (1.3 mmol) of material from Example 49 in 5 mL of 20% trifluoroacetic acid/dichloromethane was stirred at room temperature for 1.5 hours. The mixture was concentrated in vacuo and the residue was partitioned between 10 mL of dichloromethane and 5 mL of 5 N aqueous sodium hydroxide. The organic layer was separated and the aqueous layer was extracted three times with 5 mL each of dichloromethane. The combined organics were dried (Na$_2$SO$_4$), filtered and concentrated in vacuo. The resulting solid was suspended in hexane, filtered, rinsed once with hexane and dried in vacuo at ambient temperature to afford 0.4 g (88%) of the title compound.

Analysis calculated for $C_{20}H_{28}N_2O_2S$: %C, 66.63; %H, 7.83; %N, 7.77. Found: %C, 66.93; %H, 7.79; %N, 7.94.

Mass Spectrum: M=360.

EXAMPLE 51

N-2-(4-(4-(2-methanesulfonamido ethyl)phenyl)phenyl)propyl 2-propanesulfonamide To a room temperature solution of 0.1 g (0.3 mmol) of material from Example 50 and 0.06 mL (0.4 mmol) of triethylamine in 2 mL of dichloromethane was added 0.03 mL (0.4 mmol) of methanesulfonyl chloride. The mixture was stirred at ambient temperature for 16 hours. Chromatography (10 g silica gel, 50% ethyl acetate/hexane) of the reaction mixture afforded 0.1 g (94%) of the title compound.

Analysis calculated for $C_{21}H_{30}N_2O_4S_2$: %C, 57.51; %H, 6.89; %N, 6.39. Found: %C, 57.90; %H, 6.72; %N, 6.33.

Mass Spectrum: M=438.

EXAMPLE 52

N-2-(4-(4-hydroxymethyl)phenyl)phenyl)propyl 2-propanesulfonamide

To a solution of 0.5 g (1.5 mmol) of material from Example 45 in 5 mL ethanol was added 0.06 g (1.5 mmol) of sodium borohydride. The mixture was stirred at ambient temperature for 16 hours, concentrated in vacuo and partitioned between 10 mL of ethyl acetate and 5 mL of water. The organic layer was separated and the aqueous portion was extracted three times with 5 mL each of ethyl acetate. The combined organics were dried ($MgSO_4$), filtered and concentrated in vacuo. Chromatography (25 g of silica gel, 60% ethyl acetate/hexane) of the residue afforded 0.5 g (98%) of the title compound. Analysis calculated for $C_{19}H_{25}NO_3S$: %C, 65.68; %H, 7.25; %N, 4.03. Found: %C, 65.40; %H, 7.40; %N, 4.02.

Mass Spectrum: M=347.

EXAMPLE 53

N-2-(4-cyanophenyl)propyl 2-propanesulfonamide

A suspension of 10.0 g (31.2 mmol) of material from Preparation 39, 11.2 g (124.8 mmol) of copper (I) cyanide and 23.8 g (124.8 mmol) of copper (I) iodide in 230 mL of dry dimethylformamide was heated to 140° C. for 16 hours, cooled to ambient temperature and concentrated in vacuo. The residue was suspended in 200 mL of ethyl acetate, filtered through celite and concentrated in vacuo. Chromatography (500 g of silica gel, 35% ethyl acetate/hexane) of the residue afforded 6.4 g (77%) of the title compound.

Analysis calculated for $C_{13}H_{18}N_2O_2S$: %C, 58.62; %H, 6.81; %N, 10.51. Found: %C, 58.44; %H, 6.64; %N, 10.23.

Mass Spectrum: M=266.

EXAMPLE 54

N-2-(4-(5-bromo-[1,2,4]oxadiazol-3-yl)phenyl)propyl 2-propanesulfonamide

A suspension of 2.0 g (7.5 mmol) of material from Example 53, 0.8 g (3.8 mmol) of material from Preparation 45 and 1.3 g (12.0 mmol) in 3 mL of toluene was heated to 90° C. for 7 hours, cooled and diluted with 10 mL of ethyl acetate. The mixture was washed once with 10 mL of water, the organic layer was separated and the aqueous layer was extracted three times with 5 mL each of ethyl acetate. The combined organics were dried (MgSO4), filtered and concentrated in vacuo. Chromatography (150 g of silica gel, 30% ethyl acetate/hexane) of the residue afforded a solid which was recrystallized from ethyl ether to afford 0.06 g (4%) of the title compound.

Analysis calculated for $C_{14}H_{18}N_2BrO_3S$: %C, 43.31; %H, 4.67; %N, 10.82. Found: %C, 43.58; %H, 4.65; %N, 10.76.

Mass Spectrum: M−1=387.

EXAMPLE 55

N-2-(4-(2-furyl)phenyl)propyl 2-propanesulfonamide

To a solution of 0.5 g (1.6 mmol) of material from Example 27 and 0.6 g (1.7 mmol) of 2-(tributylstannyl)-furan in 5 mL of dioxane was added 0.1 g (0.1 mmol) of tetrakis(triphenylphosphine)palladium (0). The mixture was heated to reflux for 16 hours, cooled to ambient temperature and diluted with 5 mL of ethyl ether. The mixture was washed once with 5 mL of saturated aqueous potassium fluoride, the organic layer was separated and the aqueous portion was extracted three times with 5 mL each of ethyl ether. The combined organics were dried (MgSO4), filtered and concentrated in vacuo. Chromatography (25 g of silica gel, 25% ethyl acetate/hexane) of the residue afforded a yellow oil which was recrystallized from ethyl ether/hexane to afford 0.2 g (51%) of the title compound.

Analysis calculated for $C_{16}H_{21}NO_3S$: %C, 62.51; %H, 6.89; %N, 4.56. Found: %C, 62.73; %H, 6.90; %N, 4.31.

Mass Spectrum: M=307.

EXAMPLE 56

N-2-(4-(4-(2-N',N'-dimethylaminosulfonamido)ethyl)phenyl)phenyl)propyl 2-propanesulfonamide The title product was prepared from N,N-dimethylsulfamoyl chloride as described in Example 51.

Analysis calculated for $C_{22}H_{33}N_3O_4S_2$: %C, 56.50; %H, 7.11; %N, 8.99. Found: %C, 56.21; %H, 7.20; %N, 8.71.

Mass Spectrum: M=467.

EXAMPLE 57

N-2-(4-(2-(4,5-dihydro)thiazolyl)phenyl)propyl 2-propanesulfonamide

A solution of 0.2 g (0.8 mmol) of material from Example 53 and 0.1 g (1.5 mmol) of 2-aminoethanethiol in 5 mL of ethanol was heated to reflux for 16 hours, cooled to ambient temperature and concentrated in vacuo. Chromatography (25 g of silica gel, 50% ethyl acetate/hexane) of the residue afforded 0.2 g (86%) of the title compound.

Analysis calculated for $C_{15}H_{22}N_2O_2S_2$: %C, 55.18; %H, 6.79; %N, 8.58. Found: %C, 55.03; %H, 6.73; %N, 8.37.

Mass Spectrum: M=326.

EXAMPLE 58

N-2-(4-(4-cyanophenyl)phenyl)propyl 2-proranesulfonamide

To a degassed solution of 4.0 g (12.4 mmol) of material from Example 27, 2.0 g (13.6 mmol) of material from Preparation 42 and 1.9 g (13.6 mmol) of potassium carbonate in 73 mL of 75% dioxane/water was added 0.7 g (0.6 mmol) of tetrakis(triphenylphosphine)palladium (0). The mixture was heated to 100° C. for 16 hours, cooled to ambient temperature, diluted with 30 mL of water and extracted three times with 35 mL each of ethyl ether. The combined organics were dried (MgSO4), filtered and concentrated in vacuo. Chromatography (250 g of silica gel, 35% ethyl acetate/hexane) of the residue afforded 2.3 g (56%) of the title compound as a pale yellow solid. Recrystallization of 0.16 g from chorobutane afforded 0.12 g of the pure title compound.

Analysis calculated for $C_{19}H_{22}N_2O_2S$: %C, 66.64; %H, 6.48; %N, 8.18. Found: %C, 66.86; %H, 6.42; %N, 8.09.

Mass Spectrum: M=342.

EXAMPLE 59

N-2-(4-(4-t-butoxycarbonylaminomethyl)-phenyl)phenyl)propyl 2-propanesulfonamide A. N-2-(4-(4-aminomethylphenyl)phenylpropyl 2-propanesulfonamide hydrochloride: A solution of 2.2 g (6.4 mmol) of material from Example 58 in 70 mL of ethanol and 3 mL of 1 N hydrochloric acid was hydrogenated in the presence of 0.2 g of 5% palladium on carbon at ambient temperature and 60 p.s.i. for 16 hours. The mixture was filtered through celite and concentrated in vacuo. To the residue was added 4 mL of 1 N hydrochloric acid and the mixture was concentrated in vacuo. The residue was dissolved in 10 mL of ethanol and the mixture was concentrated in vacuo. The residue was suspended in 50 mL of ethyl acetate and stirred for one hour, filtered and dried in vacuo to afford 1.7 g (75%) of the title compound.

B. To a suspension of 1.1 g (3.3 mmol) in 10 mL of dichloromethane was added 0.5 mL (3.6 mmol) of triethylamine and the mixture was stirred for 15 minutes. To the mixture was added 0.7 g (3.3 mmol) of di-tert-butyl dicarbonate and the mixture was stirred for 16 hours at ambient temperature. The mixture was washed once with 5 mL of 10% aqueous sodium bisulfate, the organic layer was separated and the aqueous layer was extracted two times with 5mL each of dichloromethane. The combined organics were dried ($Na_2SO_4$), filtered and concentrated in vacuo. Chromatography (75 g of silica gel, 30% ethyl acetate/hexane) of the residue afforded 0.5 g (32%) of the title compound.

Analysis calculated for $C_{24}H_{34}N_2O_4S$: %C, 64.55; %H, 7.67; %N, 6.27. Found: %C, 64.70; %H, 7.69; %N, 6.39.

Mass Spectrum: M=446.

EXAMPLE 60

N-2-(4-(4-aminomethyl)phenyl)phenyl)propyl 2-propanesulfonamide, trifluoroacetic acid salt A solution of 0.5 g (1.0 mmol) of material from Example 59 in 5 mL of 20% trifluoroacetic acid/dichloromethane was stirred at ambient temperature for two hours. The mixture was concentrated in vacuo dissolved in 5 mL of dichloromethane and washed with 5 mL of saturated aqueous sodium bicarbonate. The organic layer was separated and the aqueous layer was extracted three times with 5 mL each of dichloromethane. The combined organics were dried ($Na_2SO_4$), filtered and concentrated in vacuo. To the residue was added 4 mL dichloromethane and the resulting precipitate was filtered, rinsed with ethyl ether and dried in vacuo at 60° C. to afford 0.2 g (49%) of the title compound.

Analysis calculated for $C_{19}H_{26}N_2O_2S \cdot C_2HO_2F_3$: %C, 54.77; %H, 5.91; %N, 6.08. Found: %C, 54.70; %H, 5.95; %N, 6.11.

Mass Spectrum: M=346.

EXAMPLE 61

N-2-(4-(2-thienyl)phenyl)propyl 2-propanesulfonamide

To a solution of 0.5 g (1.6 mmol) of material from Example 27, 0.3 g (2.3 mmol) of thiophene-2-boronic acid and 0.3 g (2.3 mmol) of potassium carbonate in 7 mL of dioxane and 2 mL of water was added 0.1 g (0.1 mmol) of tetrakis(triphenylphosphine)palladium (0). The mixture was heated to 100° C. for 16 hours cooled to ambient temperature, diluted with 5 mL of water and extracted three times with 5 mL each of ethyl ether. The combined organics were dried (MgSO4), filtered and concentrated in vacuo. The residue was recrystallized from ethyl ether, filtered and dried in vacuo to afford 0.2 g (47%) of the title compound.

Analysis calculated for $C_{16}H_{21}NO_2S_2$: %C, 59.41; %H, 6.54; %N, 4.33. Found: %C, 59.36; %H, 6.44; %N, 4.11.

Mass Spectrum: M=323.

EXAMPLE 62

N-2-(4-(4-(1-hydroxy-2-methanesulfonamidoethyl)phenyl)phenyl)propyl 2-propanesulfonamide A solution of 0.3 g (0.5 mmol) of material from Preparation 44 (Step D) in 3.5 mL of 14% trifluoroacetic acid/dichloromethane was stirred at ambient temperature for four hours. 0.5 mL of trifluoroacetic acid was added and the mixture was heated to 50° C. for two hours. The mixture was cooled to ambient temperature and concentrated in vacuo. The residue was dissolved in 5 mL of dichloromethane and washed once with 5 mL of saturated aqueous sodium bicarbonate. The organic layer was separated and the aqueous layer was extracted three times with 5 mL each of dichloromethane. The combined organics were dried ($Na_2SO_4$), filtered and concentrated in vacuo. Chromatography (10 g of silica gel, 50% ethyl acetate/hexane) of the residue afforded 0.1 g (51%) of the title compound.

Analysis calculated for $C_{21}H_{30}N_2O_5S_2 \cdot 0.05\ CHCl_3$: %C, 54.89; %H, 6.58; %N, 6.08. Found: %C, 54.66; %H, 6.79; %N, 6.27.

Mass Spectrum: M=454.

EXAMPLE 63

N-2-(4-(5-tetrazolyl)phenyl)propyl 2-propanesulfonamide 0.2 g (0.8 mmol) of material from Example 53 and 0.5 g (1.5 mmol) of azidotributylstannane were heated to 80° C. for 72 hours. The mixture was cooled to ambient temperature, 5 mL of a saturated methanolic HCl solution was added, the mixture stirred for 30 minutes and was concentrated in vacuo. The residue was dissolved in 10 mL of acetonitrile and extracted four times with 5 mL each of hexane. The acetonitrile layer was concentrated in vacuo and the resulting solid was suspended in 10 mL of ethyl ether, filtered and dried in vacuo at 60° C. to afford 0.2 g (89%) of the title compound.

Analysis calculated for $C_{13}H_{19}N_5O_2S$: %C, 50.47; %H, 6.19; %N, 22.64. Found: %C, 50.19; %H, 6.11; %N, 22.54.

Mass Spectrum: M+1=310.

EXAMPLE 64

N-2-(4-(5-(2-methyl)tetrazolyl)phenyl)propyl 2-propanesulfonamide

A solution of 0.1 g (0.3 mmol) of material from Example 63, 0.07 g (0.5 mmol) of potassium carbonate and 0.03 mL (0.4 mmol) of methyl iodide in 2 mL of N,N-dimethylformamide was heated to 80° C. for 16 hours. The mixture was cooled to ambient temperature, diluted with 10 mL of water and extracted four times with 5 mL each of dichloromethane. The combined organics were dried ($Na_2SO_4$), filtered and concentrated in vacuo. Chromatography (10 g of silica gel, 25% ethyl acetate/-hexane) of the residue afforded 0.05 g (48%) of the title compound.

Analysis calculated for $C_{14}H_{21}N_5O_2S$: %C, 51.99; %H, 6.54; %N, 21.65. Found: %C, 52.28; %H, 6.54; %N, 21.83.

Mass Spectrum: M=323.

EXAMPLE 65

N-2-(4-(2-thiazolyl)phenyl)propyl 2-propanesulfonamide

A solution of 0.7 g (2.1 mmol) of material from Preparation 39, 0.5 g (2.2 mmol) of material from Preparation 46 and 0.1 g (0.1 mmol) of tetrakis-(triphenylphosphine) palladium(0) in 6 mL of dioxane was heated to 100° C. for 16 hours. The mixture was cooled to ambient temperature, diluted with 10 mL of ethyl ether and washed once with 10 mL of saturated aqueous potassium fluoride. The organic layer was separated and the aqueous layer was extracted three times with 5 mL each of ethyl ether. The combined organics were dried ($MgSO_4$), filtered and concentrated in vacuo. Chromatography (30 g of silica gel, 45% ethyl acetate/hexane) of the residue afforded an oil which was crystallized from ethyl ether, filtered and dried in vacuo at 60° C. to afford 0.3 g (41%) of the title compound.

Analysis calculated for $C_{15}H_{20}N_2O_2S_2$: %C, 55.53; %H, 6.21; %N, 8.63. Found: %C, 55.75; %H, 6.29; %N, 8.63.

Mass Spectrum: M=324.

EXAMPLE 66

N-2-(4-(2-(4S-methoxycarbonvyl4,5-dihydro) thiazolyl)phenyl)propyl 2-propanesulfonamide A solution of 0.3 g (0.9 mmol) of material from Example 53, 0.3 g (1.9 mmol) of L-cysteine methyl ester hydrochloride and 0.3 mL (1.9 mmol) of triethylamine in 5 mL of ethanol was heated to reflux for 16 hours. The mixture was cooled to ambient temperature and concentrated in vacuo. The residue was dissolved in 5 mL of ethyl acetate and washed once with 5 mL of water. The organic layer was separated and the aqueous layer was extracted three times with 5 mL each of ethyl acetate. The combined organic were dried ($MgSO_4$), filtered and concentrated in vacuo. Chromatography (10 g of silica gel, 45% ethyl acetate/hexane) of the residue afforded 0.05 g (15%) of the title compound.

Mass Spectrum: M=384.

EXAMPLE 67

N-2-(4-(2-(4R-methoxycarbonvyl4,5-dihydro) thiazolyl)phenyl)propyl 2-propanesulfonamide A solution of 0.3 g (0.9 mmol) of material from Example 53, 0.2 g (1.4 mmol) of D-cysteine methyl ester hydrochloride and 0.2 mL (1.4 mmol) of triethylamine in 5 mL of ethanol was heated to reflux for 16 hours. To the mixture was added 0.16 g (0.9 mmol) of D-cysteine methyl ester hydrochloride and 0.14 mL (0.9 mmol) of triethylamine and reflux was continued for 7 hours. The mixture was cooled to ambient temperature and concentrated in vacuo. The residue was dissolved in 5 mL of ethyl acetate and washed once with 5 mL of water. The organic layer was separated and the aqueous layer was extracted three times with 5 mL each of ethyl acetate. The combined organic were dried ($MgSO_4$), filtered and concentrated in vacuo. Chromatography (10 g of silica gel, 45% ethyl acetate/hexane) of the residue afforded 0.04 g (11%) of the title compound.

Analysis calculated for $C_{17}H_{24}N_2O_4S_2$: %C, 53.10; %H, 6.29; %N, 7.29. Found: %C, 52.99; %H, 6.35; %N, 7.49.

Mass Spectrum: M=384.

EXAMPLE 68

N-(2-(4-(4-(2-(2-propane)sulfonamido)ethyl)phenyl) phenyl)propyl 2-propanesulfonamide To a solution of 0.1 g (0.3 mmol) of material from Example 50 and 0.07 mL (0.5 mmol) of triethylamine in 1 mL of dichloromethane was added 0.04 mL (0.3 mmol) of isopropylsulfonyl chloride. The mixture was stirred at ambient temperature for 16 hours. The mixture was washed once with 1.5 mL of 10% aqueous sodium bisulfate, the organic layer was separated and the aqueous layer was extracted two times with 1 mL each of dichloromethane. The combined organics were dried ($Na_2SO_4$), filtered and concentrated in vacuo. Chromatography (10 g of silica gel, 50% ethyl acetate/-hexane) of the residue afforded 0.05 g (39%) of the title compound.

Analysis calculated for $C_{23}H_{34}N_2O_4S_2$: %C, 59.20; %H, 7.34; %N, 6.00. Found: %C, 59.08; %H, 7.33; %N, 5.76.

Mass Spectrum: M=466.

EXAMPLE 69

N-2-(4-(5-formylthien-3-yl)phenyl)propyl 2-propanesulfonamide

To a degassed solution of 0.4 g (0.8 mmol) of material from Preparation 40 and 0.09 mL (0.8 mmol) of 4-bromo-2-thiophenecarboxaldehyde in 3 mL of dioxane was added 0.05 g (0.04 mmol) of tetrakis(triphenylphosphine)-palladium(0). The mixture was heated to 100° C. for 16 hours, cooled to ambient temperature and diluted with 3 mL of ethyl acetate. The mixture was washed once with 3 mL of saturated aqueous potassium fluoride. The organic layer was separated and the aqueous layer was extracted three times with 3 mL each of ethyl acetate. The combined organics were dried ($MgSO_4$), filtered and concentrated in vacuo. Chromatography (25 g silica gel, 35% ethyl acetate/-hexane) of the residue afforded a solid which was suspended in ethyl ether, filtered and dried in vacuo to afford 0.1 g (42%) of the title compound.

Analysis calculated for $C_{17}H_{21}NO_3S_2$: %C, 58.09; %H, 6.02; %N, 3.99. Found: %C, 58.29; %H, 6.04; %N, 3.71.

Mass Spectrum: M=351.

EXAMPLE 70

N-2-(4-(5-hydroxymethylthien-3-yl)phenyl)propyl 2-propanesulfonamide

To solution of 0.09 g (0.3 mmol) of material from Example 69 in 2 mL of ethanol was added 0.01 g (0.3 mmol) of sodium borohydride. The mixture was stirred at ambient temperature for 16 hours and concentrated in vacuo. The residue was partitioned between 5 mL of ethyl acetate and 5 mL of water. The organic layer was separated and the aqueous layer was extracted three times with 3 mL each of ethyl acetate. The combined organics were dried ($MgSO_4$), filtered and concentrated in vacuo. Chromatography (1 g silica gel, 50% ethyl acetate/hexane) of the residue afforded 0.06 g (69%) of the title compound.

Mass Spectrum: M=353.

EXAMPLE 71

N-2-(4-(4-(1-hydroxyethyl)phenyl)phenyl)propyl 2-propanesulfonamide

To a solution of 0.2 g (0.4 mmol) of material from Example 45 in 3 mL of tetrahydrofuran at ambient temperature was added 0.3 mL (0.9 mmol) of a 3.0M solution of methylmagnesium bromide in ethyl ether. The mixture was stirred for 16 hours, diluted with 5 mL of water and extracted four times with 5 mL each of ethyl acetate. The combined organics were dried ($MgSO_4$), filtered and concentrated in vacuo. Chromatography (10 g silica gel, 45% ethyl acetate/hexane) of the residue afforded 0.1 g (74%) of the title compound.

Analysis calculated for $C_{20}H_{27}NO_3S \cdot 0.2CHCl_3$: %C, 62.96; %H, 7.11; %N, 3.63. Found: %C, 63.31; %H, 7.02; %N, 3.62.

Mass Spectrum: M=361.

EXAMPLE 72

N-2-(4-(4-(1-hydroxypropyl)phenyl)phenyl)propyl 2-propanesulfonamide

To a solution of 0.3 g (0.7 mmol) of material from Example 45 in 4 mL of tetrahydrofuran at ambient temperature was added 0.5 mL (1.5 mmol) of a 3.0M solution of ethylmagnesium bromide in ethyl ether. The mixture was stirred for 16 hours, diluted with 5 mL of half saturated brine and extracted four times with 5 mL each of ethyl acetate. The combined organics were dried ($MgSO_4$), filtered and concentrated in vacuo. Chromatography (15 g silica gel, 50% ethyl acetate/hexane) of the residue afforded 0.1 g (42%) of the title compound.

Analysis calculated for $C_{21}H_{29}NO_3S$: %C, 67.17; %H, 7.78; %N, 3.73. Found: %C, 66.95; %H, 7.69; %N, 3.59.

Mass Spectrum: M=375.

EXAMPLE 73

N-2-(4-4-carboxyphenyl)phenyl)propyl 2-propanesulfonamide

To a degassed solution of 1.0 g (3.1 mmol) of material from Preparation 39, 0.8 g (4.7 mmol) of 4-carboxyphenylboronic acid and 0.7 g (4.7 mmol) of potassium carbonate in 20 mL of 75% dioxane/water was added 0.2 g (0.2 mmol) of tetrakis(triphenylphosphine)-palladium (0). The mixture was heated to 100° C. for 16 hours, cooled to ambient temperature and diluted with 15 mL of 10% aqueous sodium bisulfate. The mixture was extracted three times with 20 mL each of ethyl acetate. The combined organics were dried ($MgSO_4$), filtered and concentrated in vacuo. Recrystallization of the residue from chlorobutane afforded 0.4 g (37%) of the title compound. A 0.1 g sample was recrystallized to afford 0.07 g of pure title compound.

Analysis calculated for $C_{19}H_{23}NO_4S$: %C, 63.14; %H, 6.41; %N, 3.88. Found: %C, 63.25; %H, 6.42; %N, 3.79.

Mass Spectrum: M=361.

EXAMPLE 74

N-2-(4-(4-carbamoylphenyl)phenyl)propyl 2-propanesulfonamide

To a 0° C. solution of 0.3 g (0.9 mmol) of material from Example 73 and 0.1 mL (0.9 mmol) of 4-methyl-morpholine in 5 mL of dichloromethane was added 0.1 mL (0.9 mmol) of isobutylchloroformate and the mixture was stirred at 0° C. for 30 minutes. One third of the mixture was added to 2 mL of 2.0 M ammonia in methanol at 0° C. and the cooling bath was removed. After 20 minutes, the resulting solid was filtered and dried in vacuo at 60° C. to afford 0.034 g (33%) of the title compound.

Analysis calculated for $C_{19}H_{24}N_2O_3$: %C, 63.31; %H, 6.71; %N,7.77. Found: %C, 63.68; %H, 6.85; %N, 7.61.

Mass Spectrum: M=360.

EXAMPLE 75

N-2-(4-(4-methylcarbamoylphenyl)phenyl)propyl 2-propanesulfonamide

To a 0° C. solution of 0.9 g (2.4 mmol) of material from Example 73 and 0.3 mL (2.5 mmol) of 4-methyl-morpholine in 5 mL of dichloromethane was added 0.3 mL (2.5 mmol) of isobutylchloroformate and the mixture was stirred at 0° C. for 30 minutes. To the mixture was added 10 mL of 40% aqueous methylamine at 0° C. and the cooling bath was removed. After one hour, 10 mL of water was added, the organic layer was separated and the aqueous layer was extracted two times with 5 mL each of dichloromethane. The combined organics were dried ($MgSO_4$), filtered and concentrated in vacuo. Recrystallization from methanol/chlorobutane afforded 0.4 g (44%) of the title compound.

Analysis calculated for $C_{20}H_{26}N_2O_3S$: %C, 64.14; %H, 7.00; %N, 7.48. Found: %C, 63.97; %H, 6.92; %N, 7.33.

Mass Spectrum: M=374.

EXAMPLE 76

N-2-(4-(4-dimethylcarbamoylphenyl)phenyl)propyl 2-propanesulfonamide

To a 0° C. solution of 0.3 g (0.9 mmol) of material from Example 73 and 0.1 mL (0.9 mmol) of 4-methyl-morpholine in 5 mL of dichloromethane was added 0.1 mL (0.9 mmol) of isobutylchloroformate and the mixture was stirred at 0° C. for 30 minutes. One third of the mixture was added to 2 mL of 2.0 M dimethylamine in tetra-hydrofuran at 0° C. and the cooling bath was removed. After 25 minutes, the mixture was diluted with 5 mL of ethyl acetate and washed once with 5 mL of water. The organic layer was separated and the aqueous layer was extracted three times with 2 mL each of ethyl acetate. The combined organics were dried ($MgSO_4$), filtered and concentrated in vacuo. The residue was crystallized from ethyl ether, filtered and dried in vacuo at 60° C. to afford 0.04 g (36%) of the title compound.

Analysis calculated for $C_{21}H_{28}N_2O_3S$: %C, 64.92; %H, 7.26; %N,7.21. Found: %C, 64.84; %H, 7.19; %N, 6.92.

Mass Spectrum: M=388.

EXAMPLE 77

N-2-(4-(4-acetylphenyl)phenyl)propyl 2-propanesulfonamide

To a degassed solution of 1.0 g (3.1 mmol) of material from Preparation 39, 0.8 g (4.7 mmol) of 4-acetylphenylboronic acid and 0.7 g (4.7 mmol) of potassium carbonate in 20 mL of 75% dioxane/water was added 0.2 g (0.2 mmol) of tetrakis(triphenylphosphine)palladium (0). The mixture was heated to 100° C. for 4.5 hours, cooled to ambient temperature and diluted with 15 mL of water. The resulting solid was filtered, dried and recrystallized from chlorobutane to afford 0.7 g (65%) of the title compound.

Analysis calculated for $C_{20}H_{25}NO_3S$: %C, 66.82; %H, 7.01; %N, 3.90. Found: %C, 66.95; %H, 7.16; %N, 3.63.

Mass Spectrum: M=359.

EXAMPLE 78

N-2-(4-(2-(5-formyl)thienyl)phenyl)propyl 2-propanesulfonamide

To a degassed solution of 0.4 g (0.8 mmol) of material from Preparation 40 and 0.09 mL (0.8 mmol) of 5-bromo-2-thiophenecarboxaldehyde in 3 mL of dioxane was added 0.05 g (0.04 mmol) of tetrakis(triphenylphosphine)-palladium(0). The mixture was heated to 100° C. for 16 hours, 0.04 mL (0.4 mmol) of 5-bromo-2-thiophene-carboxaldehyde was added and heating was continued for 6 hours. The mixture was cooled to ambient temperature and concentrated in vacuo. Chromatography (25 g silica gel, 35% ethyl acetate/hexane) of the residue afforded a solid which was suspended in ethyl ether, filtered and dried in vacuo to afford 0.06 g (24%) of the title compound.

Analysis calculated for $C_{17}H_{21}NO_3S_2$: %C, 58.09; %H, 6.02; %N, 3.99. Found: %C, 58.22; %H, 6.07; %N, 3.69.

Mass Spectrum: M=351.

EXAMPLE 79

N-2-(4-(2-(5-hydroxymethyl)thienyl)phenyl )propyl 2-propanesulfonamide

To a solution of 0.03 g (0.08 mmol) of material from Example 78 in 1 mL ethanol was added 0.003 g (0.08 mmol) of sodium borohydride. The mixture was stirred at ambient temperature for 2 hours, concentrated in vacuo and partitioned between 2 mL of ethyl acetate and 2 mL of water. The organic layer was separated and the aqueous portion was extracted three times with 1 mL each of ethyl acetate. The combined organics were dried (MgSO4), filtered and concentrated in vacuo. Chromatography (1 g of silica gel, 35% ethyl acetate/hexane) of the residue afforded 0.02 g (64%) of the title compound.

Analysis calculated for $C_{17}H_{23}NO_3S_2 \cdot 0.05CHCl_3$: %C, 56.97; %H, 6.46; %N, 3.90. Found: %C, 57.13; %H, 6.34; %N, 3.75.

Mass Spectrum: M=353.

EXAMPLE 80

N-2-(4-(2-(5-methoxycarbonyl)thiazolyl)phenyl) propyl 2-propanesulfonamide

To a 0° C. solution of 2.0 g (5.2 mmol) of material from Example 66 and 0.9 mL (5.8 mmol) of 1,8-diaza-bicyclo [5.4.0]undec-7-ene in 15 mL dichloromethane was added 0.5 mL (5.8 mmol) of bromotrichloromethane dropwise over 8 minutes. The mixture was stirred at 0° C. for 2 hours and washed once with 10 mL of saturated aqueous ammonium chloride. The organic layer was separated and the aqueous layer was extracted two times with 10 mL each of ethyl acetate. The combined organics were dried ($MgSO_4$), filtered and concentrated in vacuo. Chromatography (100 g of silica gel, 35% ethyl acetate/hexane) of the residue afforded 1.5 g (76%) of the title compound.

Analysis calculated for $C_{17}H_{22}N_2O_4S_2$: %C, 53.38; %H, 5.80; %N, 7.32. Found: %C, 53.08; %H, 5.94; %N, 7.18.

Mass Spectrum: M=382.

EXAMPLE 81

N-2-(4-(2-aminophenyl)phenyl)propyl 2-propanesulfonamide

To a degassed solution of 0.5 g (0.9 mmol) of material from Preparation 40 and 0.2 g (0.9 mmol) of 2-bromoanitine in 3 mL of toluene was added 0.06 g (0.05 mmol) of tetrakis(triphenylphosphine)palladium(0). The mixture was heated to 100° C. for 16 hours whereupon 0.03 g (0.03 mmol) of tetrakis(triphenylphosphine)palladium(0) was added and heating was continued for 16 hours. The mixture was cooled to ambient temperature and chromatographed (25 g silica gel, 35% ethyl acetate/-hexane) to afford an oil which was crystallized from chlorobutane/hexane to afford 0.06 g (20%) of the title compound.

Analysis calculated for $C_{18}H_{24}N_2O_2S$: %C, 65.03; %H, 7.28; %N, 8.43. Found: %C, 65.17; %H, 7.40; %N, 8.29.

Mass Spectrum: M=332.

EXAMPLE 82

N-2-(4-(4-phenyl)phenyl)propyl 2-propanesulfonamide

To a degassed solution of 0.5 g (1.6 mmol) of material from Preparation 39, 0.3 g (2.3 mmol) of phenylboronic acid and 0.3 g (2.3 mmol) of potassium carbonate in 9 mL of 7: dioxane/water was added 0.09 g (0.08 mmol) of tetrakis (triphenylphosphine)palladium(0). The mixture was heated to 100° C. for 16 hours, cooled to ambient temperature and diluted with 5 mL of water. The mixture was extracted three times with 5 mL each of ethyl acetate. The combined organics were dried ($MgSO_4$), filtered and concentrated in vacuo. Chromatography (25 g of silica gel, 25% ethyl acetate/hexane) of the residue afforded 0.4 g (71%) of the title compound.

Analysis calculated for $C_{18}H_{23}NO_2S$: %C, 68.14; %H, 7.30; %N, 4.41. Found: %C, 67.81; %H, 7.23; %N, 4.61.

Mass Spectrum: M=317.

EXAMPLE 83

N-2-(4-(2-(5-carboxy)thiazolyl)phenyl)propyl 2-propanesulfonamide

To a solution of 1.4 g (3.7 mmol) of material from Example 80, in 25 mL of 4:1 methanol/tetrahydrofuran was added 4.1 mL (4.1 mmol) of 1 N aqueous sodium hydroxide. After 5 hours was added 1.0 mL (1.0 mmol) of 1 N aqueous sodium hydroxide. The mixture stirred for 16 hours and was concentrated in vacuo. The residue was dissolved in 25 mL of water and extracted once with ethyl ether. The organic layer was discarded and the aqueous layer was acidified to pH 2 with 10% aqueous sodium bisulfate. The aqueous layer was extracted four times with 25 mL each of ethyl acetate and the combined organics were dried ($MgSO_4$), filtered and concentrated in vacuo. The resulting solid was suspended in ethyl ether, filtered and dried in vacuo to afford 1.0 g (70%) of the title compound. A 0.2 g sample was recrystallized from methanol/ethyl acetate to afford 0.1 g of pure title compound.

Analysis calculated for $C_{16}H_{20}N_2O_2S_2$: %C, 52.15; %H, 5.47; %N, 7.60. Found: %C, 52.24; %H, 5.40; %N, 7.42.

Mass Spectrum: M=368.

EXAMPLE 84

N-2-(4-(4-(2-cyanoethenyl)phenyl)phenyl propyl 2-1propanesulfonamide

To a suspension of 0.4 g (10.4 mmol) of sodium hydride (washed three times with hexane) in 2 mL of tetrahydrofuran was added 1.6 mL (10.4 mmol) of diethyl cyanomethylphosphonate. The mixture was stirred at ambient temperature for 15 minutes. To the mixture was added a solution of 3.0 g (8.7 mmol) of material from Example 45 in 15 mL of tetrahydrofuran. After stirring for two hours, the mixture was diluted with 25 mL of water and extracted three times with 20 mL each of ethyl ether. The combined organics were dried ($MgSO_4$), filtered and concentrated in vacuo. Chromatography (150 g of silica gel, 35% ethyl acetate/hexane) of the residue gave a white solid which was suspended in ethyl ether, filtered and dried in vacuo to afford 2.5 g (79%) of the title compound.

Analysis calculated for $C_{21}H_{24}N_2O_2S$: %C, 68.45; %H, 6.56; %N, 7.60. Found: %C, 68.65; %H, 6.49; %N, 7.55.

Mass Spectrum: M=368.

EXAMPLE 85

N-2-(4-(3-(2-bromo)thienyl)phenyl)propyl 2-propanesulfonamide

To a solution of 0.1 g (0.3 mmol) of material from Example 28 in 0.5 mL of 1:1 chloroform/acetic acid was added a suspension of 0.06 g (0.3 mmol) of N-bromosuccinimide in 1 mL of 1:1 chloroform/acetic acid. The mixture was stirred at ambient temperature for one hour and diluted with 1.5 mL of water. The organic layer was separated, washed once with 1 N aqueous sodium hydroxide, dried ($MgSO_4$), filtered and concentrated in vacuo. The residue was dissolved in 1 mL of dichloromethane, filtered through a plug of silica gel eluting with 35% ethyl acetate/hexane and concentrated in vacuo to afford 0.1 g (72%) of the title compound.

Analysis calculated for $C_{16}H_{20}NO_2S_2$ Br: %C, 47.76; %H, 5.01; %N, 3.48. Found: %C, 48.02; %H, 5.22; %N, 3.48.

Mass Spectrum: M+2=404.

EXAMPLE 86

N-2-(4-(4-(2-(N-(t-butoxycarbonyl)methylsulfonamido)ethanoyl)-phenyl)phenyl)propyl 2-propanesulfonamide A. N-(4tri-n-butylstannylphenyl)carbonylmethyl-N-t-butoxycarbonyl-methanesulfonamide. To a degassed solution of 5.0 g (12.7 mmol) of material from Preparation 44 (Step B), 7.1 mL (14.0 mmol) of bis(tributyltin) and 2.0 mL (14.0 mmol) of triethylamine in 35 mL of toluene was added 0.7 g (0.6 mmol) of tetrakis(triphenylphosphine)palladium(0). The mixture was heated to reflux for 16 hours, cooled to ambient temperature and diluted with 35 mL of ethyl acetate. The mixture was washed once with 30 mL of 10% aqueous sodium bisulfate, the organic layer was separated and the aqueous layer was extracted three times with 15 mL each of ethyl acetate. The combined organics were dried ($MgSO_4$), filtered and concentrated in vacuo. Chromatography (200 g of silica gel, 5% ethyl acetate/hexane) of the residue afforded 2.2 g (28%) of the title compound.

Analysis calculated for $C_{26}H_{45}NO_5S$ Sn: %C, 51.84; %H, 7.53; %N, 2.33. Found: %C, 52.12; %H, 7.56; %N, 2.57.

Mass Spectrum: M+2=604.

B. To a degassed solution of 1.1 g (3.5 mmol) of material from Preparation 39, 2.1 g (3.5 mmol) of material from Step A in 10 mL of toluene was added 0.2 g (0.2 mmol) of tetrakis(triphenylphosphine)palladium(0). The mixture was heated to 92° C. for 16 hours, 0.2 g (0.2 mmol) of tetrakis(triphenylphosphine)palladium(0) was added and heating continued for four hours. The mixture was cooled to ambient temperature and diluted with 5 mL of ethyl acetate. 5 mL of saturated aqueous potassium fluoride was added and the mixture stirred for one hour. The mixture was filtered through diatomaceous earth, the organic layer was separated and the aqueous layer was extracted three times with 5 mL each of ethyl acetate. The combined organics were dried ($MgSO_4$), filtered and concentrated in vacuo. Chromatography (50 g of silica gel, 40% ethyl acetate/hexane) of the residue afforded a tan solid which was suspended in ethyl ether, filtered and dried in vacuo to afford 0.2 g (10%) of the title compound.

Analysis calculated for $C_{26}H_{36}N_2O_7S_2$: %C, 56.50; %H, 6.57; %N, 5.07. Found: %C, 56.56; %H, 6.73; %N, 5.18.

Mass Spectrum: M=552.

EXAMPLE 87

N-2-(4-(4-(2-methanesulfonamido)-ethanoyl)phenyl)phenyl)propyl 2-propanesulfonamide A solution of 0.2 g (0.3 mmol) of material from Example 86 in 2.5 mL of 20% trifluoroacetic acid/-dichloromethane was stirred at ambient temperature for 1.5 hours. The mixture was concentrated in vacuo, dissolved in 5 mL of dichloromethane and washed with 5 mL of saturated aqueous sodium bicarbonate. The organic layer was separated and the aqueous layer was extracted three times with 5 mL each of dichloromethane. The combined organics were dried ($Na_2SO_4$), filtered and concentrated in vacuo. Chromatography (10 g of silica gel, 60% ethyl acetate/hexane) of the residue afforded 0.1 g (60%) of the title compound.

Analysis calculated for $C_{21}H_{28}N_2O_5S_2$: %C, 55.73; %H, 6.24; %N, 6.19. Found: %C, 55.44; %H, 6.17; %N, 6.15.

Mass Spectrum: M=452.

EXAMPLE 88

N-2-(4-(4-(4-(1,1-dioxotetrahydro-1,2-thiazinyl)phenyl)phenyl)propyl 2-propanesulfonamide A solution of 0.1 g (0.4 mmol) of material from Preparation 49 and 0.2 g (0.4 mmol) of material from Preparation 40 in 2 mL of 20% dioxane/toluene was added 4 mg (0.02 mmol) of palladium(II)acetate and 9 mg (0.04 mmol) of triphenylphosphine. The mixture was heated to 100° C. for 16 hours and 0.1 g (0.2 mmol) of material from Preparation 40 was added. Heating was continued for 8 hours. The mixture was cooled to ambient temperature, diluted with 2 mL of ethyl acetate and 1 mL of saturated aqueous potassium fluoride was added. After stirring for one hour the organic layer was separated and the aqueous layer was extracted three times with 1 mL each of ethyl acetate. The combined organics were dried ($MgSO_4$), filtered and concentrated in vacuo. Chromatography (10 g of silica gel, 40% ethyl acetate/hexane) of the residue afforded 0.04 g (22%) of the title compound.

Analysis calculated for $C_{22}H_{30}N_2O_4S_2$: %C, 58.64; %H, 6.71; %N, 6.22. Found: %C, 58.34; %H, 6.77; %N, 6.06.

Mass Spectrum: M−1=449.

EXAMPLE 89

N-2-(4-(5-(3-benzyl)tetrazolyl)phenyl)propyl 2-propanesulfonamide

A solution of 0.2 g (0.7 mmol) of material from Example 63, 0.1 g (1.0 mmol) of potassium carbonate and 0.09 mL (0.7 mmol) of benzyl bromide in 4 mL of N,N-dimethylformamide was heated to 80° C. for 4 hours. The mixture was cooled to ambient temperature, diluted with 10 mL of water and extracted four times with 5 mL each of dichloromethane. The combined organics were dried ($Na_2SO_4$), filtered and concentrated in vacuo. Chromatography (20 g of silica gel, 35% ethyl acetate/hexane) of the residue afforded 0.2 g (79%) of the title compound.

Analysis calculated for $C_{20}H_{25}N_5O_2S$: %C, 60.13; %H, 6.31; %N, 17.53. Found: %C, 60.36; %H, 6.17; %N, 17.71.

Mass Spectrum: M+1=400.

EXAMPLE 90

N-2-(4-(2-(4,5-dihydro-4-methoxycarbonyl-5,5-dimethyl)thiazolyl)phenyl)propyl 2-propanesulfonamide A solution of 0.3 g (0.9 mmol) of material from Example 53, 0.5 g (2.4 mmol) of material from Preparation 50 and 0.3 mL (2.4 mmol) of triethylamine in 8 mL of ethanol was heated to reflux for 16 hours. The mixture was cooled to ambient temperature and concentrated in vacuo. The residue was dissolved in 10 mL of ethyl acetate and washed once with 10 mL of water. The organic layer was separated and the aqueous portion was extracted three times with 5 mL each of ethyl acetate. The combined organics were dried (MgSO$_4$), filtered and concentrated in vacuo. Chromatography (15 g of silica gel, 35% ethyl acetate/hexane) of the residue afforded 0.17 g (43%) of the title compound.

Analysis calculated for $C_{19}H_{28}N_2O_4S_2$: %C, 55.31; %H, 6.84; %N, 6.79. Found: %C, 55.35; %H, 6.95; %N, 6.64.

Mass Spectrum: M=412.

EXAMPLE 91

N-2-(4-(5-(2-ethyl)tetrazolyl)phenyl)propyl 2-propanesulfonamide

The title compound was prepared from the product of Example 63 as described in Example 64 with the exception that iodoethane was used instead of iodomethane.

Analysis calculated for $C_{15}H_{23}N_5O_2S$: %C, 53.39; %H, 6.87; %N, 20.75. Found: %C, 53.49; %H, 6.89; %N, 20.45.

Mass Spectrum: M+1=338.

EXAMPLE 92

N-2-(4-(5-(2-(2-propyl))tetrazolyl)phenyl)propyl 2-propanesulfonamide

The title compound was prepared from the product of Example 63 as described in Example 64 with the exception that 2-iodopropane was used instead of iodomethane.

Analysis calculated for $C_{16}H_{25}N_5O_2S$: %C, 54.68; %H, 7.17; %N, 19.93. Found: %C, 54.78; %H, 6.93; %N, 19.76.

Mass Spectrum: M+1=352.

EXAMPLE 93

N-2-(4-(5-(2-prop-3-enyl)tetrazolyl)phenyl)propyl 2-propanesulfonamide

The title compound was prepared from the product of Example 63 as described in Example 64 with the exception that allyl bromide was used instead of iodomethane.

Analysis calculated for $C_{16}H_{23}N_5O_2S$: %C, 54.99; %H, 6.63; %N, 20.04. Found: %C, 54.99; %H, 6.40; %N, 19.77.

Mass Spectrum: M+1=350.

EXAMPLE 94

N-2-(4-(4-aminophenyl)phenyl)propyl 2-propanesulfonamide

A. N-2-(4-(4-t-butoxycarbonylaminophenyl)phenyl)propyl 2-propane-sulfonamide: A degassed solution of 0.9 g (2.9 mmol) of material from Example 39, 1.4 g (2.8 mmol) of material from Preparation 51 and 0.2 g (0.1 mmol) of tetrakis(triphenylphosphine)palladium(0) in 10 mL of toluene was heated to reflux for 5 hours. The mixture was cooled to ambient temperature and concentrated in vacuo. Chromatography (100 g of silica gel, 30% ethyl acetate/hexane) of the residue afforded 0.15 g (12%) of the title compound.

Mass Spectrum: M=432.

B. A solution of 0.2 g (0.5 mmol) of material from Step A in 2.5 mL of 20% trifluoroacetic acid/-dichloromethane was stirred at ambient temperature for two hours. The mixture was concentrated in vacuo, dissolved in 2 mL of dichloromethane and washed once with 1 mL of saturated aqueous sodium bicarbonate. The organic layer was separated and the aqueous layer was extracted three times with 1 mL each of dichloromethane. The combined organics were dried (Na$_2$SO$_4$), filtered and concentrated in vacuo. The residue was crystallized from chlorobutane/hexane to afford 0.03 g (20%) of the title compound.

Analysis calculated for $C_{18}H_{24}N_2O_2S$: %C, 65.03; %H, 7.28; %N, 8.43. Found: %C, 65.11; %H, 7.52; %N, 8.23.

Mass Spectrum: M=350.

EXAMPLE 95

N-2-(4-(3-furyl)phenyl propyl 2-propanesulfonamide

To a solution of 0.8 g (2.6 mmol) of material from Preparation 39 and 1.0 g (2.9 mmol) of 3-(tributyl-stannyl) furan in 10 mL of dioxane was added 0.2 g (0.1 mmol) of tetrakis(triphenylphosphine)palladium (0). The mixture was heated to reflux for 4 hours, cooled to ambient temperature and diluted with 10 mL of water. The mixture was extracted three times with 10 mL each of ethyl ether. The combined organics were dried (MgSO$_4$), filtered and concentrated in vacuo. Chromatography (25 g of silica gel, 25% ethyl acetate/hexane) of the residue afforded a solid which was suspended in hexane, filtered and dried in vacuo to afford 0.3 g (42%) of the title compound.

Analysis calculated for $C_{16}H_{21}NO_3S$: %C, 62.51; %H, 6.89; %N, 4.56. Found: %C, 62.64; %H, 6.92; %N, 4.69.

Mass Spectrum: M=307.

EXAMPLE 96

N-2-(4-(2-(4-hydroxymethyl)thiazolyl)phenyl)propyl 2-propanesulfonamide

To a 0° C. solution of 0.8 g (2.0 mmol) of material from Example 83 in 6 mL of tetrahydrofuran was added 0.4 mL (4.1 mmol) of 10 M boranedimethylsulfide. The mixture was stirred at 0° C. for 30 minutes and allowed to warm to ambient temperature for 16 hours. To the mixture was slowly added 3 mL of saturated aqueous sodium bicarbonate. The mixture was diluted with 10 mL of water and extracted four times with 10 mL each of ethyl acetate. The combined organics were dried (MgSO$_4$), filtered and concentrated in vacuo. The residue was filtered through 5 g of silica gel and concentrated in vacuo. Chromatography (2 g of silica gel, 50% ethyl acetate/hexane) of the residue afforded 0.03 g (4%) of the title compound.

Analysis calculated for $C_{16}H_{22}N_2O_3S_2$. 0.05 CHCl$_3$: %C, 53.48; %H, 6.17; %N, 7.77. Found: %C, 53.31; %H, 6.46; %N, 7.93.

Mass Spectrum: M=354.

EXAMPLE 97

N-2-(4-(4-fluorophenyl)phenyl)propyl methanesulfonamide

To a degassed solution of 1.5 g (5.1 mmol) of material from Example 1, 1.1 g (7.7 mmol) of potassium carbonate and 1.1 g (7.7 mmol) of 4-fluorobenzeneboronic acid in 30 mL of toluene was added 0.2 g (0.3 mmol) of dichlorobis (triphenylphosphine)palladium (II). The mixture was heated to 100° C. for 16 hours and cooled to ambient temperature.

The mixture was diluted with 20 mL of ethyl acetate, filtered through diatomaceous earth and concentrated in vacuo. Chromatography (50 g of silica gel, 30% ethyl acetate/hexane) of the residue afforded a white solid which was suspended in ethyl ether, filtered and recrystallized from chlorobutane to afford 0.2 g (12%) of the title compound.

Field Desorption Mass Spectrum: M=307.

EXAMPLE 98

N-2-(4-(2,3-difluorophenyl)phenyl)propyl methanesulfonamide

To a solution of 0.4 g (0.8 mmol) of material from Preparation 52, 0.2 g (0.8 mmol) of 2,3-difluorophenyl trifluoromethanesulfonate, 0.1 g (2.3 mmol) of lithium chloride in 5 mL of toluene was added 0.03 g (0.04 mmol) of dichlorobis(triphenylphosphine)palladium (II). The mixture was heated to 100° C. for 16 hours and cooled to ambient temperature. The mixture was diluted with 5 mL of ethyl acetate and washed with 5 mL of water. The organic layer was separated and the aqueous layer was extracted three times with 5 mL each of ethyl acetate. The combined organics were dried ($MgSO_4$), filtered and concentrated in vacuo. Chromatography (50 g of silica gel, 25% ethyl acetate/hexane) of the residue afforded an oil which was crystallized from diethyl ether to afford 0.1 g (37%) of the title compound.

Analysis calculated for $C_{16}H_{17}NO_2SF_2$: %C, 59.06; %H, 5.27; %N, 4.30. Found: %C, 59.05; %H, 5.14; %N, 4.08.

Field Desorption Mass Spectrum: M=325.

EXAMPLE 99

N-2-(4-bromophenyl)propyl trifluoromethanesulfonamide

The title compound was prepared from the product of Preparation 2 as described in Preparation 39 with the exception that trifluoromethanesulfonyl chloride was used instead of isopropylsulfonyl chloride.

Analysis calculated for $C_{10}H_{11}NO_2SBrF_3$: %C, 34.70; %H, 3.20; %N, 4.05. Found: %C, 34.95; %H, 3.32; %N, 4.00.

Field Desorption Mass Spectrum: M+1=347.

EXAMPLE 100

N-2-(4-(2-formylphenyl)phenylpropyl methanesulfonamide

The title compound was prepared from the product of Example 1 as described in Example 97 with the exception that 2-formylbenzeneboronic acid was used instead of 4-fluorbenzeneboronic acid and tetrakis(triphenylphosphine)palladium (0) was used instead of dichlorobis-(triphenylphosphine)palladium (II).

Analysis calculated for $C_{17}H_{19}NO_3S$: %C, 64.33; %H, 6.03; %N, 4.41. Found: %C, 64.13; %H, 5.90; %N, 4.40.

Field Desorption Mass Spectrum: M=317.

EXAMPLE 101

N-2-(4-(2-methylphenyl)phenyl)propyl methanesulfonamide

The title compound was prepared from the product of Example 1 as described in Example 100 with the exception that 2-methylbenzeneboronic acid was used instead of 2-formylbenzeneboronic and 10 mL of water was added to the reaction mixture.

Analysis calculated for $C_{17}H_{21}NO_2S$: %C, 67.29; %H, 6.98; %N, 4.62. Found: %C, 67.11; %H, 7.18; %N, 4.53.

Field Desorption Mass Spectrum: M=303.

EXAMPLE 102

N-2-(4-(4-methoxyphenyl)phenyl)propyl methanesulfonamide

The title compound was prepared from the product of Example 1 as described in Example 6 with the exception that 4-methoxybenzeneboronic acid was used instead of 2-methoxybenzeneboronic acid.

Analysis calculated for $C_{17}H_{21}NO_3S$: %C, 63.92; %H, 6.63; %N, 4.39. Found: %C, 63.92; %H, 6.50; %N, 4.18.

Field Desorption Mass Spectrum: M=319.

EXAMPLE 103

N-2-(4-(3-thienyl)phenyl)propyl 2-propanesulfonamide

To a 0° C. solution of 3.1 g (14.4 mmol) of material from Preparation 53 (Step B) and 4.8 g (31.7 mmol) of 1,8-diazabicyclo[5.4.0]undec-7-ene in 50 mL of dichloromethane was added a solution of 2.8 g (15.8 mmol) of material from Preparation 54 in 10 mL of dichloromethane. The mixture was stirred at 0° C. for 30 minutes, the cooling bath was removed and the mixture stirred for one hour. The reaction mixture was washed once with 30 mL of 10% aqueous sodium bisulfate. The organic layer was separated and the aqueous layer was extracted three times with 10 mL each of dichloromethane. The combined organics were dried ($Na_2SO_4$), filtered and concentrated in vacuo. Chromatography (300 g of silica gel, 25% ethyl acetate/hexane) of the residue afforded 1.0 g (22%) of the title compound.

Analysis calculated for $C_{16}H_{19}NO_2S_2$: %C, 59.78; %H, 5.96; %N, 4.36. Found: %C, 59.90; %H, 6.10; %N, 4.26.

Field Desorption Mass Spectrum: M+1=322.

EXAMPLE 104

N-2-(4-(hydroxyiminoyl)phenyl)propyl 2-propanesulfonamide

A solution of 0.5 g (1.9 mmol) of material from Preparation 43 and 0.14 g (2.0 mmol) of hydroxylamine hydrochloride in 6 mL of ethyl alcohol was heated to reflux for 18 h. The mixture was cooled and concentrated in vacuo. The residue was partitioned between 5 mL of water and 5 mL of ethyl acetate. The organic layer was separated and the aqueous layer was extracted two times with 5 mL each of ethyl acetate. The combined organic extracts were dried ($MgSO_4$), filtered and concentrated in vacuo to afforded 0.4 g (74%) of the title compound.

Analysis calculated for $C_{13}H_{20}N_2O_3S$: %C, 54.91; %H, 7.09; %N, 9.85. Found: %C, 56.04; %H, 6.82; %N, 10.43.

Field Desorption Mass Spectrum: M=284.

EXAMPLE 105

N-2-(4-(3-(5-hydroxymethyl)isoxazolyl)phenyl) propyl 2-propanesulfonamide

To a solution of 0.3 g (1.0 mmol) of material from Example 104 and 0.1 g (2.0 mmol) of propargyl alcohol and 0.3 g (3.0 mmol) of potassium bicarbonate in 3 mL of ethyl acetate and 1 drop of water was added 0.1 g (1.0 mmol) of N-chlorosuccinimide. The mixture was stirred at room temperature for 18 hr and then 3 mL of water was added. The organic layer was separated and the aqueous layer was extracted three times with 3 mL each of ethyl acetate. The combined organic extracts were dried (MgSO$_4$), filtered and concentrated in vacuo. Chromatography (12 g of silica gel, 50% ethyl acetate/hexane) of the residue afforded 0.037 g (11%) of the title compound.

Analysis calculated for $C_{16}H_{22}N_2O_4S$: %C, 56.79; %H, 6.55; %N, 8.28. Found: %C, 51.97; %H, 5.93; %N, 10.96.

Field Desorption Mass Spectrum: M=338.

EXAMPLE 106

N-2-(4-(3-(5-methoxycarbonyl)isoxazolyl)phenyl) propyl 2-propanesulfonamide

A. N-2-(4-(1-hydroxy-2-chloroiminoyl)phenyl)propyl 2-propanesulfonamide: To a solution of 1.0 g (3.5 mmol) of material from Example 104 in 10 mL N,N-dimethylformamide was added 0.5 g (3.5 mmol) of N-chlorosuccinimide in small solid portions. The solution was stirred at room temperature for 3 h. The mixture was poured into 40 mL of ice and the aqueous layer was extracted three times with 10 mL each of ether. The combined organic extracts were dried (MgSO$_4$), filtered and concentrated in vacuo to afford 1.25 g (100%) of the title compound.

B. To a solution of 0.5 g (1.0 mmol) of material from Example 106A and 0.3 g (3.1 mmol) of methyl propiolate in 3 mL of ethyl acetate and 1 drop of water was added 0.5 g (4.7 mmol) of potassium bicarbonate. The mixture was stirred at room temperature for 18 hr and then 3 mL of water was added. The organic layer was separated and the aqueous layer was extracted three times with 3 mL each of ethyl acetate. The combined organic extracts were dried (MgSO$_4$), filtered and concentrated in vacuo. Chromatography (25 g of silica gel, 35% ethyl acetate/hexane) of the residue afforded 0.34 g (51%) of the title compound.

Analysis calculated for $C_{17}H_{22}N_2O_5S$: %C, 55.72; %H, 6.05; %N, 7.64. Found: %C, 55.95; %H, 6.24; %N, 7.37.

Field Desorption Mass Spectrum: M=366.

EXAMPLE 107

N-2-(4-(3-(5-carboxy)isoxazolyl)phenyl)propyl 2-propanesulfonamide

A solution of 0.3 g (0.8 mmol) of material from Example 106B in 3 mL of methyl alcohol and 1 mL (1 mmol) 1N sodium hydroxide was heated at 50° C. for 18 h. To the mixture was added 1 mL (1 mmol) 1N sodium hydroxide and the mixture was heated at 50° C. for 7 h. The mixture was cooled and concentrated in vacuo. The residue was partitioned between 3 mL of water and 3 mL of ether. The organic layer was separated and the aqueous layer was washed three times with 3 mL each of ether. The aqueous layer was acidified to pH=1 with conc. hydrochloric acid. The aqueous layer was extracted three times with 3 mL each of ether. The combined organic extracts were dried (MgSO$_4$), filtered and concentrated in vacuo to affored 0.11 g (39%) of the title compound.

Analysis calculated for $C_{16}H_{20}N_2O_5S$: %C, 54.53; %H, 5.72; %N, 7.95. Found: %C, 55.80; %H, 5.27; %N, 7.74.

Field Desorption Mass Spectrum: M=352.

EXAMPLE 108

N-2-(4-(3-(5-trimethylsilyl)isoxazolyl)phenyl)propyl 2-propanesulfonamide

To a solution of 0.5 g (1.6 mmol) of material from Example 106A and 0.3 g (3.1 mmol) of (trimethylsilyl) acetylene in 3 mL of ethyl acetate and 1 drop of water was added 0.5 g (4.7 mmol) of potassium bicarbonate. The mixture was stirred at room temperature for 18 hr and then 3 mL of water was added. The organic layer was separated and the aqueous layer was extracted three times with 3 mL each of ethyl acetate. The combined organic extracts were dried (MgSO$_4$), filtered and concentrated in vacuo. Chromatography (25 g of silica gel, 35% ethyl acetate/hexane) of the residue afforded 0.36 g (59%) of the title compound.

Analysis calculated for $C_{18}H_{28}N_2O_3SSi$: %C, 56.81; %H, 7.42; %N, 7.36. Found: %C, 57.63; %H, 7.41; %N, 7.52.

Field Desorption Mass Spectrum: M=380.

EXAMPLE 109

N-2-(4-(3-(5-acetyl)isoxazolyl)phenyl)propyl 2-propanesulfonamide

To a solution of 0.07 g (0.2 mmol) of material from Example 106A and 0.029 g (0.4 mmol) of 3-butyn-2-one in 3 mL of ethyl acetate and 1 drop of water was added 0.066 g (0.6 mmol) of potassium bicarbonate. The mixture was stirred at room temperature for 18 hr and then 3 mL of water was added. The organic layer was separated and the aqueous layer was extracted three times with 3 mL each of ethyl acetate. The combined organic extracts were dried (MgSO$_4$), filtered and concentrated in vacuo. Chromatography (12 g of silica gel, 35% ethyl acetate/hexane) of the residue afforded 0.04 g (57%) of the title compound.

Analysis calculated for $C_{17}H_{22}N_2O_4S$: %C, 58.27; %H, 6.33; %N, 7.99. Found: %C, 59.08; %H, 6.29; %N, 7.36.

Field Desorption Mass Spectrum: M=350.

EXAMPLE 110

N-2-(4-(3-(5-(N'-methylcarbamoyl))-isoxazolyl) phenyl)propyl 2-propanesulfonamide A solution of 0.1 g (0.28 mmol) of material from Example 107 and 0.03 g (0.3 mmol) N-methylmorpholine in 2 mL of dichloromethane was cooled to 0° C. A solution of 0.033 mL (0.3 mmol) of isobutylchloroformate in 1 mL of dichloromethane was added and the mixture was stirred at 0° C. for 30 min. The mixture was poured into 2 mL 40% methylamine and water at 0° C. and stirred for 30 min. The organic layer was separated and the aqueous layer was extracted three times with 3 mL each of ethyl acetate. The combined organic extracts were dried (MgSO$_4$), filtered and concentrated in vacuo. Chromatography (12 g of silica gel, 50% ethyl acetate/hexane) of the residue afforded 0.04 g (39%) of the title compound.

Analysis calculated for $C_{17}H_{23}N_3O_4S$: %C, 55.87; %H, 6.34; %N, 11.50. Found: %C, 55.97; %H, 6.28; %N, 11.20.

Field Desorption Mass Spectrum: M=365.

EXAMPLE 111

N-2-(4-(3-isoxazolyl)phenyl)propyl 2-propanesulfonamide

A solution of 0.3 g (0.79 mmol) of material from Example 108 and 0.079 mL of conc. ammonium hydroxide was heated at 100° C. for 2 h. To the mixture was added 2 drops of conc. ammonium hydroxide and the mixture was heated at 100° C. for 18 h. The mixture was cooled and partitioned between 5 mL of water and 5 mL of ether. The organic layer was separated and the aqueous layer was extracted three times with 5 mL each of ether. The combined organic extracts were dried ($MgSO_4$), filtered and concentrated in vacuo. Chromatography (12 g of silica gel, 35% ethyl acetate/hexane) of the residue afforded 0.038 g (16%) of the title compound.

Analysis calculated for $C_{15}H_{20}N_2O_3S$: %C, 58.42; %H, 6.54; %N, 9.08. Found: %C, 58.28; %H, 6.67; %N, 8.78.

Field Desorption Mass Spectrum: M=308.

EXAMPLE 112

N-2-(4-(3-(5-(2-hydroxy)ethyl)isoxazolyl)phenyl) propyl 2-propanesulfonamide

To a solution of 0.58 g (1.8 mmol) of material from Example 106A and 0.25 g (3.6 mmol) of 3-butyn-1-ol in 3 mL of ethyl acetate and 1 drop of water was added 0.54 g (5.4 mmol) of potassium bicarbonate. The mixture was stirred at room temperature for 18 hr and then 3 drops of 3-butyn-1-ol was added and stirred for 2 hr and then 3 mL of water was added. The organic layer was separated and the aqueous layer was extracted three times with 3 mL each of ethyl acetate. The combined organic extracts were dried ($MgSO_4$), filtered and concentrated in vacuo. Chromatography (25 g of silica gel, 75% ethyl acetate/hexane) of the residue afforded 0.24 g (38%) of the title compound.

Analysis calculated for $C_{17}H_{24}N_2O_4S$: %C, 57.93; %H, 6.86; %N, 7.95. Found: %C, 58.23; %H, 6.99; %N, 8.14.

Field Desorption Mass Spectrum: M=352.

EXAMPLE 113

N-2-(4-(5-(3-bromo)isoxazolyl)phenyl)propyl 2-propanesulfonamide

A. N-2-(4-ethynylphenyl)propyl 2-propanesulfonamide: To a solution of 2.0 g (6.2 mmol) of material from Preparation 39 and 2.0 g (6.2 mmol) of tri-n-butylstannylethyne in 20 mL of toluene was added 0.36 g (0.3 mmol) of tetrakis(triphenylphosphine)palladium(0). The mixture was heated at 90 ° C. for 18 h. The mixture was cooled and filtered through diatomaceous earth and rinsed with 20 mL ethyl acetate and concentrated in vacuo. Chromatography (100 g of silica gel, 35% ethyl acetate/hexane) of the residue afforded 0.3 g (18%) of the title compound.

B. To a solution of 0.3 g (1.1 mmol) of material from Example 113A and 0.1 g (0.5 mmol) of material from Preparation 45 in 2 mL of ethyl acetate and 1 drop of water was added 0.17 g (0.7 mmol) of potassium bicarbonate. The mixture was stirred at room temperature for 18 hr and then 0.1 g (0.5 mmol) of material from Preparation 45 was added and stirred for 5 hr and then 2 mL of water was added. The organic layer was separated and dried ($MgSO_4$), filtered and concentrated in vacuo. Chromatography (12 g of silica gel, 35% ethyl acetate/hexane) of the residue afforded 0.1 g (23%) of the title compound.

Analysis calculated for $C_{15}H_{19}BrN_2O_3S$: %C, 46.52; %H, 4.94; %N, 7.23. Found: %C, 46.73; %H, 5.00; %N, 6.94.

Field Desorption Mass Spectrum: M−1=386.

EXAMPLE 114

N-2-(4-(2-pyridyl)phenyl)propyl 2-propanesulfonamide

To a solution of 4.3 g (13.4 mmol) of material from Preparation 39 and 4.9 g (13.4 mmol) of 2-(tri-n-butylstannyl)pyridine in 10 mL of toluene was added 0.78 g (0.67 mmol) of tetrakis(triphenylphosphine)palladium(0). The mixture was heated at 90° C. for 18 h. Then 0.025 g (0.03 mmol) of bis(triphenylphosphine)palladium(II) chloride was added and the mixture was heated at 90° C. for 18 h. The mixture was cooled and concentrated in vacuo. Chromatography (400 g of silica gel, 50% ethyl acetate/hexane) of the residue afforded 4.3 g (98%) of the title compound.

Analysis calculated for $C_{17}H_{22}N_2O_2S*0.5H_2O$: %C, 62.35; %H, 7.08; %N, 8.55. Found: %C, 62.05; %H, 6.78; %N, 8.23.

Field Desorption Mass Spectrum: M=318.

EXAMPLE 115

N-2-(4-(4-pyridyl)phenyl)propyl 2-propanesulfonamide

To a solution of 1.0 g (3.1 mmol) of material from Preparation 39 and 1.1 g (3.1 mmol) of 4-(tri-n-butylstannyl)pyridine in 10 mL of dioxane was added 0.072 g (0.062 mmol) of tetrakis(triphenylphosphine)palladium(0). The mixture was heated at 90° C. for 18 h. Then 0.1 g (0.08 mmol) of tetrakis(triphenylphosphine)palladium(0) and 0.5 g (1.5 mmol) of 4-(tri-n-butylstannyl)pyridine was added and the mixture was heated at 90° C. for 18 h. The mixture was cooled and filtered through diatomaceous earth and rinsed with 10 mL ethyl acetate. The organic was dried ($MgSO_4$), filtered and concentrated in vacuo. The residue was suspended in 10 mL of dichloromethane and the solid was filtered and washed with 10 mL of hexane to afforded 0.24 g (24%) of the title compound.

Analysis calculated for $C_{17}H_{22}N_2O_2S$: %C, 64.12; %H, 6.96; %N, 8.80. Found: %C, 63.90; %H, 6.71; %N, 8.93.

Field Desorption Mass Spectrum: M=318.

EXAMPLE 116

N-2-(4-(3-pyridyl)phenyl)propyl 2-propanesulfonamide

To a solution of 1.0 g (3.1 mmol) of material from Preparation 39 and 1.1 g (3.1 mmol) of 3-(tri-n-butylstannyl)pyridine in 10 mL of toluene was added 0.072 g (0.062 mmol) of tetrakis(triphenylphosphine)palladium(0). The mixture was heated at 90° C. for 18 h. Then 0.1 g (0.08 mmol) of tetrakis(triphenylphosphine)palladium(0) and 0.5 g (1.5 mmol) of 3-(tri-n-butylstannyl)pyridine was added and the mixture was heated at 90° C. for 18 h. The mixture was cooled and filtered through diatomaceous earth and rinsed with 10 mL ethyl acetate. The filtrate was concentrated in vacuo. Chromatography (75 g of silica gel, 75% ethyl acetate/hexane) of the residue afforded 0.43 g (44%) of the title compound.

Analysis calculated for $C_{17}H_{22}N_2O_2S*0.25H_2O$: %C, 63.23; %H, 7.02; %N, 8.67. Found: %C, 63.31; %H, 7.04; %N, 8.01.

Field Desorption Mass Spectrum: M=318.

EXAMPLE 117

N-2-(4-(5-pyrimidinyl)phenyl)propyl 2-propanesulfonamide

A. 5-(tri-n-butylstannyl)pyrimidine: A solution of 19.6 mL (31.4 mmol) 1.6M n-butyllithium in 100 mL of ether was cooled to −100° C. and a solution of 5 g (31.4 mmol) of 5-bromopyrimidine in 20 mL of ether was added dropwise. The mixture was stirred at −78° C. for 30 min then 8.5 mL (31.4 mmol) of tri-n-butylstannyl chloride in 20 mL of ether was added dropwise. The mixture was stirred for 30 min and then 100 mL of water was added. The organic layer was separated and the aqueous layer was extracted three times with 30 mL each of ether. The combined organic extracts were dried (MgSO$_4$), filtered and concentrated in vacuo. Chromatography (250 g of silica gel, 50% ethyl acetate/hexane) of the residue afforded 3.3 g (28%) of the title compound.

B. To a solution of 1.4 g (4.4 mmol) of material from Preparation 39 and 3.3 g (8.9 mmol) of material from Example 117A in 15 mL of dioxane was added 0.25 g (0.2 mmol) of tetrakis(triphenylphosphine)palladium(0). The mixture was heated at 90° C. for 18 h. The mixture was cooled and concentrated in vacuo. The residue was suspended in 10 mL of acetonitrile and the solid was filtered and washed with 5 mL of acetonitrile to afforded 0.06 g (4%) of the title compound.

Analysis calculated for $C_{16}H_{21}N_3O_2S$: %C, 60.16; %H, 6.63; %N, 13.15. Found: %C, 60.18; %H, 6.62; %N, 13.00.

Field Desorption Mass Spectrum: M=319.

EXAMPLE 118

N-2-(4-(3-thienyl)phenyl)ethyl 2-propanesulfonamide

To a solution of 1.0 g (3.3 mmol) of material from Preparation 47, 0.5 g (3.9 mmol) of thiophene-3-boronic acid and 0.7 g (4.9 mmol) of potassium carbonate in 8 mL of dioxane and 2 mL of water was added 0.18 g (0.16 mmol) of tetrakis(triphenylphosphine)palladium(0). The mixture was heated at 90° C. for 18 h. The mixture was cooled to room temperature and 10 mL of water and 10 mL of ether was added. The organic layer was separated and the aqueous layer was extracted three times with 5 mL each of ether. The combined organic extracts were dried (MgSO$_4$), filtered and concentrated in vacuo. Chromatography (50 g of silica gel, 35% ethyl acetate/hexane) of the residue afforded 0.6 g (59%) of the title compound.

Analysis calculated for $C_{15}H_{19}NO_2S_2$: %C, 58.22; %H, 6.19; %N, 4.53. Found: %C, 58.30; %H, 5.96; %N, 4.48.

Field Desorption Mass Spectrum: M=309.

EXAMPLE 119

N-2-(4-(4-formylphenyl)phenyl)ethyl 2-propanesulfonamide

To a solution of 4.0 g (13.3 mmol) of material from Preparation 47, 2.3 g (15.7 mmol) of 4-formyl-benzene-boronic acid and 2.7 g (19.6 mmol) of potassium carbonate in 32 mL of dioxane and 8 mL of water was added 0.7 g (0.6 mmol) of tetrakis(triphenylphosphine)palladium(0). The mixture was heated at 90° C. for 5 h. The mixture was cooled to room temperature and 40 mL of water and 40 mL of ether was added. The organic layer was separated and the aqueous layer was extracted three times with 20 mL each of ether. The combined organic extracts were dried (MgSO$_4$), filtered and concentrated in vacuo. Chromatography (200 g of silica gel, 35% ethyl acetate/hexane) of the residue afforded 3.6 g (83%) of the title compound.

Analysis calculated for $C_{18}H_{21}NO_3S$: %C, 65.23; %H, 6.39; %N, 4.23. Found: %C, 65.38; %H, 6.43; %N, 4.05.

Field Desorption Mass Spectrum: M=331.

EXAMPLE 120

N-2-(4-(4-hydroxymethylphenyl)phenyl)ethyl 2-propanesulfonamide

To a solution of 0.5 g (1.5 mmol) of material from Example 119 in 20 mL of ethyl alcohol was added 0.056 g (1.5 mmol) of sodium borohydride. The mixture was stirred at ambient temperature for 2 hr and then 10 mL of ethyl acetate and 10 mL of water was added. The organic layer was separated and the aqueous layer was extracted two times with 5 mL each of ethyl acetate. The combined organic extracts were dried (MgSO$_4$), filtered and concentrated in vacuo to afford 0.5 g (100%) of the title compound.

Analysis calculated for $C_{18}H_{23}NO_3S$: %C, 64.84; %H, 6.95; %N, 4.20. Found: %C, 64.74; %H, 6.92; %N, 4.36.

Field Desorption Mass Spectrum: M=333.

EXAMPLE 121

N-2-(4-(4-N'-(2-propanesulfonylanilino))phenyl) ethyl 2-propanesulfonamide

A. 4-Bromo-N-(t-butoxycarbonyl)aniline: To a solution of 6.0 g (34.9 mmol) of 4-bromoaniline in 110 mL of tetrahydrofuran was added 70 mL (70 mmol) 1N sodium bis(trimethylsilyl)amide. The mixture was stirred for 15 min and 7.6 g (34.9 mmol) of di-tert-butyl dicarbonate was added. The mixture was stirred for 18 hr and then concentrated in vacuo. The residue was partitioned between 120 mL of 10% aqueous sodium bisulfate and 120 mL of ethyl acetate. The organic layer was separated and washed two times with 50 mL each of brine. The organic layer was dried (MgSO$_4$), filtered and concentrated in vacuo. Chromatography (250 g of silica gel, 10% ethyl acetate/hexane) of the residue afforded 5.4 g (57%) of the title compound.

B. N-2-(4-(4-N'-t-butoxycarbonylaminophenyl)phenyl)t-butoxycarbonyl)propylamine: To a solution of 1.75 g (3.4 mmol) of material from Preparation 48 and 1.0 g (3.4 mmol) of material from Example 121A in 10 mL of toluene was added 0.2 g (0.17 mmol) of tetrakis (triphenylphosphine)palladium(0). The mixture was heated at 100° C. for 18 h. The mixture was cooled and 10 mL of water was added. The organic layer was separated and the aqueous layer was extracted three times with 5 mL each of ethyl acetate. The combined organic extracts were dried (MgSO$_4$), filtered and concentrated in vacuo. Chromatography (100 g of silica gel, 35% ethyl acetate/hexane) of the residue afforded 0.2 g (14%) of the title compound.

C. A solution of 0.2 g (0.48 mmol) of material from Example 121B in 4 mL of dichloromethane and 1 mL of trifluoroacetic acid was stirred at ambient temperature for 3 h. The mixture was concentrated in vacuo and the residue was dissolved in 5 mL dichloromethane and 0.15 mL (1.0 mmol) of 1,8-diazabicyclo[5.4.0]undec-7-ene was added. The solution was cooled to 0° C. and a solution of 0.06 mL (0.5 mmol) of isopropylsulfonyl chloride in 1 mL of dichloromethane was added. The ice-bath was removed and the mixture was stirred at ambient temperature for 4 h. The mixture was washed with 5 mL of 1N aqueous hydrochloric acid, the organic layer was separated and the aqueous layer extracted three times with 5 mL of ethyl acetate. The combined organics were dried (MgSO$_4$), filtered and concentrated in vacuo. Chromatography (12 g of silica gel, 50% ethyl acetate/-hexane) of the residue afforded 0.005 g (2%) of the title compound.

Field Desorption Mass Spectrum: M=424.

EXAMPLE 122

N-2-(4-(4-cyanophenyl)phenyl)ethyl 2-propanesulfonamide

To a solution of 1.7 g (3.4 mmol) of material from Preparation 48 and 0.6 g (3.4 mmol) of 4-bromobenzonitrile in 10 mL of toluene was added 0.2 g (0.17 mmol) of tetrakis(triphenylphosphine)palladium(0). The mixture was heated at 100° C. for 18 h. The mixture was cooled and the solid was filtered and rinsed with 10 mL hexane to afforded 0.4 g (36%) of the title compound.

Analysis calculated for $C_{18}H_{20}N_2O_2S$: %C, 65.83; %H, 6.14; %N, 8.53. Found: %C, 65.61; %H, 5.87; %N, 8.44.

Field Desorption Mass Spectrum: M=328.

EXAMPLE 123

N-2-(4-(4-N',N'-diethylaminophenyl)phenyl)propyl 2-propanesulfonamide

A. 4-N,N-diethylaminobenzeneboronic acid: A solution of 10 g (43.8 mmol) of 4-bromo-N,N-diethylaniline in 150 mL of tetrahydrofuran was cooled to −78° C. and 30 mL (48.2 mmol) of 1.6M n-butyllithium was added dropwise. The mixture was stirred at −78° C. for 60 min then 15.2 mL (65.7 mmol) of triisopropyl borate was added dropwise and stirring was continued for 60 min. The cooling bath was removed and then 75 mL of water and 5N hydrochloric acid was added until pH=6 and stirring was continued for 18 h. The aqueous layer was separated and the organic layer was extracted two times with 25 mL each of 1N sodium hydroxide. The combined aqueous extracts were acidified with conc. hydrochloric acid to pH=7. The resulting solid was filtered and washed with 20 mL methyl alcohol to 2.8 g (33%) of the title compound.

B. To a solution of 0.5 g (1.6 mmol) of material from Preparation 39, 0.36 g (1.9 mmol) of material from Example 123A and 0.33 g (2.4 mmol) of potassium carbonate in 4 mL of dioxane and 1 mL of water was added 0.09 g (0.07 mmol) of tetrakis(triphenylphosphine)palladium(0). The mixture was heated at 90° C. for 18 h. The mixture was cooled to room temperature and 10 mL of water and 5 mL of ether was added. The organic layer was separated and the aqueous layer was extracted three times with 5 mL each of ether. The combined organic extracts were dried ($MgSO_4$), filtered and concentrated in vacuo. Chromatography (25 g of silica gel, 25% ethyl acetate/hexane) of the residue afforded 0.38 g (61%) of the title compound.

Analysis calculated for $C_{22}H_{32}N_2O_2S$: %C, 68.00; %H, 8.30; %N, 7.21. Found: %C, 67.70; %H, 8.52; %N, 6.98.

Field Desorption Mass Spectrum: M=388.

EXAMPLE 124

N-2-(4-(2-fluorophenyl)phenyl)propyl 1-chloromethanesulfonamide

A solution of 0.4 g (1.7 mmol) of material from Preparation 6 and 0.27 mL (1.9 mmol) of triethylamine in 10 mL of dichloromethane was cooled to 0° C. A solution of 0.15 mL (1.7 mmol) of methanesulfonyl chloride in 1 mL of dichloromethane was added. The ice-bath was removed and the mixture was stirred at room temperature for 3 h. The mixture was washed with 10 mL of 10% aqueous sodium bisulfate, the organic layer was separated and the aqueous layer extracted three times with 5 mL of 1:1 dichloromethane/ether. The combined organics were dried ($MgSO_4$), filtered and concentrated in vacuo to afford 0.60 g (100%) of the title compound.

Analysis calculated for $C_{16}H_{17}ClFNO_2S$: %C, 56.22; %H, 5.01; %N, 4.10. Found: %C, 56.55; %H, 5.27; %N, 4.10.

Field Desorption Mass Spectrum: M=341.

EXAMPLE 125

N-2-(4-(4-(1-(2-(2-propane)sulfonylamino)propyl)phenyl)phenyl)propyl 2-propanesulfonamide To a solution of 1.3 g (2.5 mmol) of material from Preparation 40 and 0.65 g (5.0 mmol) of 3-chloro-6-methyl pyridazine in 10 mL of toluene was added 0.14 g (0.12 mmol) of tetrakis(triphenylphosphine)palladium(0). The mixture was heated at 90° C. for 18 h. The mixture was cooled and filtered through diatomaceous earth and rinsed with 10 mL ethyl acetate. The filtrate was concentrated in vacuo. Chromatography (50 g of silica gel, 50% ethyl acetate/hexane) of the residue afforded 0.20 g (33%) of the title compound.

Analysis calculated for $C_{24}H_{36}N_2O_4S$: %C, 59.97; %H, 7.55; %N, 5.83. Found: %C, 59.67; %H, 7.55; %N, 5.97.

Field Desorption Mass Spectrum: M−1=479.

EXAMPLE 126

N-2-(4-(4-(1-(2-(2-propane)sulfonylamino)-ethyl)phenyl)phenyl)ethyl 2-propanesulfonamide To a solution of 1.5 g (4.9 mmol) of material from Preparation 47, 0.8 g (2.4 mmol) of hexamethyiditin, and 0.6 g (14.7 mmol) of lithium chloride in 20 mL of dioxane was added 0.1 g (0.1 mmol) of tetrakis(triphenylphosphine)palladium(0). The mixture was heated at 90° C. for 18 h. The mixture was cooled and filtered through diatomaceous earth and rinsed with 10 mL ethyl acetate. The filtrate was washed one time with 10 mL of water and dried ($MgSO_4$), filtered and concentrated in vacuo. Chromatography (75 g of silica gel, 50% ethyl acetate/hexane) of the residue afforded 0.054 g (2.5%) of the title compound.

Analysis calculated for $C_{22}H_{32}N_2O_4S_2$: %C, 58.38; %H, 7.13; %N, 6.19. Found: %C, 58.54; %H, 7.08; %N, 5.92.

Field Desorption Mass Spectrum: M=452.

EXAMPLE 127

N-2-(4-(4-(1-(2-cyano)ethenyl)phenyl)phenyl)ethyl 2-pronanesulfonamide

To a solution of 1.5 g (8.4 mmol) of diethyl cyanomethyl phosphonate in 15 mL tetrahydrofuran was added 8.4 mL (8.4 mmol) 1M sodium bis(trimethylsilyl)amide. The mixture was stirred at ambient temperature for 30 min and then a solution of material from Example 119 in 5 mL of tetrahydrofuran was added. The mixture was stirred for 1 hr and was washed with 20 mL of water. The organic layer was separated and the aqueous layer extracted three times with 5 mL of ethyl acetate. The combined organics were dried $MgSO_4$), filtered and concentrated in vacuo. The residue was suspended in 5 mL dichloromethane and the resulting solid was filtered to afford 1.2 g (56%) of the title compound. The filtrate was concentrated in vacuo. Chromatography (100 g of silica gel, 50% ethyl acetate/hexane) of the residue afforded an additional 0.5 g (23%) of the title compound.

Analysis calculated for $C_{20}H_{22}N_2O_2S$: %C, 67.77; %H, 6.26; %N, 7.90. Found: %C, 67.50; %H, 6.21; %N, 7.73.

Field Desorption Mass Spectrum: M=354.

EXAMPLE 128

N-2-(4-(4-(1-(3-amino)propyl)phenyl)phenyl)ethyl 2-propanesulfonamide hydrochloride A solution of 0.47 g (1.3 mmol) of material from Example 127 and 0.32 g 5% palladium on carbon in 75 mL ethyl alcohol and 3 mL 5N hydrochloric acid was hydrogenated in a Parr shaker at 60 psi hydrogen and 50° C. for 18 h. The mixture was filtered and concentrated in vacuo. The residue was suspended in 10 mL 1N hydrochloric acid and filtered. Recrystallization from acetonitrile and methyl alcohol afforded 0.1 g (20%) of the title compound.

Analysis calculated for $C_{20}H_{29}N_2O_2S*0.85HCl$: %C, 61.20; %H, 7.67; %N, 7.14. Found: %C, 61.06; %H, 7.70; %N, 6.91.

Field Desorption Mass Spectrum: M−1=360.

EXAMPLE 129

N-2-(4-(4-(1-(3-(2-propane)sulfonylamino)-propyl)phenyl)phenyl)ethyl 2-propanesulfonamide To a solution of 0.09 g (0.2 mmol) of material from Example 128 and 0.07 mL (0.5 mmol) of triethylamine in 5 mL of dichloromethane was added 0.025 mL (0.2 mmol) of isopropyl sulfonyl chloride. The mixture was stirred at room temperature for 8 h. The mixture was washed with 5 mL of 1N hydrochloric acid, the organic layer was separated and the aqueous layer extracted one time with 5 mL of ethyl acetate. The combined organics were dried ($MgSO_4$), filtered and concentrated in vacuo to afford 0.050 g (53%) of the title compound.

Analysis calculated for $C_{23}H_{34}N_2O_4S_2*0.5CHCl_3$: %C, 53.62; %H, 6.61; %N, 5.32. Found: %C, 53.18; %H, 6.78; %N, 4.97.

Field Desorption Mass Spectrum: M=466.

EXAMPLE 130

N-2-(4-(3-thienyl)phenyl)propyl ethenesulfonamide

To a solution of 0.21 g (0.9 mmol) of material from Preparation 53B and 0.15 mL (1.0 mmol) of 1,8-diazabicyclo[5.4.0]undec-7-ene in 5 mL of dichloromethane was added 0.10 mL (1.0 mmol) of 2-chloro-1-ethanesulfonyl chloride. The mixture was stirred at room temperature for 4 h. The mixture was washed with 5 mL of 1N hydrochloric acid, the organic layer was separated and the aqueous layer extracted three times with 5 mL of ether. The combined organics were dried ($MgSO_4$), filtered and concentrated in vacuo. Chromatography (10 g of silica gel, 25% ethyl acetate/hexane) of the residue afforded 0.2 g (71%) of the title compound.

Analysis calculated for $C_{15}H_{17}NO_2S_2*0.2CHCl_3$: %C, 55.10; %H, 5.23; %N, 4.22. Found: %C, 55.40; %H, 5.10; %N, 4.20.

Field Desorption Mass Spectrum: M−1=306.

EXAMPLE 131

N-2-(4-(3-thienyl)phenyl)propyl ethanesulfonamide

A solution of 0.024 g (0.078 mmol) of material from Example 130 and 5 mg 5% palladium on carbon in 5 mL ethyl acetate was degassed three times under a hydrogen balloon and stirred at room temperature for 4 h. The mixture was filtered and concentrated in vacuo. The residue was recrystallized from ether and hexane to afford 0.024 g (99%) of the title compound.

Analysis calculated for $C_{15}H_{19}NO_2S_2$: %C, 58.22; %H, 6.19; %N, 4.53. Found: %C, 58.63; %H, 5.71; %N, 4.32

Field Desorption Mass Spectrum: M+1=310.

EXAMPLE 132

N-2-(4-(3-acetylphenyl)phenyl)propyl 2-propanesulfonamide

To a solution of 3.2 g (10.2 mmol) of material from Preparation 39, 2.0 g (12.2 mmol) of 3-acetylbenzeneboronic acid and 2.1 g (15.2 mmol) of potassium carbonate in 28 mL of dioxane and 7 mL of water was added 0.59 g (0.51 mmol) of tetrakis(triphenylphosphine)palladium(0). The mixture was heated at 90° C. for 18 h. The mixture was cooled to room temperature and 30 mL of water and 30 mL of ether was added. The organic layer was separated and the aqueous layer was extracted three times with 10 mL each of ether. The combined organic extracts were dried ($MgSO_4$), filtered and concentrated in vacuo. Chromatography (150 g of silica gel, 35% ethyl acetate/hexane) of the residue afforded 2.4 g (66%) of the title compound.

Analysis calculated for $C_{20}H_{25}NO_3S$: %C, 66.82; %H, 7.01; %N, 3.89. Found: %C, 66.38; %H, 6.96; %N, 3.73.

Field Desorption Mass Spectrum: M=359.

EXAMPLE 133

N-2-(4-(3-(1-hydroxyethyl)phenyl)phenyl)propyl 2-propanesulfonamide

To a solution of 0.5 g (1.4 mmol) of material from Example 132 in 5 mL of ethyl alcohol was added 0.05 g (1.4 mmol) of sodium borohydride. The mixture was stirred at ambient temperature for 2 hr, concentrated in vacuo and then 10 mL of ethyl acetate and 10 mL of water was added. The organic layer was separated and the aqueous layer was extracted three times with 5 mL each of ethyl acetate. The combined organic extracts were dried ($MgSO_4$), filtered and concentrated in vacuo. Chromatography (40 g of silica gel, 50% ethyl acetate/hexane) of the residue afforded 0.3 g (65%) of the title compound.

Analysis calculated for $C_{20}H_{27}NO_3S$: %C, 66.40; %H, 7.53; %N, 3.87. Found: %C, 66.56; %H, 7.65; %N, 3.92.

Field Desorption Mass Spectrum: M=361.

EXAMPLE 134

N-2-(4-(2-benzothienyl)phenyl)propyl 2-propanesulfonamide

To a solution of 0.5 g (1.5 mmol) of material from Preparation 39, 0.3 g (1.9 mmol) of benzo[b]thiophene-2-boronic acid and 0.3 g (2.3 mmol) of potassium carbonate in 4 mL of dioxane and 1 mL of water was added 0.09 g (0.08 mmol) of tetrakis(triphenylphosphine)palladium(0). The mixture was heated at 90° C. for 18 h. The mixture was cooled to room temperature and 5 mL of water and 5 mL of ether and 10 mL ethyl acetate was added. The mixture was concentrated in vacuo and the residue was dissolved in 10 mL of ethyl acetate and washed with 10 mL of brine. The organic layer was separated and dried ($MgSO_4$), filtered and concentrated in vacuo. Chromatography (50 g of silica gel, 35% ethyl acetate/hexane) of the residue afforded 0.08 g (14%) of the title compound.

Analysis calculated for $C_{20}H_{23}NO_2S_2*0.1\ CHCl_3$: %C, 62.40; %H, 6.07; %N, 3.63. Found: %C, 62.63; %H, 6.04; %N, 3.63.

Field Desorption Mass Spectrum: M=373.

EXAMPLE 135

N-2-(4-(3,4-dichlorophenyl)phenyl)propyl 2-propanesulfonamide

To a solution of 0.5 g (1.6 mmol) of material from Preparation 39, 0.4 g (1.9 mmol) of 3,4-dichlorobenzeneboronic acid and 0.3 g (2.3 mmol) of potassium carbonate in 5 mL of dioxane and 1 mL of water was added 0.09 g (0.08 mmol) of tetrakis(triphenylphosphine) palladium(0). The mixture was heated at 90° C. for 18 h. The mixture was cooled to room temperature and 5 mL of water and 5 mL of ether was added. The organic layer was separated and the aqueous layer was extracted three times with 5 mL each of ethyl acetate. The combined organic extracts were dried ($MgSO_4$), filtered and concentrated in vacuo. Chromatography (75 g of silica gel, 35% ethyl acetate/hexane) of the residue afforded 0.52 g (86%) of the title compound. A second chromatography (40 g of silica gel, 35% ethyl acetate/hexane) of the title compound afforded 0.25 g (41%) of the title compound.

Analysis calculated for $C_{18}H_{21}Cl_2NO_2S$: %C, 55.95; %H, 5.48; %N, 3.62. Found: %C, 56.22; %H, 5.28; %N, 3.56.

Field Desorption Mass Spectrum: M−1=385.

EXAMPLE 136

N-2-(4-(4-methylphenyl)phenyl)propyl 2-propanesulfonamide

To a solution of 0.5 g (1.6 mmol) of material from Preparation 39, 0.25 g (1.9 mmol) of 4-methylbenzeneboronic acid and 0.3 g (2.3 mmol) of potassium carbonate in 5 mL of dioxane and 1 mL of water was added 0.09 g (0.08 mmol) of tetrakis (triphenylphosphine)palladium(0). The mixture was heated at 90° C. for 18 h. The mixture was cooled to room temperature and 5 mL of water and 5 mL of ether was added. The organic layer was separated and the aqueous layer was extracted three times with 5 mL each of ethyl acetate. The combined organic extracts were dried ($MgSO_4$), filtered and concentrated in vacuo. Chromatography (30 g of silica gel, 35% ethyl acetate/hexane) of the residue afforded 0.42 g (82%) of the title compound. A second chromatography (25 g of silica gel, 35% ethyl acetate/hexane) of the title compound afforded 0.24 g (46%) of the title compound.

Analysis calculated for $C_{19}H_{25}NO_2S$: %C, 68.80; %H, 7.60; %N, 4.20. Found: %C, 69.11; %H, 7.70; %N, 4.10.

Field Desorption Mass Spectrum: M=331.

EXAMPLE 137

N-2-(4-(4-chlorophenyl)phenyl)propyl 2-propanesulfonamide

To a solution of 0.5 g (1.6 mmol) of material from Preparation 39, 0.29 g (1.9 mmol) of 4-chlorobenzeneboronic acid and 0.3 g (2.3 mmol) of potassium carbonate in 5 mL of dioxane and 1 mL of water was added 0.09 g (0.08 mmol) of tetrakis(triphenylphosphine) palladium(0). The mixture was heated at 90° C. for 18 h. The mixture was cooled to room temperature and 5 mL of water and 5 mL of ether was added. The organic layer was separated and the aqueous layer was extracted three times with 3 mL each of ethyl acetate. The combined organic extracts were dried ($MgSO_4$), filtered and concentrated in vacuo. Chromatography (35 g of silica gel, 35% ethyl acetate/hexane) of the residue afforded 0.36 g of the title compound. The compound was recrystallized to purity with ether to afford 0.36 g (65%) of the title compound.

Analysis calculated for $C_{18}H_{22}ClNO_2S$: %C, 61.40; %H, 6.30; %N, 3.98. Found: %C, 61.48; %H, 6.11; %N, 3.62.

Field Desorption Mass Spectrum: M=351.

EXAMPLE 138

N-2-(4-(2-methylphenyl)phenyl)propyl 2-propanesulfonamide

To a solution of 0.5 g (1.6 mmol) of material from Preparation 39, 0.25 g (1.9 mmol) of 2-methylbenzeneboronic acid and 0.3 g (2.3 mmol) of potassium carbonate in 5 mL of dioxane and 1 mL of water was added 0.09 g (0.08 mmol) of tetrakis (triphenylphosphine)palladium(0). The mixture was heated at 90° C. for 18 h. The mixture was cooled to room temperature and 5 mL of water and 5 mL of ether was added. The organic layer was separated and the aqueous layer was extracted three times with 4 mL each of ethyl acetate. The combined organic extracts were dried ($MgSO_4$), filtered and concentrated in vacuo. Chromatography (30 g of silica gel, 30% ethyl acetate/hexane) of the residue afforded 0.35 g (68%) of the title compound.

Analysis calculated for $C_{19}H_{25}NO_2S$: %C, 68.8; %H, 7.60; %N, 4.20. Found: %C, 68.82; %H, 7.75; %N, 4.23.

Field Desorption Mass Spectrum: M=331.

EXAMPLE 139

N-2-(4-(3,5-dichlorophenyl)phenyl)propyl 2-propanesulfonamide

To a solution of 0.5 g (1.6 mmol) of material from Preparation 39, 0.36 g (1.9 mmol) of 3,5-dichlorobenzeneboronic acid and 0.3 g (2.3 mmol) of potassium carbonate in 5 mL of dioxane and 1 mL of water was added 0.09 g (0.08 mmol) of tetrakis(triphenylphosphine) palladium(0). The mixture was heated at 90° C. for 18 hr and then 0.36 g (1.9 mmol) of 3,5-dichlorobenzeneboronic acid was added. The mixture was heated at 90° C. for another 18 h. The mixture was cooled to room temperature and 10 mL of water and 10 mL of ether was added. The organic layer was separated and the aqueous layer was extracted three times with 5 mL each of ethyl acetate. The combined organic extracts were dried ($MgSO_4$), filtered and concentrated in vacuo. Chromatography (35 g of silica gel, 10% ethyl acetate/toluene) of the residue afforded 0.36 g (60%) of the title compound.

Analysis calculated for $C_{18}H_{21}NCl_2O_2S$: %C, 55.90; %H, 5.50; %N, 3.60. Found: %C, 56.22; %H, 5.50; %N, 3.39.

Field Desorption Mass Spectrum: M−1=385.

EXAMPLE 140

N-2-(4-(4-trifluoromethylphenyl)phenyl)propyl 2-propanesulfonamide

To a solution of 0.5 g (1.6 mmol) of material from Preparation 39, 0.35 g (1.9 mmol) of 4-trifluoromethylbenzeneboronic acid and 0.3 g (2.3 mmol) of potassium carbonate in 5 mL of dioxane and 1 mL of water was added 0.09 g (0.08 mmol) of tetrakis (triphenylphosphine)palladium(0). The mixture was heated at 90° C. for 18 h. The mixture was cooled to room temperature and 5 mL of water and 5 mL of ether was added. The organic layer was separated and the aqueous layer was extracted three times with 4 mL each of ethyl acetate. The combined organic extracts were dried ($MgSO_4$), filtered and concentrated in vacuo. Chromatography (50 g of silica gel, 20% ethyl acetate/hexane) of the residue afforded 0.40 g (67%) of the title compound.

Analysis calculated for $C_{19}H_{22}F_3NO_2S$: %C, 59.20; %H, 5.75; %N, 3.60. Found: %C, 59.14; %H, 5.67; %N, 3.34.

Field Desorption Mass Spectrum: M=385.

EXAMPLE 141

N-2-(4-(3-trifluoromethylphenyl)phenyl)propyl 2-propanesulfonamide

To a solution of 0.5 g (1.6 mmol) of material from Preparation 39, 0.35 g (1.9 mmol) of 3-trifluoromethylbenzeneboronic acid and 0.3 g (2.3 mmol) of potassium carbonate in 5 mL of dioxane and 1 mL of water was added 0.09 g (0.08 mmol) of tetrakis (triphenylphosphine)palladium(0). The mixture was heated at 90° C. for 18 h. The mixture was cooled to room temperature and 5 mL of water and 5 mL of ether was added. The organic layer was separated and the aqueous layer was extracted three times with 4 mL each of ethyl acetate. The combined organic extracts were dried (MgSO$_4$), filtered and concentrated in vacuo. Chromatography (50 g of silica gel, 20% ethyl acetate/hexane) of the residue afforded 0.44 g (73%) of the title compound.

Analysis calculated for $C_{19}H_{22}F_3NO_2S$: %C, 59.20; %H, 5.75; %N, 3.60. Found: %C, 59.20; %H, 5.72; %N, 3.62.

Field Desorption Mass Spectrum: M =385.

EXAMPLE 142

N-2-(4-(3-nitrophenyl)phenyl)propyl 2-propanesulfonamide

To a solution of 0.5 g (1.6 mmol) of material from Preparation 39, 0.31 g (1.9 mmol) of 3-nitrobenzene-boronic acid and 0.3 g (2.3 mmol) of potassium carbonate in 5 mL of dioxane and 1 mL of water was added 0.09 g (0.08 mmol) of tetrakis(triphenylphosphine)palladium(0). The mixture was heated at 90° C. for 18 h. The mixture was cooled to room temperature and 5 mL of water and 5 mL of ether was added. The organic layer was separated and the aqueous layer was extracted three times with 4 mL each of ethyl acetate. The combined organic extracts were dried (MgSO$_4$), filtered and concentrated in vacuo. Chromatography (50 g of silica gel, 35% ethyl acetate/hexane) of the residue afforded 0.40 g (71%) of the title compound.

Analysis calculated for $C_{18}H_{22}N_2O_4S$: %C, 59.60; %H, 6.12; %N, 7.73. Found: %C, 59.59; %H, 6.07; %N, 7.74.

Field Desorption Mass Spectrum: M=362.

EXAMPLE 143

N-2-(4-(3-thienyl)phenyl)propyl 1-(2-methyl)-propanesulfonamide

A. Isobutylsulfonyl chloride: A solution of diisobutyldisulfide 13 g (73 mmol) in 100 mL of water is cooled to 0° C. Chlorine gas was bubbled through the aqueous solution until a yellow solution persists and then nitrogen gas was bubbled through for 15 min. The reaction mixture was diluted with 100 mL of ether and the organic layer was separated and the aqueous layer extracted three times with 30 mL of ether. The combined organics were dried (MgSO$_4$), filtered and concentrated in vacuo. The residue was distilled to afford 12 g (52%) of the title compound.

B. To a solution of 0.5 g (2.3 mmol) of material from Preparation 53B and 0.42 mL (3.0 mmol) of triethyl amine in 10 mL of tetrahydrofuran was added 0.47 g (3.0 mmol) of material from Example 143A. The mixture was stirred at room temperature for 18 h. The mixture was washed with 20 mL of 1N hydrochloric acid, the organic layer was separated and the aqueous layer extracted three times with 5 mL of ether. The combined organics were dried (MgSO$_4$), filtered and concentrated in vacuo. Chromatography (25 g of silica gel, 30% ethyl acetate/hexane) of the residue afforded 0.6 g (77%) of the title compound.

Analysis calculated for $C_{17}H_{23}NO_2S_2$: %C, 60.50; %H, 6.87; %N, 4.15. Found: %C, 60.30; %H, 6.88; %N, 4.07.

Field Desorption Mass Spectrum: M=337.

EXAMPLE 144

N-2-(4-(2-benzothiazoly)phenyl)propyl 2-propanesulfonamide

To a solution of 0.4 g (0.7 mmol) of material from Preparation 40 and 0.13 g (0.7 mmol) of 2-chlorobenzothiazole in 5 mL of xylene was added 0.016 g (0.02 mmol) of dichlorobis(triphenylphosphine)palladium (II). The mixture was heated at 120° C. for 18 hr and to the mixture was added 0.010 g (0.02 mmol) of dichlorobis (triphenylphosphine)palladium (II) and the mixture was heated at 120° C. for 5 h. The mixture was cooled and 20 mL of saturated potassium fluoride was added and the mixture was stirred for 1 h. The mixture was filtered and the organic layer was removed, dried (MgSO$_4$), filtered and concentrated in vacuo. Chromatography (25 g of silica gel, 25% ethyl acetate/hexane) of the residue afforded 0.03 g (11%) of the title compound.

Analysis calculated for $C_{19}H_{22}N_2O_2S_2$: %C, 60.93; %H, 5.92; %N, 7.48. Found: %C, 61.24; %H, 6.05; %N, 7.04.

Field Desorption Mass Spectrum: M=374.

EXAMPLE 145

N-2-(4-(2-fluorophenyl)phenyl)propyl 2-methoxyethanesulfonamide

A solution of 0.5 g (1.6 mmol) of material from Example 8 in 5 mL of 2M ammonia in methyl alcohol was stirred at room temperature for 18 h. To the solution was added 2 mL of concentrated ammonium hydroxide and stirring was continued for 5 h. The mixture was concentrated in vacuo. Chromatography (25 g of silica gel, 50% ethyl acetate/hexane with 2% methyl alcohol) of the residue afforded 0.03 g (5%) of the title compound.

Analysis calculated for $C_{18}H_{22}FNO_3S$: %C, 61.52; %H, 6.31; %N, 3.99. Found: %C, 65.02; %H, 6.17; %N, 4.06.

Field Desorption Mass Spectrum: M=351.

EXAMPLE 146

N-2-(4-(2-fluorophenyl)phenyl)ethyl trifluoromethanesulfonamide

A solution of 1.0 g (3.0 mmol) of material from Example 7C and 1.0 mL (7.6 mmol) of triethyl amine in 10 mL of dichloromethane was cooled to 0° C. and 0.32 mL (3.0 mmol) of trifluoromethanesulfonyl chloride was added. The mixture was stirred at 0° C. for 1 h. The mixture was washed with 10 mL of 10% sodium bisulfate, the organic layer was separated and the aqueous layer extracted three times with 10 mL of dichloromethane. The combined organics were dried (MgSO$_4$), filtered and concentrated in vacuo to afford 0.45 g (43%) of the title compound.

Analysis calculated for $C_{15}H_{13}F_4NO_2$: %C, 51.87; %H, 3.77; %N, 4.03. Found: %C, 53.45; %H, 3.91; %N, 4.15.

Field Desorption Mass Spectrum: M=347.

EXAMPLE 147

N-2-(4-(2-fluorophenyl)phenyl)propyl trifluoromethanesulfonamide

A stock solution of 0.53 g (2.3 mmol) of material from Preparation 6 in 26 mL of chloroform was prepared and 1 mL was removed and added to a 4 mL teflon capped vial. To the vial was added 0.038 g (0.13 mmol) of poly(4-vinylpipridine) 2% crosslinked resin and 11.5 mL (0.11 mmol) trifluoromethanesulfonyl chloride. The vial was shaken at room temperature for 24 hr and then 0.040 g (0.8 mmol) of aminomethylpoly-styrene was added and the vial was shaken for 8 h. The reaction mixture was filtered through a cotton plug and the filtrate was concentrated in vacuo to afford the title compound. NMR was consistent with the proposed compound.

$^1$H NMR 300 MH$_2$ (CDCl$_3$) 67 =1.3(d)

EXAMPLE 148

N-2-(4-(2-fluorophenyl)phenyl)propyl trifluoroethanesulfonamide

The title compound was prepared following the method of Example 147 and using 12.2 mL (0.11 mmol) 2,2,2-trifluoroethanesulfonyl chloride. NMR was consistent with the proposed compound.

$^1$H NMR (CDCl$_3$) δ=3.9(m)

EXAMPLE 149

N-2-(4-(2-fluorophenyl)phenyl)propyl benzenesulfonamide

The title compound was prepared following the method of Example 147 and using 14.0 mL (0.11 mmol) benzenesulfonyl chloride. NMR was consistent with the proposed compound.

Electrospray Mass Spectrum: M+1=370.

EXAMPLE 150

N-2-(4-(2-fluorophenyl)phenyl)propyl 4-fluorobenzenesulfonamide

The title compound was prepared following the method of Example 147 and using 21 mg (0.11 mmol) 4-fluorobenzenesulfonyl chloride. NMR was consistent with the proposed compound.

$^1$H NMR (CDCl$_3$) δ=4.3(m)

EXAMPLE 151

N-2-(4-(4-(2-(ethanesulfonylamino)ethyl)-phenyl) phenyl)propyl 2-propanesulfonamide The title compound was prepared following the method of Example 147 and using 1 mL of a stock solution of 0.5 g (1.4 mmol) of material from Example 50 and 7.6 mL (0.11 mmol) ethanesulfonyl chloride. NMR was consistent with the proposed compound.

Electrospray Mass Spectrum: M−1=451.

EXAMPLE 152

N-2-(4-(4-(2-(1-propanesulfonylamino)ethyl)-phenyl)phenyl)propyl 2-propanesulfonamide The title compound was prepared following the method of Example 147 and using 1 mL of a stock solution of 0.5 g (1.4 mmol) of material from Example 50 and 9.0 mL (0.11 mmol) 1-propanesulfonyl chloride. NMR was consistent with the proposed compound.

Electrospray Mass Spectrum: M−1=465.

EXAMPLE 153

N-2-(4-(4-(2-(1-butanesulfonylamino)ethyl)-phenyl)phenyl)propyl 2-propanesulfonamide The title compound was prepared following the method of Example 147 and using 1 mL of a stock solution of 0.5 g (1.4 mmol) of material from Example 50 and 10.4 mL (0.11 mmol) 1-butanesulfonyl chloride. NMR was consistent with the proposed compound.

Electrospray Mass Spectrum: M−1=479.

EXAMPLE 154

N-2-(4-(1-(2-(1S-10-camphorsulfonylamino)-ethyl) phenyl)phenyl)propyl 2-propanesulfonamide The title compound was prepared following the method of Example 147 and using 1 mL of a stock solution of 0.5 g (1.4 mmol) of material from Example 50 and 20 mg(0.11 mmol) 1S-10-camphorsulfonyl chloride. NMR was consistent with the proposed compound.

Electrospray Mass Spectrum: M−1=573.

EXAMPLE 155

N-2-(4-(1-(2-(1R-10-camphorsulfonylamino)-ethyl) phenyl)phenyl)propyl 2-propanesulfonamide The title compound was prepared following the method of Example 147 and using 1 mL of a stock solution of 0.5 g (1.4 mmol) of material from Example 50 and 20 mg (0.11 mmol) 1R-10-camphorsulfonyl chloride. NMR was consistent with the proposed compound.

Electrospray Mass Spectrum: M−1=573.

EXAMPLE 156

N-2-(4-(1-(2-(2-methoxycarbonylethane-sulfonylamino)ethyl)phenyl)phenyl)propyl 2-propanesulfonamide The title compound was prepared following the method of Example 147 and using 1 mL of a stock solution of 0.5 g (1.4 mmol) of material from Example 50 and 15 mg (0.11 mmol) 2-carbomethoxyethane-sulfonyl chloride. NMR was consistent with the proposed compound.

Electrospray Mass Spectrum: [M+H$_2$O]=528.

EXAMPLE 157

N-2-(4-(1-(2-(2-trifluoroethane-sulfonylamino)ethyl) phenyl)phenyl)propyl 2-propanesulfonamide The title compound was prepared following the method of Example 147 and using 1 mL of a stock solution of 0.5 g (1.4 mmol) of material from Example 50 and 8.8 mL (0.11 mmol) 2,2,2-trifluoro-ethanesulfonyl chloride. NMR was consistent with the proposed compound.

Electrospray Mass Spectrum: M−1=505.

EXAMPLE 158

N-2-(4-(1-(2-(benzenesulfonylamino)-ethyl)phenyl) phenyl)propyl 2-propanesulfonamide The title compound was prepared following the method of Example 147 and using 1 mL of a stock solution of 0.5 g (1.4 mmol) of material from Example 50 and 14 mg (0.11 mmol) benzenesulfonyl chloride. NMR was consistent with the proposed compound.

Electrospray Mass Spectrum: M−1=499.

EXAMPLE 159

N-2-(4-(1-(2-(benzylsulfonylamino)-ethyl)phenyl) phenyl)propyl 2-propanesulfonamide The title compound was prepared following the method of Example 147 and using 1 mL of a stock solution of 0.5 g (1.4 mmol) of material from Example 50 and 15 mg (0.11 mmol) a-toluenesulfonyl chloride. NMR was consistent with the proposed compound.

Electrospray Mass Spectrum: M−1=513.

EXAMPLE 160

N-2-(4-(1-(2-(cyclohexanesulfonylamino)-ethyl) phenyl)phenyl)propyl 2-propanesulfonamide The title compound was prepared following the method of Example 147 and using 1 mL of a stock solution of 0.5 g (1.4 mmol) of material from Example 50 and 15 mg (0.11 mmol) cyclohexanesulfonyl chloride. NMR was consistent with the proposed compound.

Electrospray Mass Spectrum: M−1=505.

EXAMPLE 161

N-2-(4-(4-(2-(2-fluorobenzenesulfonylamino)-ethyl) phenyl)phenyl)propyl 2-propanesulfonamide The title compound was prepared following the method of Example 147 and using 1 mL of a stock solution of 0.5 g (1.4 mmol) of material from Example 50 and 15 mg (0.11 mmol) 2-fluorobenzenesulfonyl chloride. NMR was consistent with the proposed compound.

Electrospray Mass Spectrum: M−1=517.

EXAMPLE 162

N-2-(4-(4-(2-(3-trifluoromethylbenzene-sulfonylamino)ethyl)phenyl)phenyl)propyl 2-propanesulfonamide The title compound was prepared following the method of Example 147 and using 1 mL of a stock solution of 0.5 g (1.4 mmol) of material from Example 50 and 19 mg (0.11 mmol) 3-trifluoromethyl-benzenesulfonyl chloride. NMR was consistent with the proposed compound.

Electrospray Mass Spectrum: M−1=567.

EXAMPLE 163

N-2-(4-(4-(2-(4-fluorobenzenesulfonylamine)-ethyl) phenyl)phenyl)propyl 2-propanesulfonamide The title compound was prepared following the method of Example 147 and using 1 mL of a stock solution of 0.5 g (1.4 mmol) of material from Example 50 and 15 mg (0.11 mmol) 4-fluorobenzenesulfonyl chloride. NMR was consistent with the proposed compound.

Electrospray Mass Spectrum: M−1=517.

EXAMPLE 164

N-2-(4-(4-(2-(2-thiophenesulfonylamino)-ethyl) phenyl)phenyl)propyl 2-propanesulfonamide The title compound was prepared following the method of Example 147 and using 1 mL of a stock solution of 0.5 g (1.4 mmol) of material from Example 50 and 14 mg (0.11 mmol) 2-thiophenesulfonyl chloride. NMR was consistent with the proposed compound.

Electrospray Mass Spectrum: M−1=505.

EXAMPLE 165

N-2-(4-(4-(2-(4-methoxybenzenesulfonylamine)-ethyl)phenyl)phenyl)propyl 2-propanesulfonamide The title compound was prepared following the method of Example 147 and using 1 mL of a stock solution of 0.5 g (1.4 mmol) of material from Example 50 and 16 mg (0.11 mmol) 4-methoxybenzenesulfonyl chloride. NMR was consistent with the proposed compound.

Electrospray Mass Spectrum: M−1=529.

EXAMPLE 166

N-2-(4-(4-(2-(4-trifluoromethylbenzenesulfonylamine)ethyl)phenyl) phenyl)-propyl 2-propanesulfonamide The title compound was prepared following the method of Example 147 and using 1 mL of a stock solution of 0.5 g (1.4 mmol) of material from Example 50 and 20 mg (0.11 mmol) 4-trifluoromethylbenzenesulfonyl chloride. NMR was consistent with the proposed compound.

Electrospray Mass Spectrum: M−1=567.

EXAMPLE 167

N-2-(4-(4-(2-(1-(5-dimethylamino)naphthalene-sulfonylamino)ethyl)phenyl)phenyl)propyl 2-propanesulfonamide The title compound was prepared following the method of Example 147 and using 1 mL of a stock solution of 0.5 g (1.4 mmol) of material from Example 50 and 22 mg (0.11 mmol) dansyl chloride. NMR was consistent with the proposed compound.

Electrospray Mass Spectrum: M+1=594.

EXAMPLE 168

N-2-(4-(4-(2-(benzamido)ethyl)phenyl)phenyl) propyl 2-propanesulfonamide

The title compound was prepared following the method of Example 147 and using 1 mL of a stock solution of 0.6 g (1.8 mmol) of material from Example 50 and 15 mL (0.11 mmol) benzoyl chloride. NMR was consistent with the proposed compound.

Electrospray Mass Spectrum: M+1=465.

EXAMPLE 169

N-2-(4-(1-(2-(3-methylbutaneamido)-ethyl)phenyl) phenyl)propyl 2-propanesulfonamide The title compound was prepared following the method of Example 147 and using 1 mL of a stock solution of 0.6 g (1.8 mmol) of material from Example 50 and 13 mL (0.11 mmol) valeryl chloride. NMR was consistent with the proposed compound.

Electrospray Mass Spectrum: M+1=445.

EXAMPLE 170

N-2-(4-(4-(2-(4-fluorobenzamido)ethyl)phenyl)-phenyl)propyl 2-propanesulfonamide The title compound was prepared following the method of Example 147 and using 1 mL of a stock solution of 0.6 g (1.8 mmol) of material from Example 50 and 13 mL (0.11 mmol) 4-fluorobenzoyl chloride. NMR was consistent with the proposed compound.

Electrospray Mass Spectrum: M+1=483.

EXAMPLE 171

N-2-(4-(4-(2-(3-methoxybenzamido)-ethyl)phenyl) phenyl)propyl 2-propanesulfonamide The title compound was prepared following the method of Example 147 and using 1 mL of a stock solution of 0.6 g (1.8 mmol) of material from Example 50 and 18 mg (0.11 mmol) 3-methoxybenzoyl chloride. NMR was consistent with the proposed compound.

Electrospray Mass Spectrum: M+1=495.

EXAMPLE 172

N-2-(4-(4-(2-(2-thiopheneamido)ethyl)phenyl) phenyl)propyl 2-propanesulfonamide

The title compound was prepared following the method of Example 147 and using 1 mL of a stock solution of 0.6 g (1.8 mmol) of material from Example 50 and 11 mL (0.11 mmol) 2-thiophenecarbonyl chloride. NMR was consistent with the proposed compound.

Electrospray Mass Spectrum: M+1=471.

EXAMPLE 173

N-2-(4-(4-(2-(3-fluorobenzamido)ethyl)-phenyl) phenyl)propyl 2-propanesulfonamide The title compound was prepared following the method of Example 147 and using 1 mL of a stock solution of 0.6 g (1.8 mmol) of material from Example 50 and 13 mL (0.11 mmol) 3-fluorobenzoyl chloride. NMR was consistent with the proposed compound.

Electrospray Mass Spectrum: M+1=483.

EXAMPLE 174

N-2-(4-(4-(2-(4-methoxybenzamido)-ethyl)phenyl) phenyl)propyl 2-propanesulfonamide The title compound was prepared following the method of Example 147 and using 1 mL of a stock solution of 0.6 g (1.8 mmol) of material from Example 50 and 13 mL (0.11 mmol) 4-methoxybenzoyl chloride. NMR was consistent with the proposed compound.

Electrospray Mass Spectrum: M+1=495.

EXAMPLE 175

N-2-(4-(4-(2-(2-methylpropaneamido)-ethyl)phenyl) phenyl propyl 2-propanesulfonamide The title compound was prepared following the method of Example 147 and using 1 mL of a stock solution of 0.6 g (1.8 mmol) of material from Example 50 and 11 mL (0.11 mmol) isobutyryl chloride. NMR was consistent with the proposed compound.

Electrospray Mass Spectrum: M+1=431.

EXAMPLE 176

N-2-(4-(4-(2-(2-methoxybenzamido)-ethyl)phenyl) phenyl)propyl 2-propanesulfonamide The title compound was prepared following the method of Example 147 and using 1 mL of a stock solution of 0.6 g (1.8 mmol) of material from Example 50 and 16 mL (0.11 mmol) 2-methoxybenzoyl chloride. NMR was consistent with the proposed compound.

Electrospray Mass Spectrum: M+1=495.

EXAMPLE 177

N-2-(4-(4-(2-(phenylacetamido)ethyl)phenyl)phenyl) propyl 2-propanesulfonamide

The title compound was prepared following the method of Example 147 and using 1 mL of a stock solution of 0.6 g (1.8 mmol) of material from Example 50 and 14 mL (0.11 mmol) phenylacetyl chloride. NMR was consistent with the proposed compound.

Electrospray Mass Spectrum: M+1=479.

EXAMPLE 178

N-2-(4-(4-(2-(acetamido)ethyl)phenyl)phenyl)propyl 2-propanesulfonamide

The title compound was prepared following the method of Example 147 and using 1 mL of a stock solution of 0.6 g (1.8 mmol) of material from Example 50 and 8 mL (0.11 mmol) acetyl chloride. NMR was consistent with the proposed compound.

Electrospray Mass Spectrum: M−1=401.

EXAMPLE 179

N-2-(4-N-(benzamido)phenyl)propyl 2-propanesulfonamide

A solution of the material from Preparation 60 (333 mg, 0.93 mmol) in dichloromethane (5 ml) was treated with benzoyl chloride (197 mg, 1.4 mmol) and triethylamine (140 mg, 1.4 mmol). The reaction mixture was stirred at room temperature for 3 h. Water (10 ml) was added to the mixture and organic was extracted with ether (3×10 ml). The combined organic fraction was washed with brine (10 ml), dried over sodium sulfate, and concentrated in vacuo to give the crude product which was further purified by flash chromatography ($SiO_2$, 30% EtOAc: Hexanes). The pure product was treated with trifluoroacetic acid: dichloromethane (5 ml, 1:1 mixture). The mixture was stirred at room temperature for 1 h. Water (10 ml) was added to the mixture and the organic faction was extracted with dichloromethane (3×10 ml). The combined organic fraction was washed with water (2×10 ml), brine (10 ml), dried over sodium sulfate, and concentrated in vacuo to give 248 mg (74%) of the title compound. NMR was consistent with the proposed title structure. Field Desorption Mass Spectrum: $M^+$=360.

Analysis for $C_{19}H_{24}N_2O_3S$: Theory: C, 63.31; H, 6.71; N, 7.77. Found: C, 63.17; H, 6.67; N, 7.73.

EXAMPLE 180

N-2-(4-N-(acetamido)phenyl)propyl 2-propanesulfonamide

The title compound 118 mg (75%) was prepared as a solid following the method of Example 179, starting from the product of Preparation 60 and using acetyl chloride. NMR was consistent with the proposed title structure. Field Desorption Mass Spectrum: $M^+$=360.

Analysis for $C_{14}H_{22}N_2O_3S$: Theory: C, 56.35; H, 7.43; N, 9.39. Found: C, 57.36; H, 7.98; N, 10.40.

EXAMPLE 181

N-2-(4-N-(2-fluorobenzamido)phenyl)propyl 2-propanesulfonamide

The title compound 160 mg (75%) was prepared as a solid following the method of Example 179, starting from the product of Preparation 60 and using 2-fluorobenzoyl chloride. NMR was consistent with the proposed title structure. Field Desorption Mass Spectrum: $M^+$=378.3.

Analysis for $C_{19}H_{23}FN_2O_3S$: Theory: C, 60.30; H, 6.13; N, 7.40. Found: C, 59.51; H, 5.98; N, 7.11.

EXAMPLE 182

N-2-(4-N-(2-furylcarboxamido)phenyl)propyl 2-propanesulfonamide

The title compound 150 mg (47%) was prepared as a solid following the method of Example 179, starting from the product of Preparation 60 and using 2-furoyl chloride. NMR was consistent with the proposed title structure. Field Desorption Mass Spectrum: $M^+$=352.3. Analysis for $C_{17}H_{22}N_2O_4S$: Theory: C, 58.29; H, 6.33; N, 7.99. Found: C, 58.19; H, 6.81; N, 7.25.

EXAMPLE 183

N-2-(4-N-(2-thienylcarboxamido)phenyl)propyl 2-propanesulfonamide

The title compound 150 mg (33%) was prepared as a solid following the method of Example 1, starting from the product of Preparation 7 and using 2-thiophene chloride. NMR was consistent with the proposed title structure. Field Desorption Mass Spectrum: $M^+$=366.2.

Analysis for $C_{17}H_{22}N_2O_3S_2$: Theory: C, 55.71; H, 6.05; N, 7.64. Found: C, 55.59; H, 5.01; N, 7.80.

EXAMPLE 184

N-2-(4-N-(4-vinylbenzamido)phenyl)propyl 2-propanesulfonamide

The title compound 420 mg (56%) was prepared as a solid following the method of Example 179, starting from the product of Preparation 60 and using 4-vinylbenzoyl chloride. NMR was consistent with the proposed title structure. Field Desorption Mass Spectrum: $M^+$=387.2.

Analysis for $C_{21}H_{24}N_2O_3S$: Theory: C, 65.26; H, 6.78; N, 7.25. Found: C, 64.99; H, 6.69; N, 7.17.

EXAMPLE 185

N-2-(4-N-(4-iodobenzamido)phenyl)propyl 2-propanesulfonamide

The title compound 610 mg (73%) was prepared as a solid following the method of Example 179, starting from the product of Preparation 60 and using 4-iodobenzoyl chloride. NMR was consistent with the proposed title structure. Field Desorption Mass Spectrum: $M^+$=487.2.

Analysis for $C_{19}H_{23}N_2O_3S$: Theory: C, 46.91; H, 4.73; N, 5.76. Found: C, 47.13; H, 4.51; N, 5.60.

EXAMPLE 186

N-2-(4-(4-N-(1-(2-(2-propane)sulfonylamino)propyl benzamido)phenyl)propyl 2-propanesulfonamide A 0° C. solution of the material from Preparation 67 (210 mg, 0.77 mmol) in dry acetone (5 ml) was treated with N-methyl morpholine (120 mg, 1.2 mmol) and i-butyl chloroformate (120 mg, 0.85 mmol). The reaction mixture was stirred for 30 minutes. The solvent was removed and the resulting solid was dissolved in DMF (5 ml). The mixture was treated with aniline from Preparation 58 (220 mg, 0.85 mmol). The reaction mixture was stirred at room temperature for 16 h. Water (10 ml) was added to the mixture and organic was extracted with dichloromethane (3×10 ml). The combined organic fraction was washed with water (2×10 ml), brine (10 ml), dried over sodium sulfate, and concentrated to give crude product which was further purified by flash chromatography (SiO2, 30% EtOAc: Hexane) to provide 100 mg (25%) of the pure product. NMR was consistent with the proposed title structure. Field Desorption Mass Spectrum: $M^+$=509.8.

Analysis for $C_{24}H_{35}N_3O_5S_2$: Theory: C, 56.78; H, 6.55; N, 8.28. Found: C, 56.71; H, 6.64; N, 8.01.

EXAMPLE 187

N-2-(4-N-(cyclohexanecarboxamido)phenyl)propyl 2-propanesulfonamide

A solution of the material of Preparation 58 (20 mg, 0.08 mmol) in dry THF (1 ml) in a 4 ml teflon capped vial was treated with poly(4-vinylpyridine) 2% crosslinked resin (200 mg, 1.6 mmol) and appropriate acid chloride (1.2 equivalent, 0.096 mmol). The vial was shaken at room temperature for 24 h. The reaction was filtered though ion exchange column (0.5 g pre packed SCX 1211–3039) to remove the unreacted aniline. Aminomethyl-polystyrene (400 mg, 0.8 mmol) was added to the filtrate and the mixture was shaken at room temperature for 24 h. The reaction mixture was filtered through a cotton plug and the filtrate was concentrated to give pure amide. NMR of each amide was consistent with the proposed structure. Field Desorption Mass Spectrum: $M^+$=366.3.

EXAMPLE 188

N-2-(4-N-(4-fluorobenzamido)phenyl)propyl 2-propanesulfonamide

The title compound was prepared as a solid following the method of Example 187, starting from the product of Preparation 58 and using 4-fluorobenzoyl chloride. NMR was consistent with the proposed title structure. Field Desorption Mass Spectrum: $M^+$=378.2.

EXAMPLE 189

N-2-(4-N-(3-methylbenzamido)phenyl)propyl 2-propanesulfonamide

The title compound was prepared as a solid following the method of Example 187, starting from the product of Preparation 58 and using 3-methylbenzoyl chloride. NMR was consistent with the proposed title structure. Field Desorption Mass Spectrum: $M^+$=374.2.

EXAMPLE 190

N-2-(4-N-(3-trifluoromethylbenzamido)phenyl) propyl 2-propanesulfonamide

The title compound was prepared as a solid following the method of Example 187, starting from the product of Preparation 58 and using 3-methylbenzoyl chloride. NMR was consistent with the proposed title structure. Field Desorption Mass Spectrum: $M^+$=428.2.

EXAMPLE 191

N-2-(4-N-(2-trifluoromethylbenzamido)phenyl) propyl 2-propanesulfonamide

The title compound was prepared as a solid following the method of Example 187, starting from the product of Preparation 58 and using 2-trifluoromethylbenzoyl chloride. NMR was consistent with the proposed title structure. Field Desorption Mass Spectrum: $M^+$=428.2.

EXAMPLE 192

N-2-(4-N-(3-fluorobenzamido)phenyl)propyl 2-propanesulfonamide

The title compound was prepared as a solid following the method of Example 187, starting from the product of Preparation 58 and using 3-fluorobenzoyl chloride. NMR was consistent with the proposed title structure. Field Desorption Mass Spectrum: $M^+=378.2$.

EXAMPLE 193

N-2-(4-N-(2-methoxybenzamido)phenyl)propyl 2-propanesulfonamide

The title compound was prepared as a solid following the method of Example 187, starting from the product of Preparation 58 and using 2-methoxybenzoyl chloride. NMR was consistent with the proposed title structure. Field Desorption Mass Spectrum: $M^+=390.2$

EXAMPLE 194

N-2-(4-N-(3-methoxybenzamido)phenyl)propyl 2-propanesulfonamide

The title compound was prepared as a solid following the method of Example 187, starting from the product of Preparation 58 and using 3-methoxybenzoyl chloride. NMR was consistent with the proposed title structure. Field Desorption Mass Spectrum: $M^+=390.2$.

EXAMPLE 195

N-2-(4-N-(4-t-butylbenzamido)phenyl)propyl 2-propanesulfonamide

The title compound was prepared as a solid following the method of Example 187, starting from the product of Preparation 58 and using 4-t-butylbenzoyl chloride. NMR was consistent with the proposed title structure. Field Desorption Mass Spectrum: $M^+=416.2$.

EXAMPLE 196

N-2-(4-N-(2,4-difluorobenzamido)phenyl)propyl 2-propanesulfonamide

The title compound was prepared as a solid following the method of Example 187, starting from the product of Preparation 58 and using 2,4-difluorobenzoyl chloride. NMR was consistent with the proposed title structure. Field Desorption Mass Spectrum: $M^+=396.2$.

EXAMPLE 197

N-2-(4-N-(4-methoxybenzamido)phenyl)propyl 2-propanesulfonamide

The title compound was prepared as a solid following the method of Example 187, starting from the product of Preparation 58 and using 4-methoxybenzoyl chloride. NMR was consistent with the proposed title structure. Field Desorption Mass Spectrum: $M^+=390.2$.

EXAMPLE 198

N-2-(4-N-(4-ethylbenzamido)phenyl)propyl 2-propanesulfonamide

The title compound was prepared as a solid following the method of Example 187, starting from the product of Preparation 58 and using 4-ethylbenzoyl chloride. NMR was consistent with the proposed title structure. Field Desorption Mass Spectrum: $M^+=388.2$.

EXAMPLE 199

N-2-(4-N-(cyclobutylcarboxamido)phenyl)propyl 2-propanesulfonamide

The title compound was prepared as a solid following the method of Example 187, starting from the product of Preparation 58 and using cyclobutane carbonyl chloride. NMR was consistent with the proposed title structure. Field Desorption Mass Spectrum: $M^+=338.2$.

EXAMPLE 200

N-2-(4-N-(phenylacetamido)phenyl)propyl 2-propanesulfonamide

The title compound was prepared as a solid following the method of Example 187, starting from the product of Preparation 58 and using phenylacetyl chloride. NMR was consistent with the proposed title structure. Field Desorption Mass Spectrum: $M^+=374.2$

EXAMPLE 201

N-2-(4-N-(4-methylbenzamido)phenyl)propyl 2-propanesulfonamide

The title compound was prepared as a solid following the method of Example 187, starting from the product of Preparation 58 and using 4-methylbenzoyl chloride. NMR was consistent with the proposed title structure. Field Desorption Mass Spectrum: $M^+=374.2$.

EXAMPLE 202

N-2-(4-N-3-(5-methyl)isoxazolyl)carboxamido)phenyl)propyl 2-propanesulfonamide

The title compound was prepared as a solid following the method of Example 187, starting from the product of Preparation 58 and using 5-methyl-3-isoxazole acid chloride. NMR was consistent with the proposed title structure. Field Desorption Mass Spectrum: $M^+=365.2$.

EXAMPLE 203

N-2-(4-N-((2-fluoro4-trifluoromethyl)-benzamido)phenyl)propyl 2-propanesulfonamide The title compound was prepared as a solid following the method of Example 187, starting from the product of Preparation 58 and using 2-fluoro-4-(trifluoromethyl)-benzoyl chloride. NMR was consistent with the proposed title structure. Field Desorption Mass Spectrum: $M^+=446.1$.

EXAMPLE 204

N-2-(4-N-(4-trifluoromethylbenzamido)phenyl)propyl 2-propanesulfonamide

The title compound was prepared as a solid following the method of Example 187, starting from the product of Preparation 58 and using 4-(trifluoromethyl)benzoyl chloride. NMR was consistent with the proposed title structure. Field Desorption Mass Spectrum: $M^+=444.1$.

EXAMPLE 205

N-2-(4-N-(4-n-butyloxybenzamido)phenyl)propyl 2-propanesulfonamide

The title compound was prepared as a solid following the method of Example 187, starting from the product of Preparation 58 and using 4-n-butyloxybenzoyl chloride. NMR was consistent with the proposed title structure. Field Desorption Mass Spectrum: $M^+$=432.2.

EXAMPLE 206

N-2-(4-N-(cyclopropylcarboxamido)phenyl)propyl 2-propanesulfonamide

The title compound was prepared as a solid following the method of Example 187, starting from the product of Preparation 58 and using cyclopropane carbonyl chloride. NMR was consistent with the proposed title structure. Field Desorption Mass Spectrum: $M^+$=324.2.

EXAMPLE 207

N-2-(4-N-(cyclopentylcarboxamido)phenyl)propyl 2-propanesulfonamide

The title compound was prepared as a solid following the method of Example 187, starting from the product of Preparation 58 and using cyclopentane carbonyl chloride. NMR was consistent with the proposed title structure. Field Desorption Mass Spectrum: $M^+$=353.

EXAMPLE 208

N-2-(4-N-(ethylcarboxamido)phenyl)propyl 2-propanesulfonamide

The title compound was prepared as a solid following the method of Example 187, starting from the product of Preparation 58 and using propionyl chloride. NMR was consistent with the proposed title structure. Field Desorption Mass Spectrum: $M^+$=312.

EXAMPLE 209

N-2-(4-N-(propylcarboxamido)phenyl)propyl 2-propanesulfonamide

The title compound was prepared as a solid following the method of Example 187, starting from the product of Preparation 58 and using butanoyl chloride. NMR was consistent with the proposed title structure. Field Desorption Mass Spectrum: $M^+$=326.

EXAMPLE 210

N-2-(4-N-(5-isoxazolylcarboxamido)phenyl)propyl 2-propanesulfonamide

The title compound was prepared as a solid following the method of Example 187, starting from the product of Preparation 58 and using 5-isoxazole acid chloride. NMR was consistent with the proposed title structure. Field Desorption Mass Spectrum: $M^+$=351.

EXAMPLE 211

N-2-(4-N-(2-benzothiophenylcarboxamido)phenyl) propyl 2-propanesulfonamide

The title compound was prepared as a solid following the method of Example 187, starting from the product of Preparation 58 and using 2-benzothiophene acid chloride. NMR was consistent with the proposed title structure. Field Desorption Mass Spectrum: $M^+$=416.

EXAMPLE 212

N-2-(4-N-(4-phenylbenzamido)phenyl)propyl 2-propanesulfonamide

The title compound was prepared as a solid following the method of Example 187, starting from the product of Preparation 58 and using 4-phenylbenzoyl chloride. NMR was consistent with the proposed title structure. Field Desorption Mass Spectrum: $M^+$=436.

EXAMPLE 213

N-2-(4-N-(4-propylbenzamido)phenyl)propyl 2-propanesulfonamide

The title compound was prepared as a solid following the method of Example 187, starting from the product of Preparation 58 and using 4-propylbenzoyl chloride. NMR was consistent with the proposed title structure. Field Desorption Mass Spectrum: $M^+$=402.

EXAMPLE 214

N-2-(4-N-(4-cyanobenzamido)phenyl)propyl 2-propanesulfonamide

The title compound was prepared as a solid following the method of Example 187, starting from the product of Preparation 58 and using 4-cyanobenzoyl chloride. NMR was consistent with the proposed title structure. Field Desorption Mass Spectrum: $M^+$=385.

EXAMPLE 215

N-2-(4-N-(2-thiophenylacetamido)phenyl)propyl 2-propanesulfonamide

The title compound was prepared as a solid following the method of Example 187, starting from the product of Preparation 58 and using 2-thiophene acetyl chloride. NMR was consistent with the proposed title structure. Field Desorption Mass Spectrum: $M^+$=380

EXAMPLE 216

N-2-(4-N-4-(3-phenyl-5-methyl)isoxazolyl)-carboxamidophenyl)propyl 2-propanesulfonamide The title compound was prepared as a solid following the method of Example 187, starting from the product of Preparation 58 and using 3-phenyl-5-methyl-4-isoxazole acid chloride. NMR was consistent with the proposed title structure. Field Desorption Mass Spectrum: $M^+$=441.

EXAMPLE 217

N-2-(4-N-(4-morpholinylcarboxamido)phenyl) propyl 2-propanesulfonamide

The title compound was prepared as a solid following the method of Example 187, starting from the product of Preparation 58 and using 4-morpholine carbonyl chloride. NMR was consistent with the proposed title structure. Field Desorption Mass Spectrum: $M^+$=369.

EXAMPLE 218

N-2-(4-N-(isonicotinylamido)phenyl)propyl 2-propanesulfonamide

The title compound was prepared as a solid following the method of Example 187, starting from the product of Preparation 58 and using isonicotinoyl chloride. NMR was consistent with the proposed title structure. Field Desorption Mass Spectrum: $M^+$=361.

EXAMPLE 219

N-2-(4-N-(3-chlorobenzamido)phenyl)propyl 2-propanesulfonamide

The title compound was prepared as a solid following the method of Example 187, starting from the product of Preparation 58 and using 3-chlorobenzoyl chloride. NMR was consistent with the proposed title structure. Field Desorption Mass Spectrum: $M^+=395$.

EXAMPLE 220

N-2-(4-N-(4-bromobenzamido)phenyl)propyl 2-propanesulfonamide

The title compound was prepared as a solid following the method of Example 187, starting from the product of Preparation 58 and using 4-bromobenzoyl chloride. NMR was consistent with the proposed title structure. Field Desorption Mass Spectrum: $M^+=439.4$.

EXAMPLE 221

N-2-(4-N-(4-chlorobenzamido)phenyl)propyl 2-propanesulfonamide

The title compound was prepared as a solid following the method of Example 187, starting from the product of Preparation 58 and using 4-chlorobenzoyl chloride. NMR was consistent with the proposed title structure. Field Desorption Mass Spectrum: $M^+=395$.

EXAMPLE 222

N-2-(4-N-(methyloxalylamido)phenyl)propyl 2-propanesulfonamide

The title compound was prepared as a solid following the method of Example 187, starting from the product of Preparation 58 and using methyl oxalyl chloride. NMR was consistent with the proposed title structure. Field Desorption Mass Spectrum: $M^+=343$.

EXAMPLE 223

N-2-(4-N-(phenoxyacetamido)phenyl)propyl 2-propanesulfonamide

The title compound was prepared as a solid following the method of Example 187, starting from the product of Preparation 58 and using phenoxy acetyl chloride. NMR was consistent with the proposed title structure. Field Desorption Mass Spectrum: $M^+=391$.

EXAMPLE 224

N-2-(4-N-(acryloylamido)phenyl)propyl 2-propanesulfonamide

The title compound was prepared as a solid following the method of Example 187, starting from the product of Preparation 58 and using acryloyl chloride. NMR was consistent with the proposed title structure. Field Desorption Mass Spectrum: $M^+=311$.

EXAMPLE 225

N-2-(4-N-(5-nitro-2-furylcarboxamido)phenyl) propyl 2-propanesulfonamide

The title compound was prepared as a solid following the method of Example 187, starting from the product of Preparation 58 and using 5-nitro-2-furoyl chloride. NMR was consistent with the proposed title structure. Field Desorption Mass Spectrum: $M^+=396$.

EXAMPLE 226

N-2-(4-N-(6-chloronicotinylcarbamido)phenyl) propyl 2-propanesulfonamide

The title compound was prepared as a solid following the method of Example 187, starting from the product of Preparation 58 and using 6-chioronicotinyl chloride. NMR was consistent with the proposed title structure. Field Desorption Mass Spectrum: $M^+=396$.

EXAMPLE 227

N-2-(4-N-(piconioylcarbamido)phenyl)propyl 2-propanesulfonamide

The title compound was prepared as a solid following the method of Example 187, starting from the product of Preparation 58 and using piconioyl chloride. NMR was consistent with the proposed title structure. Field Desorption Mass Spectrum: $M^+=362$.

EXAMPLE 228

N-2-(4-N-(2-(S)-(–)-N-(trifluoroacetyl) pyrroidinylcarboxamido)phenyl)propyl 2-propanesulfonamide The title compound was prepared as a solid following the method of Example 187, starting from the product of Preparation 58 and using (S)-(–)-N-(trifluoroacetyl)-prolyl chloride. NMR was consistent with the proposed title structure. Field Desorption Mass Spectrum: $M^+=450$.

EXAMPLE 229

N-2-(4-N-(pivaloylcarbamido)phenyl)propyl 2-propanesulfonamide

The title compound was prepared as a solid following the method of Example 187, starting from the product of Preparation 58 and using pivaloyl chloride. NMR was consistent with the proposed title structure. Field Desorption Mass Spectrum: $M^+=341$.

EXAMPLE 230

N-2-(4-N-(3-acetylphenylurea)phenyl)propyl 2-propanesulfonamide

A solution of the material of Preparation 58 (15 mg, 0.058 mmol) in dry THF (1 ml) in a 4 ml teflon capped vial was treated with 3-acetylphenylisocynat (12 mg, 0.073 mmol). The reaction mixture was shaken for 16 h. Aminomethylpolystyrene resin (150 mg, 0.3 mmol) was added to the reaction mixture and let this mixture stir for 2 h. The reaction was filtered though ion exchange column (0.5 g pre packed SCX 1211–3039) to remove the unreacted aniline. The reaction mixture was filtered through a cotton plug and the filtrate was concentrated to give 32 mg of the pure amide. NMR of the product was consistent with the proposed structure. Field Desorption Mass Spectrum: $M^+=417.5$.

EXAMPLE 231

N-2-(4-N-(2-(2-thienyl)ethylurea)phenyl)propyl 2-propanesulfonamide

A solution of the material of Preparation 58 (15 mg, 0.058 mmol) in dry THF (1 ml) in a 4 ml teflon capped vial was treated with 2(thien-2-yl)ethylisocynate (12 mg, 0.073 mmol). The reaction mixture was shaken for 16 h. Aminomethylpolystyrene resin (150 mg, 0.3 mmol) was added to the reaction mixture and let this mixture stir for 2 h. The reaction was filtered though ion exchange column (0.5 g pre packed SCX 1211-3039) to remove the unreacted aniline. The reaction mixture was filtered through a cotton plug and the filtrate was concentrated to give 26.5 mg of the pure amide. NMR of the product was consistent with the proposed structure. Field Desorption Mass Spectrum: M$^+$=409.6.

EXAMPLE 232

N-2-(4-(4-N-benzylpiperazino)phenyl)propyl 2-propanesulfonamide

A solution of the material from Preparation 73 (80 mg, 0.18 mmol) in dry tetrahydrofuran (10 ml) was treated with borane methylsulfide (1 M in THF, 3 ml, 3 mmol). The reaction mixture was stirred while refluxing for 4 h. The solution was cooled down to room temperature and was treated with 5N sodium hydroxide (5 ml) and methanol (5 ml). The mixture was refluxed for 12 h. The reaction mixture was cooled to room temperature and water (10 ml) was added to the mixture. Organic was extracted with ethyl acetate (3×10 ml). The combined organic fraction was washed with water (2×10 ml), brine (10 ml), dried over potassium carbonate, and concentrated in vacuo to give the crude material which was further purified by flash chromatography (SiO$_2$, 30% dichloromethane: EtOAc) to give 34 mg (45%) of the pure product. NMR was consistent with the proposed title structure. Field Desorption Mass Spectrum: M$^+$=436.

Analysis for C$_{23}$H$_{33}$N$_3$OS: Theory: C, 66.47; H, 8.00; N, 10.11. Found: C, 65.72; H, 7.89; N, 9.68.

EXAMPLE 233

N-2-(4-(4-methylpiperazino)phenyl)propyl 2-propanesulfonamide

A solution of the material from Preparation 72 (80 mg, 0.18 mmol) in formic acid (0.7 ml) was treated with formaldehyde (0.7 ml, 37%). The reaction mixture was heated at 80° C. for 1 h and then was cooled to room temperature. Water (10 ml) was added to the mixture. The pH of the mixture was brought to 10 by the addition of 1N sodium hydroxide. Organic was extracted with ethyl acetate (3×10 ml). The combined organic fraction was washed with water (2×10 ml), brine (10 ml), dried over potassium carbonate, and concentrated in vacuo to 10 give the crude material which was further purified by flash chromatography (SiO$_2$, 10% methanol: dichloromethane) to give 46 mg (75%) of the pure product. NMR was consistent with the proposed title structure. Field Desorption Mass Spectrum: M$^+$=436.

Analysis for C$_{17}$H$_{29}$N$_3$O$_2$S: Theory: C, 60.14; H, 8.61; N, 12.38. Found: C, 59.31; H, 8.57; N, 11.58.

EXAMPLE 234

N-2-(4-(2-thienyl)methylaminophenyl)propyl 2-propanesulfonamide

A solution of the product from Preparation 58 (0.15 g, 0.42 mmol) in methanol (3 ml) and glacial acetic acid (1 drop) was treated with 2-thiophenecarboxaldehyde (0.031 g, 0.28 mmol). The reaction was stirred at ambient for 90 minutes and sodium borohydride (0.015 g, 0.42 mmol) added. The reaction was stirred for 16 h. Water (5 ml) was added and the organic extracted with methylene chloride (2×10 ml). The combined organic layers were washed with brine, dried over magnesium sulfate and concentrated. The crude product was dissolved in methylene chloride (3 ml) and TFA (5 drops) added. The reaction was stirred for 3 h at ambient, then water added (3 ml). The organic was extracted with methylene chloride (2×10 ml). The combined organic layers were washed with brine, dried over magnesium sulfate and concentrated. The crude title product was purified by flash chromatography (SiO$_2$, 30% EtOAc: hexanes) to give 0.060 g (60%) of the pure product. NMR was consistent with the proposed title structure. Field Desorption Mass Spectrum: M$^+$=353.

Analysis for C$_{17}$H$_{24}$N$_2$O$_2$S$_2$: Theory: C, 57.92; H, 6.86; N, 7.95. Found: C, 58.11; H, 6.71; N, 7.79.

EXAMPLE 235

N-2-(4-(2-furyl)methylaminophenyl)propyl 2-propanesulfonamide

The title compound 80 mg (85%) was prepared as an oil following the method of Example 234, starting from the material of Preparation 58 and using 2-furaldehyde. NMR was consistent with the proposed title structure. Field Desorption Mass Spectrum: M$^+$=336.

Analysis for C$_{17}$H$_{24}$N$_2$O$_3$S: Theory: C, 60.69; H, 7.19; N, 8.33. Found: C, 60.52; H, 7.03; N, 8.45.

EXAMPLE 236

N-2-(4-(3-thienyl)methylaminophenyl)propyl 2-propanesulfonamide

The title compound 70 mg (54%) was prepared as an oil following the method of Example 234, starting from the product of Preparation 58 and using 3-thiophene-carboxaldehyde. NMR was consistent with the proposed title structure. Field Desorption Mass Spectrum: M$^+$=336.1.

Analysis for C$_{17}$H$_{24}$N$_2$O$_3$S: Theory: C, 60.69; H, 7.19; N, 8.33. Found: C, 60.89; H, 7.16; N, 8.09.

EXAMPLE 237

N-2-(4-(3-furyl)methylaminophenyl)propyl 2-propanesulfonamide

The title compound 40 mg (21%) was prepared as an oil following the method of Example 234, starting from the product of Preparation 58 and using 3-furaldehyde. NMR was consistent with the proposed title structure. Field Desorption Mass Spectrum: M$^+$=352.

Analysis for C$_{17}$H$_{24}$N$_2$O$_2$S$_2$: Theory: C, 57.92; H, 6.86; N, 7.95. Found: C, 57.80; H, 6.63; N, 7.78.

EXAMPLE 238

N-2-(4-(2-fluorophenyl)methylamino)phenyl)propyl 2-propanesulfonamide

The title compound 52 mg (52%) was prepared as an oil following the method of Example 234, starting from the product of Preparation 58 and using 2-fluoro-benzaldehyde. NMR was consistent with the proposed title structure. Field Desorption Mass Spectrum: M$^+$=xxx.

Analysis for C$_{19}$H$_{25}$FN$_2$O$_2$S:

EXAMPLE 239

N-2-(4-morpholinophenyl)propyl 2-propanesulfonamide

The title compound 70 mg (47%) was prepared as an oil following the method of Preparation 65, starting from the product of Preparation 39 (part 1) and using morpholine. NMR was consistent with the proposed title structure. Field Desorption Mass Spectrum M$^+$=xxx Analysis for C$_{16}$H$_{26}$N$_2$O$_3$S:

EXAMPLE 240

N-2-(4-(2-fluorophenyl)methoxyphenyl)propyl 2-propanesulfonamide

A solution of the product of Preparation 36 (0.3 g, 0.84 mmol) in dry DMF (20 ml) was treated with sodium hydride (0.037 g, 0.92 mmol) and 2-fluorobenzyl bromide (0.17 g, 0.92 mmol. The reaction mixture was stirred at ambient for 5 h. Water (10 ml) was added and the organic extracted with ether(2×30 ml). The combined organic layers were washed with brine (20 ml), dried over magnesium sulfate, and concentrated in vacuo. The crude material was taken up in methylene chloride (20 ml) and TFA (2 ml) added. The reaction mixture was stirred at ambient for 3 h. Water (5 ml) was added and the organic extracted with methylene chloride (2×20 ml). The combined organic layers were washed with brine (20 ml), dried over magnesium sulfate, and concentrated in vacuo. The crude product was further purified by flash chromatography (SiO2, 30% EtOAc: hexanes) to give 0.25 g (82%) of a white solid as a pure product. NMR was consistent with the proposed title structure. Field Desorption Mass Spectrum: M+=365.

Analysis for $C_{19}H_{24}FNO_3S$: Theory: C, 62.44; H, 6.62; N, 3.83. Found: C, 62.42; H, 6.59; N, 3.76.

EXAMPLE 241

N-2-(4-(2-tetrahydrofuryl)methoxyphenyl)propyl 2-propanesulfonamide

The title compound 150 mg (52%) was prepared as a solid following the method of Example 240, starting from the product of Preparation 36 and using tetrahydro-furfuryl bromide. NMR was consistent with the proposed title structure. Field Desorption Mass Spectrum: M+=341.1.

Analysis for $C_{17}H_{27}NO_4S$: Theory: C, 59.80; H, 7.97; N, 4.10. Found: C, 59.84; H, 8.00; N, 3.80.

EXAMPLE 242

N-2-(4-benzoylmethylphenyl)propyl 2-propanesulfonamide

A solution of the product of Preparation 39 (1.0 g, 3.2 mmol) in dry, degassed tetrahydrofuran (25 ml) was treated with palladium chloride (0.028 g, 0.16 mmol), tri-o-tolylphosphine (0.097 g, 0.32 mmol), tributyl-influoride (1.0 g, 3.4 mmol), and 1-phenyl-1-(trimethylsiloxy)ethylene (1.0 ml, 4.8 mmol). The reaction mixture was heated to reflux for 16 h. Water (50 ml) was added to the mixture and the organic layer was extracted with ether (3×50 ml). The combined organic layers were washed with brine (50 ml), dried over magnesium sulfate, and concentrated in vacuo to give the crude product which was further purified by flash chromatography (SiO$_2$, 30% EtOAc: Hexanes) to give 0.28 g (24%) of an orange solid as a pure product. NMR was consistent with the proposed title structure. Ion Spray Mass Spectrum: M+=1=360.0, M−1=358.0.

Analysis for $C_{20}H_{25}NO_3S$: Theory: C, 66.82; H, 7.01; N, 3.90. Found: C, 66.86; H, 7.16; N, 3.85.

EXAMPLE 243

N-2-(4-acetylphenyl)propyl 2-propanesulfonamide

A −80° C. solution of the product of Preparation 39 (2.0 g, 6.4 mmol) in dry THF (30 ml) was slowly treated with a solution of nBuLi (8.0 ml, 13.5 mmol, 1.7M solution in hexanes). The reaction was stirred at −80C. for 30 min and then treated with dimethylacetamide (0.6 ml, 12.8 mmol). The reaction was treated with an aqueous, saturated solution of ammonium chloride at −80° C. (2 ml). Water (30 ml) was added to the mixture and the organic layer extracted with ether (2×50 ml). The combined organic layers were washed with brine (50 ml), dried over magnesium sulfate and concentrated. The crude product was further purified by flash chromatography (SiO$_2$, 30% EtOAc: hexanes) to give 1.0 g (55%) of a white solid as the pure product. NMR was consistent with the proposed title structure. Field Desorption Mass Spectrum: M+=283.0.

Analysis for $C_{14}H_{21}NO_3S$: Theory: C, 59.34; H, 7.47; N, 4.94. Found: C, 59.36; H, 7.65; N, 5.10.

EXAMPLE 244

N-2-(4-cyclopropylcarbanoylphenyl)propyl 2-propanesulfonamide

A 0° C. solution of the product of Preparation 67 (0.18 g, 0.63 mmol) in acetone was treated with 4-methyl morpholine (0.095 g, 0.94 mmol), and isobutyl chloroformate (0.094 g, 0.69 mmol). The reaction mixture was stirred for 30 min and concentrated in vacuo. The resulting white solid was taken up in DMF and cyclopropylamine (0.040 g, 0.69 mmol), and DMAP (catalytic) added. The reaction mixture was stirred for 16 h at ambient temperature. Water (5 ml) was added and the organic extracted with methylene chloride (2×20 ml). The combined organic layers were washed with an aqueous saturated solution of NaHSO$_4$(20 ml), brine (20 ml), dried over magnesium sulfate and concentrated in vacuo. The crude material was purified by flash chromatography (SiO$_2$, 30% EtOAc: hexanes) to give 0.09 g (56%) of a white solid as a pure product. NMR was consistent with the proposed title structure. Field Desorption Mass Spectrum: M+=324.2.

Analysis for $C_{16}H_{24}N_2O_3S$: Theory: C, 59.23; H, 7.46; N, 8.63. Found: C, 59.35; H, 7.69; N, 8.53.

EXAMPLE 245

N-2-(4-cyclopentylcarbanoylphenyl)propyl 2-propanesulfonamide

The title compound 90 mg (41%) was prepared as a solid following the method of Example 244, starting from the material of Preparation 67 and using cyclopentyl-amine. NMR was consistent with the proposed title structure. Filed Desorption Mass Spectrum: M+=352.2.

Analysis for $C_{18}H_{28}N_2O_3S$: Theory: C, 61.33; H, 8.01; N, 7.95. Found: C, 61.08; H, 7.78; N, 8.07.

EXAMPLE 246

N-2-(4-(2-fluorophenyl)carbanoylphenyl)propyl 2-propanesulfonamide

The title compound 105 mg (50%) was prepared as a solid following the method of Example 244, starting from the material of Preparation 67 and using 2-fluoroaniline. NMR was consistent with the proposed title structure. Field Desorption Mass Spectrum: M+=378.

Analysis for $C_{18}H_{28}N_2O_3S$: Theory: C, 61.20; H, 6.42; N, 7.14. Found: C, 61.12; H, 6.27; N, 6.87.

EXAMPLE 247

N-2-(4-benzylsulfonylaminophenyl)propyl 2-propanesulfonamide

The title compound 63 mg (82%) was prepared as a solid following the method of Example 179, starting from the

EXAMPLE 248

N-2-(4-(2-thienyl)sulfonylamino)phenyl)propyl 2-propanesulfonamide

The title compound was prepared as a solid following the method of Example 187, starting from the product of Preparation 58 and using 2-thienylsulfonyl chloride. NMR was consistent with the proposed title structure. Field Desorption Mass Spectrum: M$^+$=428.2.

EXAMPLES 249 AND 250

N-2-(4-(3-oxocyclopentyl)phenyl)propyl 2-propanesulfonamide (A) and N-2-(4-(3-hydroxycyclopentyl)phenyl)propyl 2-propanesulfonamide (B)

A solution of the material from Preparation 75 (0.15 g, 0.47 mmol) in EtOAc (5 ml) was treated with palladium on carbon (0.02 g, 10 mole %) under a hydrogen atmosphere. The mixture was stirred at ambient for 4 h and then heated to 50° C. for 2 h. The reaction was filtered through a celite cake and the filtrate concentrated in vacuo. The crude mixture of both title products was purified by flash chromatography (SiO$_2$, 70% EtOAc: hexanes) to give 0.06 g (40%) of the first title compound (A) and 0.05 g (33%) of the second title (B).
(A) NMR was consistent with the proposed title structure.
Field Desorption Mass Spectrum: M$^+$=323.
Analysis for C$_{17}$H$_{25}$NO$_3$S: Theory: C, 63.13; H, 7.91; N, 4.33. Found: C, 63.34; H, 7.76; N, 4.30.
(B) NMR was consistent with the proposed title structure.
Field Desorption Mass Spectrum: M$^+$=325.
Analysis for C$_{17}$H$_{27}$NO$_3$S: Theory: C, 62.74; H, 8.36; N, 4.30. Found: C, 62.54; H, 8.27; N, 4.24.

EXAMPLE 251

N-2-(4-(2-hydroxy-2-phenyl(ethylphenyl)propyl 2-propanesulfonamide

A solution of the title compound from Example 242 (65 mg, 0.18 mmol) in ethanol (5 ml) was treated with sodium borohydride (9 mg, 0.22 mmol). The reaction mixture was stirred for 2 h and water (2 ml) added slowly. The mixture was extracted with methylene chloride (2×10 ml). The combined organic layers were washed with brine 95 ml), dried over magnesium sulfate and concentrated in vacuo. The resulting crude product was diluted with EtOAc and filtered through a 1 inch silica gel plus and concentrated in vacuo to give 61 mg (94%) of a colorless oil as a pure product. NMR was consistent with the proposed title structure. Field Desorption Mass Spectrum M$^+$=361.
Analysis for C$_{20}$H$_{27}$NO$_3$S: Theory: C, 66.45; H, 7.53; N, 3.87. Found: C, 66.36; H, 7.77; N, 3.63.

EXAMPLE 252

N-2-(4-formylphenyl)propyl 2-propanesulfonamide

The title compound 1.18 g (68%) was prepared as a solid following the method of Example 243, starting from the product of Preparation 39 and using dimethyl-formamide. NMR was consistent with the proposed title structure. Field Desorption Mass Spectrum: M$^+$=269.3.

Analysis for C$_{13}$H$_{19}$NO$_3$S: Theory: C, 57.97; H, 7.11; N, 5.20. Found: C, 57.78; H, 6.95; N, 5.00.

EXAMPLE 253

N-2-(4-(1-pyrrolidinyl)phenyl)propyl 2-propanesulfonamide

A solution of material from Preparation 60 (0.17 g, 0.45 mmol) in DMF (20 ml) was treated with diiodobutane (0.15 g, 0.95 mmol) followed by sodium hydride (38 mg, 0.47 mmol). The reaction mixture was heated to 70° C. for 4 h. Water (10 ml) was added and the organic extracted with ether (2×20 ml). The combined organic layers were washed with brine (10 ml), dried over magnesium sulfate and concentrated. The crude product was further purified by flash chromatography (SiO$_2$, 20% EtOAc: hexanes) to give 0.10 g of an oil. This oil was diluted with methylene chloride (10 ml) and TFA (2 ml) added. The reaction was stirred at ambient for 3 h. Water (5 ml) was added and the organic further washed with brine (5 ml), dried over magnesium sulfate and concentrated in vacuo. Flash chromatography (SiO2, 30% EtOAc: hexanes) gave 20 mg (14%) of a white solid as the pure product. NMR was consistent with the proposed title structure. Field Desorption Mass Spectrum: M$^+$=310.2.

EXAMPLE 254

N-2-(4-N-(benzamido)phenyl)-2-methylpropyl 2-propanesulfonamide

To a solution of the amine from Preparation 82 (150 mg, 0.56 mmol) and triethylamine (65 mg, 1.1 eq) in dichloromethane (20 ml) was added dropwise benzoyl chloride (87 mg., 1.1 Eq)in dichloromethane (5 ml) at room temperature under nitrogen. After 1 hour, the reaction was complete. The solution was washed once with H$_2$O, dried over K$_2$CO$_3$, and concentrated under reduced pressure to yield 206 mg. of a solid. Material was recrystallized from hexane/ethyl acetate 5:1 to yield 141 mg. as crystals. m.p. 202.5°–204° C. (67%). NMR was consistent with the proposed title structure. Field Desorption Mass Spectrum: M$^+$375
Analysis for C$_{20}$H$_{26}$N$_2$O$_3$S: Theory: C, 64.14; H, 7.00; N, 7.48. Found: C, 64.20; H, 7.25; N, 7.58.

EXAMPLE 255

N-2-(4-N-(cyclobutylcarboxamido)phenyl)-2-methylpropyl 2-propanesulfonamide

The title compound was prepared as a solid following the method of Example 254, starting from the product of Preparation 82 (100 mg, 0.37 mmol) and triethylamine (45 mg., 1.2 Eq.) was treated with cyclobutanecarbonyl chloride (48 mg., 1.1 Eq). The resulting solid was recrystallized from ethyl acetate/hexane 4:1 to yield 74 mg. of crystals. m.p. 186°–188° C. (57%). NMR was consistent with the proposed title structure. Field Desorption Mass Spectrum: M$^+$353 Analysis for C$_{18}$H$_{28}$N$_2$O$_3$S: Theory: C, 61.33; H, 8.01; N, 7.95. Found: C, 61.51; H, 7.77; N, 7.80.

EXAMPLE 256

N-2-(4-N-(propanoylamido)phenyl)-2-methylpropyl 2-propanesulfonamide

The title compound was prepared as a solid following the method of Example 254, starting from the product of Preparation 82 (100 mg, 0.37 mmol) and triethylamine (45 mg., 1.2 Eq.) was treated with propanoyl chloride (40 mg., 1.1 Eq.). The resulting solid was recrystallized from ethyl acetate/hexane 4:1 to yield 75 mg. of crystals. m.p. 154°–155° C. (58%). NMR was consistent with the proposed title structure. Field Desorption Mass Spectrum: M$^+$327 Analysis for $C_{16}H_{26}N_2O_3S$: Theory: C, 58.87; H, 8.03; N, 8.58. Found: C, 58.96; H, 7.75; N, 8.54.

EXAMPLE 257

N-2-(4-N-(2-thienylcarboxamido)phenyl)-2-methylpropyl 2-propanesulfonamide

The title compound was prepared as a solid following the method of Example 254, starting from the product of Preparation 82 (100 mg, 0.37 mmol) and treating with 2-thiophene chloride (66 mg., 1.2 Eq.). The resulting solid was recrystallized from ethyl acetate/hexane 2:1 to yield 77 mg. of crystals. m.p. 183°–185° C. (55%). NMR was consistent with the proposed title structure. Field Desorption Mass Spectrum: M$^+$381 Analysis for $C_{18}H_{24}N_2O_3S_2$: Theory: C, 56.81; H, 6.36; N, 7.36. Found: C, 56.90; H, 6.57; N, 7.39.

EXAMPLE 258

N-2-(4-N-(3-(5-methyl)isoxazolylcarboxamido)phenyl)-2-methylpropyl 2-propanesulfonamide The title compound was prepared as a solid following the method of Example 254, starting from the product of Preparation 82 (100 mg, 0.37 mmol) and triethylamine (45 mg., 1.2 Eq.) was treated with 5-methyl-3-isoxazole acid chloride (68 mg., 1.2 Eq.). The resulting solid was recrystallized from hexane/ethyl acetate 1:1 to yield 83 mg. of crystals. m.p. 118°–120° C. (59%) NMR was consistent with the proposed title structure. Field Desorption Mass Spectrum: M$^+$380 Analysis for $C_{18}H_{25}N_3O_4S$ Theory: C, 56.97; H, 6.64; N, 11.07. Found: C, 57.11; H, 6.68; N, 11.16.

EXAMPLE 259

N-2-(4-N-(phenoxymethylcarboxamido)phenyl)-2-methylprolyl 2-propanesulfonamide

The title compound was prepared as a solid following the method of Example 254, starting with the product of Preparation 82 (100 mg, 0.37 mmol) and triethylamine (45 mg., 1.2 Eq.) was treated with phenoxyacetyl chloride (76 mg., 1.2 Eq.). The resulting solid was recrystallized from hexane/ethyl acetate 1:1 to yield 80 mg. of crystals. m.p. 143°–144° C. (54%). NMR was consistent with the proposed title structure. Field Desorption Mass Spectrum: M$^+$405

Analysis for $C_{21}H_{28}N_2O_4S$: Theory: C, 62.35; H, 6.98; N, 6.93. Found: C, 62.37; H, 6.83; N, 6.74.

EXAMPLE 260

N-2-(4-N-(4-ethylbenzamido)phenyl)-2-methylpropyl 2-propanesulfonamide

The title compound was prepared as a solid following the method of Example 254, starting with the product of Preparation 82 (100 mg, 0.37 mmol) and triethylamine (45 mg., 1.2 Eq.) was treated with 4-ethylbenzoyl chloride (76 mg., 1.2 Eq.). The resulting solid was recrystallized from hexane/ethyl acetate 1:1 to yield 68 mg. of crystals. m.p. 118°–119° C. (46%). NMR was consistent with the proposed title structure. Field Desorption Mass Spectrum: M$^+$403 Analysis for $C_{22}H_{30}N_2O_3S$: Theory: C, 65.64; H, 7.51; N, 6.96. Found: C, 65.84; H, 7.47; N, 7.06.

EXAMPLE 261

N-2-[4-N-(cyclohexylcarboxamido)phenyl]-2-methylpropyl 2-propanesulfonamide

The title compound was prepared as a solid following the method of Example 254, starting with the product of Preparation 82 (100 mg, 0.37 mmol) and triethylamine (45 mg., 1.2 Eq.) was treated with cyclohexanecarbonyl chloride (51 mg., 1.2 Eq.). The resulting solid was recrystallized from hexane/ethyl acetate 3:1 to yield 91 mg. of crystals. m.p. 203°–205° C. (65%). NMR was consistent with the proposed title structure. Field Desorption Mass Spectrum: M$^+$381 Analysis for $C_{20}H_{32}N_2O_3S$: Theory: C, 63.13; H, 8.48; N, 7.36. Found: C, 63.41; H, 8.66; N, 7.58.

EXAMPLE 262

N-2-[4-N-(isonicotinylamido)phenyl]-2-methylpropyl 2-propanesulfonamide

The title compound was prepared as a solid following the method of Example 254, starting with the product of Preparation 82 (100 mg, 0.37 mmol) and triethylamine (90 mg., 2.2 Eq.) was treated with isonicotinoyl chloride HCl (100 mg., 1.2 Eq.). The resulting solid was recrystallized from hexane/ethyl acetate 1:1 to yield 90 mg. as crystals. m.p. 174°–175° C. (65%). NMR was consistent with the proposed title structure. Field Desorption Mass Spectrum: M$^+$376 Analysis for $C_{19}H_{25}N_3O_3S$: Theory: C, 60.78; H, 6.71; N, 11.19. Found: C, 61.01; H, 7.01; N, 11.04.

EXAMPLE 263

N-2-(4-N-(benzamido)phenyl)propyl 2-dimethylsulfamide

To a solution of the amine from Preparation 84 (100 mg, 0.39 mmol) and triethylamine (45 mg, 0.43 mmol) in dichloromethane (20 ml) was added dropwise benzoyl chloride (61 mg., 1.2 Eq.) in dichloromethane (5 ml) at room temperature under nitrogen. After 1 hour, reaction was complete. The solution was washed once with $H_2O$, dried over $K_2CO_3$, and concentrated under reduced pressure to yield 139 mg. of a solid. Material was recrystallized from hexane/ethyl acetate 3:1 to yield 70 mg. as crystals. m.p. 146°–148° C. (50%). NMR was consistent with the proposed title structure. Field Desorption Mass Spectrum: M$^+$362

Analysis for $C_{18}H_{23}N_3O_3S$: Theory: C, 59.81; H, 6.41; N, 11.63. Found: C, 60.08; H, 6.36; N, 11.45.

EXAMPLE 264

N-2-(4-N-(cyclobutylcarboxamido)phenyl)propyl N,N-dimethylsulfamide

The title compound was prepared as a solid following the method of Example 263, starting from the product of Preparation 84 (100 mg, 0.39 mmol) and triethylamine (45 mg., 1.2 Eq.) was treated with cyclobutanecarbonyl chloride (55 mg., 1.2 Eq.). The resulting solid was recrystallized from ethyl acetate/hexane 3:1 to yield 55 mg. of crystals. m.p. 161°–162° C. (42%). NMR was consistent with the proposed title structure. Field Desorption Mass Spectrum: M$^+$340 Analysis for $C_{16}H_{25}N_3O_3S$ Theory: C, 56.61; H, 7.42; N, 12.38. Found: C, 56.91; H, 7.66; N, 12.45.

EXAMPLE 265

N-2-(4-N-(propionylamido)phenyl)propyl N,N-dimethylsulfamide

The title compound was prepared as a solid following the method of Example 263, starting from the product of Preparation 84 (100 mg, 0.39 mmol) and triethylamine (45 mg., 1.2 Eq.) was treated with propionyl chloride (40 mg., 1.2 Eq.). The resulting solid was recrystallized from ethyl acetate/hexane 4:1 to yield 57 mg. of crystals. m.p. 109°–110.5° C. (51%). NMR was consistent with the proposed title structure. Field Desorption Mass Spectrum: M+314 Analysis for $C_{14}H_{23}N_3O_3S$: Theory: C, 53.65; H, 7.40; N, 13.41. Found: C, 53.91; H, 7.48; N, 13.41.

EXAMPLE 266

N-2-(4-N-(2-thienylcarboxamido)phenyl)propyl N,N-dimethylsulfamide

The title compound was prepared as a solid following the method of Example 263, starting from the product of Preparation 84 (100 mg, 0.39 mmol) and triethylamine (45 mg., 1.2 Eq.) was treated with 2-thiophene chloride (70 mg., 1.2 Eq.). The resulting solid was recrystallized from ethyl acetate/hexane 1:1 to yield 62 mg. of crystals. m.p. 148°–150° C. (43%). NMR was consistent with the proposed title structure. Field Desorption Mass Spectrum: M+368 Analysis for $C_{16}H_{21}N_3O_3S_2$: Theory: C, 52.30; H, 5.76; N, 11.43. Found: C, 52.59; H, 5.78; N, 11.23.

EXAMPLE 267

N-2-(4-N-(3-(5-methyl)isoxazolylcarboxamido)phenyl)propyl N,N-dimethylsulfamide

The title compound was prepared as a solid following the method of Example 263, starting from the product of Preparation 84 (100 mg, 0.39 mmol) and triethylamine (45 mg., 1.2 Eq.) was treated with 5-methyl-3-isoxazole acid chloride (70 mg., 1.2 Eq.). The resulting solid was recrystallized from hexane/ethyl acetate 4:1 to yield 78 mg. of crystals. m.p. 138.5°–140° C. (55%) NMR was consistent with the proposed title structure. Field Desorption Mass Spectrum: M+367 Analysis for $C_{16}H_{22}N_4O_4S$: Theory: C, 52.44; H, 6.05; N, 15.29. Found: C, 52.71; H, 6.20; N, 15.28.

EXAMPLE 268

N-2-(4-N-(phenoxymethylcarboxamido)phenyl)propyl N N-dimethylsulfamide

The title compound was prepared as a solid following the method of Example 263, starting with the product of Preparation 84 (100 mg, 0.39 mmol) and triethylamine (45 mg., 1.2 Eq.) was treated with phenoxyacetyl chloride (73 mg., 1.2 Eq.). The resulting solid was recrystallized from hexane/ethyl acetate 9:1 to yield 73 mg. of crystals. m.p. 120°–121° C. (48%). NMR was consistent with the proposed title structure. Field Desorption Mass Spectrum: M+392 Analysis for $C_{19}H_{25}N_3O_4S$: Theory: C, 58.29; H, 6.44; N, 10.73. Found: C, 58.49; H, 6.22; N, 10.45.

EXAMPLE 269

N-2-(4-N-(4-ethylbenzamido)phenyl)propyl N,N-dimethylsulfamide

The title compound was prepared as a solid following the method of Example 263, starting with the product of Preparation 84 (100 mg, 0.39 mmol) and triethylamine (45 mg., 1.2 Eq.) was treated with 4-ethylbenzoyl chloride (80 mg., 1.2 Eq.). The resulting solid was recrystallized from hexane/ethyl acetate 2:1 to yield 87 mg. of crystals. m.p. 131°–133° C. (57%). NMR was consistent with the proposed title structure. Field Desorption Mass Spectrum: M+390 Analysis for $C_{20}H_{27}N_3O_3S$: Theory: C, 61.67; H, 6.99; N, 10.79. Found: C, 61.49; H, 6.79; N, 10.97.

EXAMPLE 270

N-2-(4-N-(isonicotinylamido)phenyl)propyl N,N-dimethylsulfamide

The title compound was prepared as a solid following the method of Example 263, starting with the product of Preparation 84 (73 mg, 0.29 mmol) and triethylamine (75 mg., 2.2 Eq.) was treated with isonicotinoyl chloride HCl (78 mg., 1.2 Eq.). The resulting solid was recrystallized from hexane/ethyl acetate 2:1 to yield 70 mg. as crystals. m.p. 156°–157° C. (50%). NMR was consistent with the proposed title structure. Field Desorption Mass Spectrum: M+363 Analysis for $C_{17}H_{22}N_4O_3S$ Theory: C, 56.34; H, 6.12; N, 15.46. Found: C, 56.62; H, 5.80; N, 15.17.

EXAMPLE 271

N-2-(2-thien-3-yl-5-thienyl)propyl 2-propanesulfonamide

A. (2-Acetyl-5-thien-3-yl)thiophene: A solution of 1.45 g (7.10 mmol) of 2-acetyl-5-bromothiophene, 2.0 g (7.81 mmol) of thiophene 3-boronic acid, 328 mg (0.28 mmol) of tetrakis(triphenylphosphine)palladium and 1.47 g (10.6 mmol) of potassium carbonate in 32 ml of dioxane and 8 ml of water, was heated at 90° C. for 3 days. Brine was added and extracted three times with ethyl acetate. The organic phase was dried over $Na_2SO_4$, filtered and concentrated in vacuo. Chromatography (300 g of silica gel, 25% ethyl acetate/hexane) of the residue afforded 1.10 g (74%) of the title compound.

B. 2-[2-(thien-3-yl)-5-thienyl]propylamine: To a −15° C. solution of 1.1 g (5.3 mmol) of the material prepared in step A and 1.05 g (5.35 mmol) of tosylmethyl isocyanide in 18 ml of DME, a hot solution of 1.07 g (9.54 mmol) of potassium tert-butoxide in 5 ml of tert-butanol was added slowly. The mixture was stirred at −5° C. for 45 min and 2 h at ambient temperature. Water was added and extracted three times with diethyl ether. The organic phase was dried over $Na_2SO_4$, filtered and concentrated in vacuo. The crude material was dissolved in 15 ml of diethyl ether and then was added to a suspension of 218 mg (5.75) of lithium aluminum hydride in 5 ml of diethyl ether. The mixture was stirred at ambient temperature for 2 h. $Na_2SO_4.10H_2O$ was added, and the mixture stirred for 30 min at ambient temperature. The solid was filtered and the organic solution was concentrated in vacuo. Chromatography (150 g of silica gel, ethyl acetate/hexane/methanol 10/10/1) of the residue afforded 250 mg (22%) of the title compound.

C. To a 0° C. solution of 200 mg (0.89 mmol) of the material prepared in step B in dichloromethane (5 ml), triethylamine 0.15 ml (1.07 mmol) was added, followed by isopropylsulfonyl chloride (0.12 ml, 1.07 mmol). The ice-bath was removed and the solution was stirred at ambient temperature for overnight. The organic solution was washed with 1N hydrochloric acid, sodium bicarbonate saturated solution, brine, dried over $Na_2SO_4$ filtered and concentrated in vacuo. Chromatography (100 g of silica gel, 25% ethyl acetate/hexane) of the residue afforded 61 mg (21%) of the title compound. Analysis calculated for $C_{14}H_{19}NO_2S_3$: %C, 51.03; %H, 5.81; %N, 4.25. Found: %C, 51.30; %H, 5.81; %N, 4.25. Field Desorption Mass Spectrum: M=329.

EXAMPLE 272

N-2-(2-thien-3-yl-4-thienyl)propyl 2-propanesulfonamide

Prepared as in Example 271 using 4.38 g (21.31 mmol) of 4-acetyl-2-bromothiophene and 3 g (23.44 mmol) of thiophene 3-boronic acid. After three steps, afforded 421 mg (6% overall yield. Field Desorption Mass Spectrum: M=329.

EXAMPLE 273

N-2-(2-thien-3-yl-5-pyridyl)propyl 2-propanesulfonamide

A. 2-(2-thien-3-yl-5-pyridyl)propanenitrile: A solution of 960 mg (4.8 mmol) of 5-acetyl-2-bromopyridine, 676 mg (5.28 mmol) of thiophene 3-boronic acid, 222 mg (0.19 mmol) of tetrakis(triphenylphosphine) palladium and 995 mg (7.2 mmol) of potassium carbonate in 13 ml of dioxane and 3 ml of water, was heated at 90° C. overnight. Brine was added and extracted three times with ethyl acetate. The organic phase was dried over $Na_2SO_4$, filtered and concentrated in vacuo. To a solution of the crude and 475 mg (14.4 mmol) of lithium cyanide in 16 ml of THF, 2.2 ml (14.4 mmol) of diethylcyanophosphonate was added neat at ambient temperature. The mixture was stirred at ambient temperature for 30 min. Water was added and extracted with a 1:1 solution of ethyl acetate/hexane. The organic solution was dried over $Na_2SO_4$ filtered and concentrated in vacuo. The crude was dissolved in 10 ml of THF and added dropwise to a solution of samarium iodide, prepared from 3.32, g (22.08 mmol) of samarium and 3.89 g (13.8 mmol) of 1,2-diiodoethane. The mixture was stirred for 1 h. A 2.5 N solution of hydrochloric acid was added and extracted three times with diethyl ether. The organic phase was washed with a 1 N solution of sodium thiosulfate. The organic solution was dried over $Na_2SO_4$ filtered and concentrated in vacuo. Chromatography (100 g of silica gel, 25% ethyl acetate/hexane) of the residue afforded 225 mg (22%) of the title compound.

B. To an ambient temperature solution of 214 mg (1 mmol) of material prepared in step A in 5 ml of THF was added dropwise 0.11 ml of a 10 M solution borane-methyl sulfide complex (1.1 mmol) in THF. The mixture was stirred at ambient temperature for 2 h. Then, 0.1 ml of a 10 M solution borane-methyl sulfide complex (1.0 mmol) in THF were added and the mixture stirred overnight. A saturated solution of hydrochloric acid in methanol (5 ml) was added, and stirred for 10 min. The solution was concentrated in vacuo. The crude was dissolved in dichloromethane (5 ml) and cooled to 0° C., triethylamine 0.44 ml (3.2 mmol) was added, followed by isopropylsulfonyl chloride (0.14 ml, 1.2 mmol). The ice-bath was removed and the solution was stirred at ambient temperature for 2 h. The organic solution was washed with 1N hydrochloric acid, sodium bicarbonate saturated solution, brine, dried over $Na_2SO_4$ filtered and concentrated in vacuo. Chromatography (50 g of silica gel, 33% ethyl acetate/hexane) of the residue afforded 25 mg (7%) of the title compound. Field Desorption Mass Spectrum: M=324.

EXAMPLE 274

(+)-N-2R-(4-(3-thienyl)phenyl)propyl 2-propanesulfonamide

To a solution of 0.75 g (3.5 mmol) of material from Preparation 102 and 0.60 mL (3.8 mmol) of 1,8-diaza-bicyclo[5.4.0]undec-7-ene in 10 mL of dichloromethane at 0° C. was added 0.40 mL (3.5 mmol) of 2-propanesulfonyl chloride. The mixture was stirred at room temperature for 4 hr and then was washed with 10 mL of 1N hydrochloric acid, the organic layer was separated and the aqueous layer extracted one time with 5 mL of dichloromethane. The combined organics were dried ($MgSO_4$), filtered and concentrated in vacuo. Recrystallizaton from methyl alcohol afforded 0.46 g (41%) of the title compound.

Analysis calculated for $C_{16}H_{21}NO_2S_2$: %C, 59.41; %H, 6.54; %N, 4.33. Found: %C, 59.69; %H, 6.68; %N, 4.42.

Field Desorption Mass Spectrum: M+1=324.

$[\alpha]_D^{20}$=+42.55 (c=0.99, $CHCl_3$).

EXAMPLE 275

(+)-N-2S-(4-(3-thienyl)phenyl)propyl 2-propanesulfonamide

Following the procedure of Example 274 and using material from Preparation 103 instead of material form Preparation 102 afforded 0.45 g (39%) of the title compound.

Analysis calculated for $C_{16}H_{21}NO_2S_2$: %C, 59.41; %H, 6.54; %N, 4.33. Found: %C, 59.71; %H, 6.35; %N, 4.43.

Field Desorption Mass Spectrum: M+1=324.

$[\alpha]_D^{20}$=−43.98 (c=1.05, $CHCl_3$).

EXAMPLE 276

(+)-N-2R-(4-(3-thienyl)phenyl)propyl N', N'-dimethylsulfamide

To a solution of 0.1 g (0.46 mmol) of material from Preparation 102 and 0.07 mL (0.46 mmol) of 1,8-diaza-bicyclo[5.4.0]undec-7-ene in 10 mL of dichloromethane at 0° C. was added 0.05 mL (0.46 mmol) of N,N-dimethylsulfamoyl chloride. The mixture was stirred at room temperature for 4 hr and then was washed with 10 mL of 1N hydrochloric acid, the organic layer was separated and the aqueous layer extracted one time with 5 mL of dichloromethane. The combined organics were dried ($MgSO_4$), filtered and concentrated in vacuo. Chromatography (10 g of silica gel, 25% ethyl acetate/-hexane) of the residue afforded 0.04 g (26%) of the title compound.

Analysis calculated for $C_{15}H_{20}N_2O_2S_2$: %C, 55.53; %H, 6.21; %N, 8.63. Found: %C, 55.39; %H, 6.08; %N, 8.50.

Field Desorption Mass Spectrum: M+1=325.

$[\alpha]_D^{20}$=+20.75 (c=0.77, $CHCl_3$).

EXAMPLE 277

(−)-N-2S-(4-(3-thienyl)phenyl)propyl N',N'-dimethylsulfamide

Following the procedure of Example 276 and using material from Preparation 103 instead of material form Preparation 102 afforded 0.02 g (13%) of the title compound.

Analysis calculated for $C_{15}H_{20}N_2O_2S_2$: %C, 55.53; %H, 6.21; %N, 8.63. Found: %C, 55.31; %H, 6.23; %N, 8.36.

Field Desorption Mass Spectrum: M+1=325.

$[\alpha]_D^{20}$=−25.81 (c=1.24, $CHCl_3$).

EXAMPLE 278

(+-N-2R-(4-(2-pyridyl)phenyl)propyl 2-propanesulfonamide

A. (R)-2-(4-(2-pyridyl)phenyl)-N-(t-butoxy-carbonyl)propyl amine: To a solution of 1.0 g (3.2 mmol) of material from Preparation 92 and 1.2 g (3.2 mmol) of 2-(tri-n-butylstannyl)pyridine in 10 mL of dioxane was added 0.18 g (0.16 mmol) of tetrakis (triphenylphosphine)palladium(0). The mixture was heated at 100° C. for 18 h. The mixture was cooled and concentrated in vacuo. Chromatography (150 g of silica gel, 25% ethyl acetate/hexane) of the residue afforded 0.87 g (85%) of the title compound.

B. To a solution of 0.85 g (2.7 mmol) of material from Example 278A in 5 mL of ethyl acetate was added 5 mL of hydrochloric acid saturated ethyl acetate. The mixture was stirred at room temperature for 3 hr and then concentrated in vacuo. The residue was suspended in 5 mL of methyl alcohol and concentrated in vacuo and then dissolved in 5 mL of dichloromethane. To the mixture was added 1.2 mL (8.4 mmol) of 1,8-diazabicyclo[5.4.0] undec-7-ene and the solution was cooled to 0° C. To this mixture was added 0.30 mL (2.7 mmol) of 2-propanesulfonyl chloride. The mixture was stirred at room temperature for 4 hr and then was washed with 5 mL of 1N hydrochloric acid, the organic layer was separated and the aqueous layer extracted Three times with 5 mL of dichloromethane. The combined organics were dried (MgSO$_4$), filtered and concentrated in vacuo. Chromatography (25 g of silica gel, 50% ethyl acetate/hexane) of the residue afforded 0.49 g (57%) of the title compound.

Analysis calculated for $C_{17}H_{22}N_2O_2S$: %C, 64.12; %H, 6.96; %N, 8.80. Found: %C, 64.22; %H, 6.71; %N, 8.82.

Mass Spectrum: M+1=319.

$[\alpha]_D^{20}$=+40 (c=1.0, CHCl$_3$).

EXAMPLE 279

(−)-N-2S-(4-(2-pyridyl)phenyl)propyl 2-propanesulfonamide

Following the procedure of Example 278 and using material from Preparation 99 instead of material form Preparation 92 afforded 0.36 g (47%) of the title compound.

Analysis calculated for $C_{17}H_{22}N_2O_2S$: %C, 64.12; %H, 6.96; %N, 8.80. Found: %C, 63.93; %H, 6.86; %N, 8.65.

Mass Spectrum: M+1=319.

$[\alpha]_D^{20}$=−36 (c=1.0, CHCl$_3$).

EXAMPLE 280

N-2-(4-N-phenyloxalylamido)phenyl)propyl 2-propanesulfonamide

A −78° C. solution of the material from Example 222 (0.28 9, 0.79 mmol) in THF (5 ml) was treated with phenyl magnesium bromide (0.27 ml, 0.82 mmol). The reaction mixture was warmed slightly to dissolve the solid. After 1 hr additional phenyl magnesium bromide (0.27 ml, 0.82 mmol) was added at −78° C. and the mixture was stirred for 2 h. The reaction mixture was quenched at −78° C. with 10% solution of ammonium chloride. The organic was extracted with ether (2×20 ml). The combined organic layers were washed with brine (10 ml), dried over magnesium sulfate and concentrated. The crude product was further purified by flash chromatography (SiO$_2$, 30% EtOAc: Hexanes)to give 0.31 g (46%) of a yellow oil as the pure product. NMR was consistent with the proposed title structure. Field Desorption Mass Spectrum: M$^+$=389.3.

EXAMPLE 281

Preparation of N-methyl-N-2-(4-(3-thienyl) phenylpropyl 2-propanesulfonamide

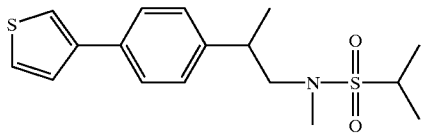

Scheme II: To a solution of 0.5 g (1.6 mmol) of N-2-(4-(3-thienyl)phenyl)propyl 2-propanesulfonamide (see example 103) in 5 mL of tetrahydrofuran was added 1.6 mL (1.6 mmol) of a 1 M solution of sodium bis(trimethylsilyl) amide in tetrahydrofuran. Enough dimethylformamide was added to solublize the resulting precipitate. To the mixture was added 0.3 g (1.9 mmol) of iodomethane and the reaction stirred at room temperature for 16 hours. The mixture was diluted with 10 mL of ethyl acetate and washed once with 10 mL of water. The organic portion was separated and the aqueous portion was extracted two times with 5 mL each of ethyl acetate. The combined organics were dried over anhydrous magnesium sulfate, filtered and concentrated in vacuo. Chromatography (25 g silica gel, 25% ethyl acetate/hexane) of the residue afforded 0.2 g (38%) of the title compound.

Analysis calculated for $C_{17}H_{23}NO_2S_2$: %C, 60.50; %H, 6.87; %N, 4.15. Found: %C, 60.61; %H$_1$, 6.86; %N, 4.17.

Electrospray Mass Spectrum: M+1=338.

In a manner analogous to the procedure described in example 281, the corresponding N-methylated compounds are prepared from the compounds prepared in examples 1–280.

In a manner analogous to the procedures described herein the N-acetylated compounds, such as;

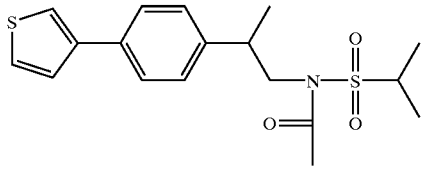

are prepared by one of ordinary skill in the art by reaction of the compounds prepared in examples 1–280 with either acetic anhydride or acetyl chloride in the presence of base, such as triethylamine (See for example T. W. Green, "Protective Groups in Organic Synthesis", John Wiley & Sons, Inc., (1981) pages 251–252).

In a manner analogous to the procedures described herein the —N—CO$_2$C(CH$_3$)$_3$ compounds, such as;

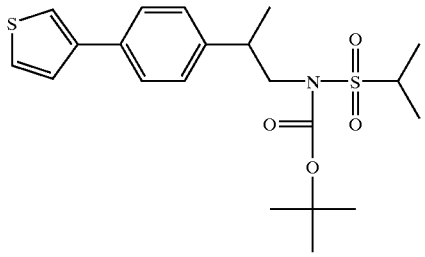

are prepared by one of ordinary skill in the art by reaction of the compounds prepared in examples 1–280 with di-tertbutyl dicarbonate in the presence of base (See for example T. W. Green, "Protective Groups in Organic Synthesis", John Wiley & Sons, Inc., (1981) pages 232–233 and *Synthetic Communications*, 23, 1443 (1993)).

In addition, in a manner analogous to the procedures described herein the —N—CO$_2$CH$_2$C$_6$H$_5$ compounds, such as;

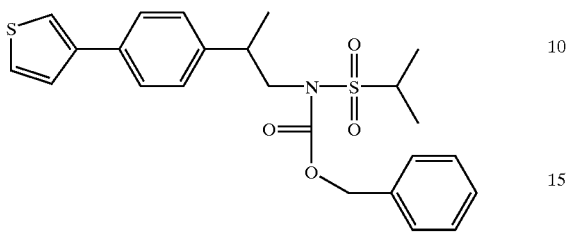

are prepared by one of ordinary skill in the art by reaction of the compounds prepared in examples 1–280 with benzyl chloroformate in the presence of base (See for example T. W. Green, "Protective Groups in Organic Synthesis", John Wiley & Sons, Inc., (1981) pages 239–241).

We claim:
1. A compound of the formula:

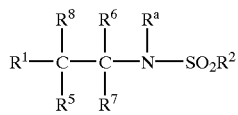

wherein
R$^a$ represents (1–6C)alkyl, CO(1–6C)alkyl, CO(aryl), CO$_2$(1–6C)alkyl, CO$_2$(1–6C)alkylaryl, CO$_2$(aryl), CO(1–6C)alkylNH(1–6C)alkyl, or CO(1–6C)alkylN(1–6C)alkyl$_2$;

R$^1$ represents a naphthyl group or a phenyl group which is unsubstituted or substituted by one or two substituents selected independently from halogen; nitro; cyano; hydroxylmino; (1–10C)alkyl; (2–10C)alkenyl; (2–10C)alkynyl; (3–8C)cycloalkyl; hydroxy(3–8C)cycloalkyl; oxo(3–8C)cycloalkyl; halo(1–10C)alkyl; (CH$_2$)$_y$X$^1$R$^9$ in which y is 0 or an integer of from 1 to 4, X$^1$ represents O, S, NR$^{10}$, CO, COO, OCO, CONR$^{11}$, NR$^{12}$CO, NR$^{12}$COCOO or OCONR$^{13}$, R$^9$ represents hydrogen, (1–10C)alkyl, (3–10C)alkenyl, (3–10C)alkynyl, pyrrolidinyl, tetrahydrofuryl, morpholino or (3–8C)cycloalkyl and R$^{10}$, R$^{11}$, R$^{12}$ and R$^{13}$ each independently represents hydrogen or (1–10C)alkyl, or R$^9$ and R$^{10}$, R$^{11}$, R$^{12}$ or R$^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C) alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula R$^{14}$—(L$^a$)$_n$—X$^2$—(L$^b$)$_m$ in which X$^2$ represents a bond, O, NH, S, SO, SO$_2$, CO, CH(OH), CONH, NHCO, NHCONH, NHCOO, COCONH, OCH$_2$CONH or CH=CH, L$^a$ and L$^b$ each represent (1–4C)alkylene, one of n and m is 0 or 1 and the other is 0, and R$^{14}$ represents a phenyl or heteroaromatic group which is unsubstituted or substituted by one or two of halogen, nitro, cyano, hydroxylmino, (1–10C)alkyl, (2–10C)alkenyl, (2–10C) alkynyl, (3–8C)-cycloalkyl, 4-(1,1-dioxotetrahydro-1, 2-thiazinyl), halo(1–10C)alkyl, cyano(2–10C)alkenyl, phenyl, and (CH$_2$)$_z$X$^3$R$^{15}$ in which z is 0 or an integer of from 1 to 4, X$^3$ represents O, S, NR$^{16}$, CO, CH(OH), COO, OCO, CONR$^{17}$, NR$^{18}$CO, NHSO$_2$, NHSO$_2$NR$^{17}$, NHCONH, OCONR$^{19}$ or NR$^{19}$COO, R$^{15}$ represents hydrogen, (1–10C)alkyl, phenyl(1–4C) alkyl, halo(1–10C)alkyl, (1–4C)alkoxycarbonyl(1–4C) alkyl, (1–4C)alkylsulfonylamino(1–4C)alkyl, (N-(1–4C)alkoxycarbonyl)(1–4C)alkylsulfonylamino-(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and R$^{16}$, R$^{17}$, R$^{18}$ and R$^{19}$ each independently represents hydrogen or (1–10C)alkyl, or R$^{15}$ and R$^{16}$, R$^{17}$, R$^{18}$ or R$^{19}$ together with the nitrogen atom to which they are attached form an azetidinyl, pyrrolidinyl, piperidinyl or morpholino group;

R$^2$ represents ethyl, 2-propyl, or dimethylamino

R$^5$, R$^6$ and R$^7$ represent hydrogen; and

R$^8$ represents methyl;

or a pharmaceutically acceptable salt thereof.

2. A compound according to claim 1 wherein R$^a$ is (1–6C)alkyl, CO(1–6C)alkyl, CO(aryl), CO$_2$(1–6C)alkyl, CO$_2$(1–6C)alkylaryl, or CO$_2$(aryl).

3. A compound according to claim 1 wherein R$^a$ is (1–6C)alkyl.

4. A compound according to claim 1 wherein R$^a$ is methyl.

5. A pharmaceutical composition, which comprises a compound as claimed in claim 1 and a pharmaceutically acceptable diluent or carrier.

6. A method of potentiating glutamate receptor function in a mammal requiring such treatment, which comprises administering an effective amount of a compound of claim 1.

7. A method of treating a cognitive disorder; a neurodegenerative disorder; age-related dementia; age-induced memory impairment; movement disorder; reversal of a drug-induced state; depression; attention deficit disorder; attention deficit hyperactivity disorder; psychosis; cognitive deficits associated with psychosis; or drug-induced psychosis in a patient, which comprises administering to a patient in need thereof an effective amount of a compound according to claim 1.

8. A method for improving memory or learning ability in a patient, which comprises administering to a patient in need thereof an effective amount of a compound according to claim 1.

* * * * *